US008507671B2

(12) United States Patent
Niyaz et al.

(10) Patent No.: US 8,507,671 B2
(45) Date of Patent: *Aug. 13, 2013

(54) INSECTICIDAL SUBSTITUTED AZINYL DERIVATIVES

(75) Inventors: Noormohamed M. Niyaz, Indianapolis, IN (US); Ricky Hunter, Westfield, IN (US); Timothy C. Johnson, Indianapolis, IN (US); Tony K. Trullinger, Westfield, IN (US); Annette V. Brown, Indianapolis, IN (US); Kristy Bryan, Carmel, IN (US)

(73) Assignee: Dow Agrosciences LLC, Indianapolis, IN (US)

( * ) Notice: Subject to any disclaimer, the term of this patent is extended or adjusted under 35 U.S.C. 154(b) by 12 days.

This patent is subject to a terminal disclaimer.

(21) Appl. No.: 13/188,568

(22) Filed: Jul. 22, 2011

(65) Prior Publication Data
US 2012/0190683 A1 Jul. 26, 2012

Related U.S. Application Data

(62) Division of application No. 12/239,079, filed on Sep. 26, 2008, now Pat. No. 8,013,154.

(60) Provisional application No. 60/998,250, filed on Oct. 9, 2007.

(51) Int. Cl.
| *C07D 251/46* | (2006.01) |
| *A01N 43/66* | (2006.01) |
| *C07D 239/52* | (2006.01) |
| *C07D 401/12* | (2006.01) |
| *C07D 213/75* | (2006.01) |
| *A01N 43/54* | (2006.01) |
| *A01N 43/40* | (2006.01) |

(52) U.S. Cl.
USPC ........... 544/204; 544/208; 544/209; 544/217; 544/219; 514/245

(58) Field of Classification Search
USPC .......... 544/204, 208, 209, 217, 219; 514/245
See application file for complete search history.

(56) References Cited

U.S. PATENT DOCUMENTS

| 3,857,883 | A | 12/1974 | Cleveland |
| 4,308,054 | A | 12/1981 | Isogai Yo et al. |
| 4,833,158 | A | 5/1989 | Twydell et al. |
| 6,660,733 | B2 | 12/2003 | Sun et al. |
| 6,693,097 | B2 | 2/2004 | Ono et al. |
| 8,013,154 | B2 * | 9/2011 | Niyaz et al. ............ 544/317 |

FOREIGN PATENT DOCUMENTS

| CN | 1 508 130 A | 6/2004 |
| CN | 1 510 033 A | 7/2004 |
| WO | WO 93/04580 A | 3/1993 |
| WO | WO 03030909 | 4/2003 |
| WO | WO 03091223 | 11/2003 |
| WO | WO 2004006867 | 1/2004 |
| WO | WO/2008/007788 | 4/2009 |
| WO | WO/2008/077888 | 4/2009 |

OTHER PUBLICATIONS

Chen Jimtzuh et al: "Synthesis of N-Phenyl-N'-Pyrimidylurea Derivatives by Selenium or Selenium Dioxide Catalyzed Reductive Carbonylation of Nitroaromatics" Eur.J.Org.Chem. vol. 17, 2003, pp. 3446-3452, XP002521118 p. 3448; table 4.
Database CA [Online] Chemical Abstracts Service, Columbus, Ohio, US; Li, Bin et al: "Synthesis and herbicidal activities of pyrimidinylureas" XP002521119 retrieved from STN Database accesion No. 1997: 379148 abstract & Huazue Yanjiu Yu Yingyong, 9(1), 49-53 Coden: HYYIFM; ISSN: 1004-1656, 1997.
Database CA[Online] Chemical Abstracts Service, Columbus, Ohio, US; Baeva, V. et al; "Synthesis of thiourea derivatives" XP002521120 retreived from STN Database accession No. 1970:31191 abstract & Farmatsiya (Sofia, Bulgaria), 19(3), 11-19 CODEN: FMTYA2; ISSN: 0428-0296, 1969.
Foussard-Blanpin O: "Etude Phamacodynamique Comparee De Carboxamides Diversement Substitutes Dand Le Domaine Du Systeme Nerveus Central" Annales Pharmaceutiques Francaises, Masson, Paris, FR, vol. 40, No. 4, (Jan. 1, 1982), pp. 339-350, XP000943598 ISSN: 0003-4509 table II; compound 887.
Debrath Ashworth R: "Symmetrically Disubstituted Formamdines, Formation by Raney Nickel Reduction of Thioureas" J.Chem. Soc, 1948, pates 1716 -1716, XP009114539 sentence 2, last paragraph; examples.
Kagabu S and Medej S, "Stability Comparison of Imidacloprid and Related Compounds under Simulated Sunligt, Hydrolysis Conditions, and to Oxygen" Biosci. Biotech. Biochem., 59 (6), 980-985, (1995).
Kagabu S, Murata N, Hibino R, Hanzawa M, and Nishimura K, "Insecticidal and Neuroblocking Activities of Thiamethoxam-Type Compounds in the American Cockroach (*Periplaneta americana* L.)" J. Pesticide Sci. 30 (2), 111-115 (2005).
Kollmeyer, WD, Flattum RF, Foster JP, Powell JE, Schroeder ME, and Soloway SB, "Discovery of the Nitromethylene Heterocycle Insecticides" Nicotinoid Insecticides and the Nicotinic Acetylcholine Receptor (pp. 71-89) Eds Yamamotol, and Casida JE.
Shiga Y, Okada I, and Fukuchi T, "Synthesis and Acaricidal Activity of N-(1,3,4-Thiadiazol-2-yl) cyclopropanecarboxamides" J. Pesticide Sci. 28, 61-63 (2003).
Sparks TC, Crouse GD, and Durst D, "Natural products as insecticides: the biology, biochemistry and quantitativestructure-activity relationships of spinosyns and spinosoids" Pest Manag Sci 57:896-905 (2001).
Wakita T,Kinoshita K, Kodaka K, Yasui N, Naoi A, and Banba S "Synthesis and Structure Activity Relationships of Dinotefuran Derivatives: Modification in the Tetrahydro-3-furylmethyl Part" J. Pesticide Sci.29 (4), 356-363 (2004).

* cited by examiner

*Primary Examiner* — Venkataraman Balasubramanian
(74) *Attorney, Agent, or Firm* — Carl D. Corvin

(57) ABSTRACT

N-Azinyl-N'-aryl ureas and thioureas derivatives are effective at controlling insects.

10 Claims, No Drawings

INSECTICIDAL SUBSTITUTED AZINYL DERIVATIVES

This application claims the benefit of U.S. Provisional Application Ser. No. 60/998,250 filed on Oct. 9, 2007. This application also claims the benefit of U.S. Non-provisional application Ser. No. 12/239,079 filed on 26 Sep. 2008.

BACKGROUND OF THE INVENTION

The present invention concerns novel N-azinyl-N'-aryl ureas and thioureas and their use in controlling insects, particularly lepidoptera and/or coleoptera. This invention also includes new synthetic procedures, intermediates for preparing the compounds, pesticide compositions containing the compounds, and methods of controlling insects using the compounds.

There is an acute need for new insecticides and acaricides. Insects and mites are developing resistance to the insecticides and acaricides in current use. At least 400 species of arthropods are resistant to one or more insecticides. The development of resistance to some of the older insecticides, such as DDT, the carbamates, and the organophosphates, is well known. But resistance has even developed to some of the newer pyrethroid insecticides and acaricides. Therefore, a need exists for new insecticides and acaricides, and particularly for compounds that have new or atypical modes of action.

The present invention provides novel compounds with broad-spectrum activity against insects, particularly lepidoptera and/or coleoptera.

SUMMARY OF THE INVENTION

This invention concerns compounds useful for the control of insects, especially useful for the control of lepidoptera and/or coleoptera. More specifically, the invention concerns compounds of the formula (I):

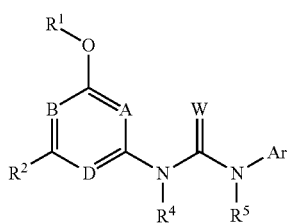

(I)

wherein

A, B and D represent N, CH or $CR^3$, with the proviso that at least one of A, B or D are N;

$R^1$ represents $C_1$-$C_4$ alkyl optionally substituted with from one up to the maximum number of fluorine or chlorine atoms;

$R^2$ represents Cl, $CF_3$, O($C_1$-$C_3$ alkyl), NH($C_1$-$C_3$ alkyl) or N($C_1$-$C_3$ alkyl)$_2$ in which each of the previous $C_1$-$C_3$ alkyl groups is optionally substituted with from one up to the maximum number of fluorine atoms;

$R^3$ represents H, F, Cl, Br, I, $C_1$-$C_3$ alkyl or O($C_1$-$C_3$ alkyl) in which each of the previous $C_1$-$C_3$ alkyl groups is optionally substituted with from one up to the maximum number of fluorine atoms;

$R^4$ represents H, $C_1$-$C_3$ alkyl (optionally substituted with alkoxy, benzyloxy or —OC(O)$R^7$), or $CO_2R^6$;

$R^5$ represents H, $C_1$-$C_3$ alkyl (optionally substituted with $C_1$-$C_3$ alkoxy, F, CN or $CO_2R$), OH, $C_1$-$C_3$ alkoxy or $CO_2R^6$, or $R^4$ and $R^5$ taken together represent —$CH_2CH_2$— or —C(O)$CH_2$—;

$R^6$ represents H or $C_1$-$C_3$ alkyl;

$R^2$ represents $C_1$-$C_3$ alkyl;

W represents O or S;

Ar represents a phenyl group substituted with one to four substitutents independently selected from F, Cl, Br, I, $NO_2$, CN, $SCF_3$, $SO_2CF_3$, $C_1$-$C_3$ alkyl substituted with from one up to the maximum number of chlorine or fluorine atoms, or $C_1$-$C_3$ alkoxy optionally substituted with from one up to the maximum number of chlorine or fluorine atoms; or represents

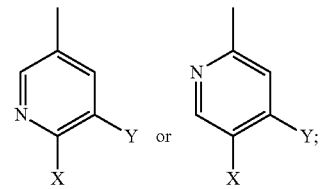

and

X and Y independently represent H, F, Cl, Br, I, $NO_2$, CN, $SCF_3$, $SO_2CF_3$, $C_1$-$C_3$ alkyl substituted with from one up to the maximum number of chlorine or fluorine atoms, or $C_1$-$C_3$ alkoxy optionally substituted with from one up to the maximum number of chlorine or fluorine atoms.

Preferred compounds of formula (I) include the following classes:

(1) Compounds of formula (I) wherein $R^1$ is $CH_2CF_3$.
(2) Compounds of formula (I) wherein $R^2$ is $OCH_2CF_3$.
(3) Compounds of formula (I) wherein W is O
(4) Compounds of formula (I) wherein $R^4$ and $R^5$ are independently H or $CH_3$.
(5) Compounds of formula (I) wherein Ar represents

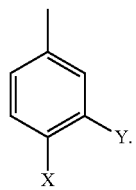

(6) Compounds of formula (I) wherein X is Br, Cl, $CF_3$ or $OCF_3$.

It will be appreciated by those skilled in the art that the most preferred compounds are generally those which are comprised of combinations of the above preferred classes.

The invention also provides new processes and intermediates for preparing compounds of formula (I) as well as new compositions and methods of use, which will be described in detail herein below.

DETAILED DESCRIPTION OF THE INVENTION

Throughout this document, all temperatures are given in degrees Celsius, and all percentages are weight percentages unless otherwise stated.

Unless specifically limited otherwise, the term "alkyl", as well as derivative terms such as "alkoxy", as used herein, include within their scope straight chain, branched chain and cyclic moieties.

Unless specifically limited otherwise, the term "halogen", as well as derivative terms such as "halo", as used herein, refers to fluorine, chlorine, bromine, and iodine. Preferred halogens are fluorine and chlorine.

The term "haloalkyl" refers to alkyl groups substituted with from one up to the maximum possible number of halogen atoms. The terms "haloalkoxy" and "halothioalkyl" refer to alkoxy or thioalkyl groups substituted with from one up to the maximum possible number of halogen atoms.

Unless otherwise indicated, when it is stated that a group may be substituted with one or more substituents selected from an identified class, it is intended that the substituents may be independently selected from the class.

Compounds of formula (I) can be prepared by the methods illustrated in Schemes A-C below.

Compounds of formula (I) wherein $R^1$, $R^2$, A, B, D, W, and Ar are as previously defined and wherein $R^4$ and $R^5$ are both H can be prepared by the methods illustrated in Scheme A.

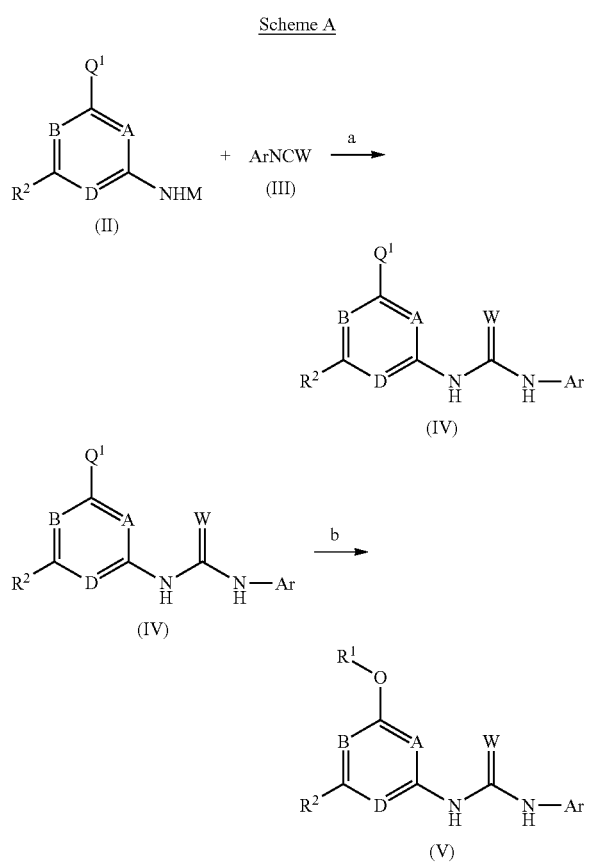

In Scheme A, the metal salt of an amino heterocycle of formula (II) wherein M represents a metal, such as sodium, and $Q^1$ represents Cl or $R^1O$, is reacted with aryl isocyanates and aryl isothiocyanates of formula (III), wherein W represents O or S, in a polar aprotic organic solvent, such as tetrahydrofuran (THF), to afford compounds of formula (IV). The reactions are generally carried out at temperatures from –20° C. to about 50° C. and are usually complete in one to 18 hours. The compounds can be recovered and purified by conventional methods. The metal salts of formula (II) wherein M represents a metal are prepared by reaction of an amino heterocycle of formula (II) wherein M represents hydrogen with a base, such as sodium hydride. Means to exclude moisture, such as a blanket of dry nitrogen, are employed during this process. The preferred base is sodium hydride (M=Na) and the preferred solvent is THF. However, other strong bases, such as potassium tert-butoxide or n-butyl lithium, and other aprotic organic solvents, such as ethyl ether or 1,4-dioxane, can also be used. Compounds of formula (IV) can be further manipulated by reaction with nucleophiles such as alkoxides to give compounds of formula (V). The alkoxides are generally prepared by reaction of an alcohol with a base, such as sodium hydride, in an anhydrous aprotic solvent such as THF. The alkoxide is then reacted with compounds of formula (IV) in the same solvent to give compounds of formula (V). The reactions are generally carried out at temperatures from –20° C. to about 100° C. and are usually complete in one to 18 hours. The compounds can be recovered and purified by conventional methods.

Compounds of formula (II) in Scheme A wherein M represents H can be prepared by methods disclosed herein or general methods known in the art.

Many compounds of formula (I) wherein $R^1$, $R^2$, $R^5$, A, B, D, W, and Ar are as previously defined and wherein $R^4$ is H can also be prepared by the methods illustrated in Scheme B.

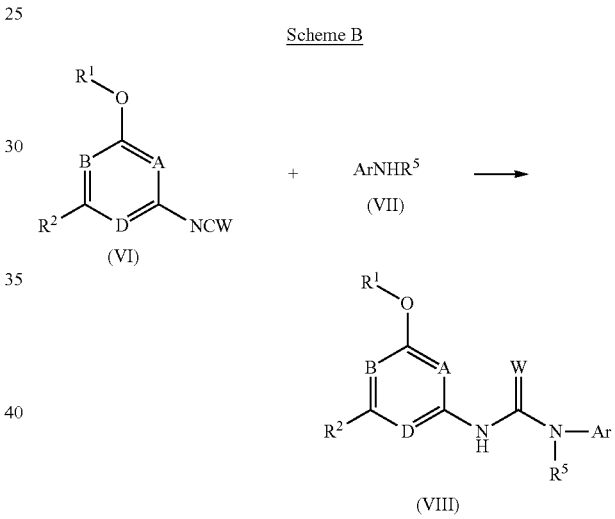

In Scheme B, heterocyclic isocyanates and isothiocyanates of formula (VI), wherein W represents O or S, are reacted with aryl amines of formula (VII) in a polar aprotic solvent, such as $CH_2Cl_2$, to give compounds of formula (VIII). Means to exclude moisture, such as a blanket of dry nitrogen, are typically employed. The reaction is typically carried out at temperatures from –20° C. to about 50° C. and are usually complete in one to 18 hours. The products of formula (VIII) can be recovered by conventional means and purified by conventional methods, such as chromatography or recrystallization. Heterocyclic isocyanates and isothiocyanates of formula (VI) can be prepared from heterocyclic amines of formula (II) wherein W represents H by conventional methods known in the art (for example see: Von Gizychi, U. *Angew. Chem., Int. Ed. Engl.* 1971, 10, 402; Von Gizychi, U. *Angew. Chem., Int. Ed. Engl.* 1971, 10, 403; Oh, L. M.; Spoors, P. G.; Goodman, R. M. *Tetrahedron Lett.* 2004, 45, 4769; S. Ozaki, *Chem. Rev.* 1972, 72, 457; Chem. Abstr. 65:20386; T. Shibanuma et al. *Chem. Lett.* 1977, 5, 573; Organic Functional Group Preparation, Second Edition, S. Sandler and W. Karo, Volume I, Academic Press, 1983) and methods disclosed herein.

Many compounds of formula (I) wherein $R^1$, $R^2$, $R^4$, $R^5$, A, B, D, and Ar are as previously defined and wherein W is O can be prepared as outlined in Scheme C.

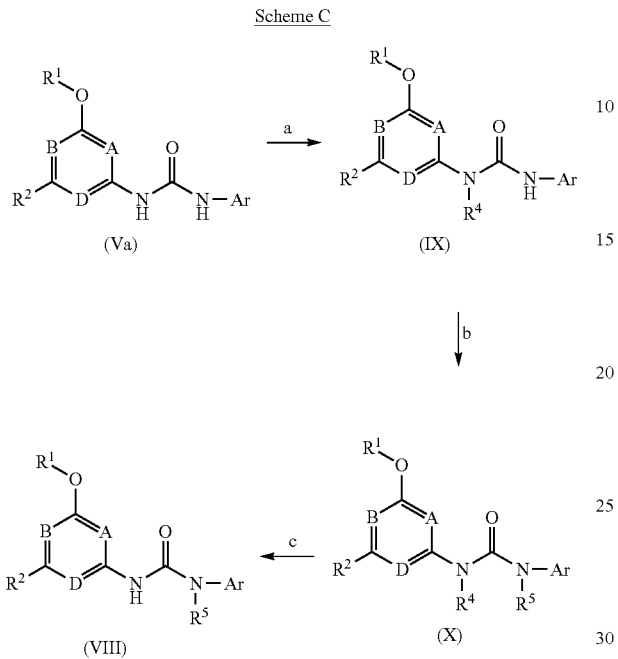

In step a of Scheme C, compounds of formula (Va) can be treated with a base, such as sodium hydride in a polar aprotic organic solvent, such as THF, followed by reaction with an electrophilic reagent, such as methyl iodide, benzyloxymethyl chloride, or other alkyl electrophiles, to give compounds of formula (IX). The reactions are typically run at temperatures ranging from −20 to 50° C. and are generally complete in one to 18 hours. The compounds can be recovered and purified by conventional methods. In step b of Scheme C, compounds can again be treated with a base, such as sodium hydride in a polar aprotic organic solvent followed by reaction with an electrophilic reagent, such as methyl iodide or other alkyl electrophiles, to give compounds of formula (X). Steps a and b of Scheme C can also be performed in one process where compounds of formula (Va) are treated with two or more equivalents of a base, such as sodium hydride, followed by reaction with an excess of electrophilic reagent to afford compounds of formula (X). In step c of Scheme C, compounds of formula (VIII) can be prepared from compounds of formula (X) by removal of $R^4$ when $R^4$ is such a group that it can be removed without removal of $R^5$ (for example see: Protecting Groups in Organic Synthesis, third edition, T. W. Greene and P. G. M. Wuts, John Wiley and Sons, Inc., 1999). In steps a thru c of Scheme C, the products can be recovered by conventional means well known in the art.

Many compounds of formula (I) wherein $R^1$, $R^2$, $R^5$, A, B, D, and Ar are as previously defined and wherein $R^4$ is H can also be prepared by the methods illustrated in Scheme D.

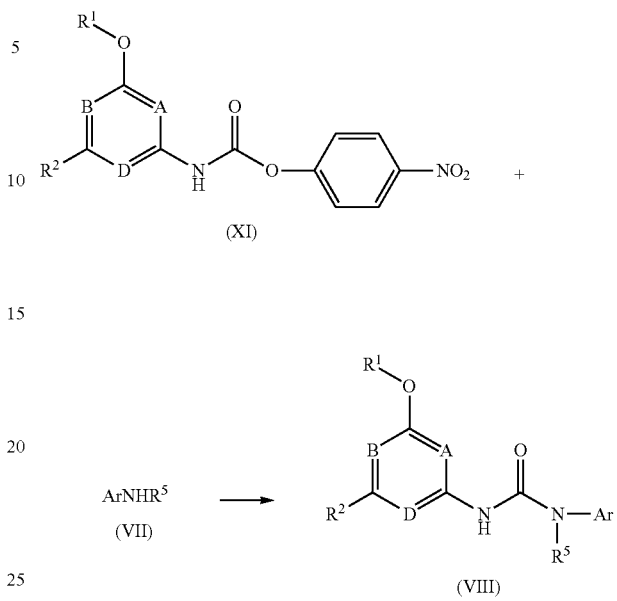

In Scheme D compounds of formula (XI) can be treated with aryl amines of formula (VII) in polar aprotic solvents, such as THF, to give compounds of formula (VIII). Means to exclude moisture, such as blanket of nitrogen, are typically employed. The reaction is typically carried out at temperature from −20° C. to about 50° C. and are typically complete in one hour to 15 days. The products of formula (VIII) can be recovered by conventional means and purified by conventional methods, such as chromatography and recrystallization. Heterocyclic carbamates of formula (XI) can be prepared by conventional methods known in the art and those disclosed herein.

The following examples are presented to illustrate the invention.

Example 1

Preparation of N'-[4,6-bis(2,2,2-trifluoroethoxy)pyrimidin-2-yl]-N-[4-(trifluoro-methyl)phenyl]urea (1)

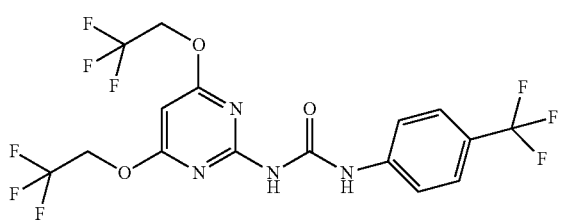 [SMILES: O=C(Nc1ccc(C(F)(F)F)cc1)Nc1nc(OCC(F)(F)F)cc(OCC(F)(F)F)n1]

A. Preparation of N'-[4,6-dichloropyrimidin-2-yl]-N-[4-(trifluoromethyl)-phenyl]urea

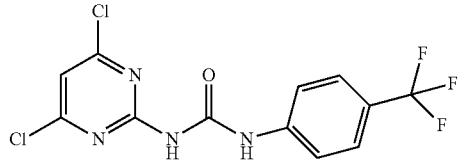 [SMILES: O=C(Nc1ccc(C(F)(F)F)cc1)Nc1nc(Cl)cc(Cl)n1]

To a solution of 2-amino-4,6-dichloropyrimidine (4.10 g, 25 mmol) in anhydrous THF (125 mL), under an atmosphere of $N_2$, at 0° C. was added NaH (25 mmol, 1.02 g, 60% in mineral oil) and the mixture was stirred for 20 min. To this mixture was added 4-trifluoromethylphenyl isocyanate (4.678 g, 25 mmol) and stirred at 0° C. for 2 h. The mixture was poured into a mixture of ethyl acetate and 2N aq. HCl and the organic phase separated. The organic phase was washed with sodium bicarbonate and brine, dried (MgSO4), filtered and concentrated in vacuo to give a solid. This solid was mixed with ether and filtered to give N'-[4,6-dichloropyrimidin-2-yl]-N-[4-(trifluoromethyl)phenyl]urea (2.6 g, 30% yield): m.p. 99-101° C.; $^1$H NMR (DMSO-d$_6$) δ 10.78 (bs, 1H), 10.55 (bs, 1H), 7.69 (m, 4H), 7.58 (s, 1H); ESI/MS 348.88 (M−H) 350.97 (M+H).

B. Preparation of N'-[4,6-bis(2,2,2-trifluoroethoxy)pyrimidin-2-yl]-N-[4-(trifluoromethyl)phenyl]urea (1)

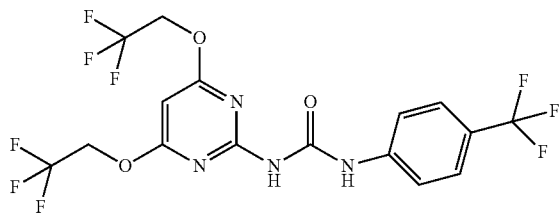 [SMILES: O=C(Nc1ccc(C(F)(F)F)cc1)Nc1nc(OCC(F)(F)F)cc(OCC(F)(F)F)n1]

Sodium hydride (272 mg, 6.8 mmol, 60% in mineral oil) was added to a solution of 2,2,2-trifluoroethanol (1.5 g, 15 mmol) in anhydrous THF (15 mL) at 0° C. and the mixture stirred for 20 min. To this mixture was added N'-[4,6-dichloropyrimidin-2-yl]-N-[4-(trifluoromethyl)phenyl]urea (1.14 g, 3.24 mmol) and stirred at 0° C. for 1 h. The cooling bath was removed and the mixture allowed to warm to room temperature. The mixture was warmed to 45° C. and stirred for additional 18 h. The mixture was poured into water and stirred for 10 min and filtered to afford 1 (1.4 g, 68% yield): m.p. 167-168° C.; $^1$H NMR (DMSO-d$_6$) δ 10.44 (bs, 1H), 10.28 (bs, 1H), 7.76 (d, J=6 Hz, 2H), 7.69 (d, J=6 Hz, 2H), 6.29 (s, 1H), 5.13 (q, J=9.0 Hz, 4H); ESI/MS 476.92 (M−H), 478.95 (M+H).

Example 2

Preparation of N'-[4,6-bis(2,2,2-trifluoroethoxy)pyrimidin-2-yl]-N-methyl-N-[4-(trifluoromethoxy)phenyl]urea (7)

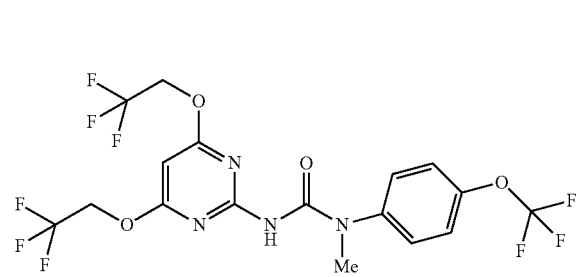 [SMILES: CN(C(=O)Nc1nc(OCC(F)(F)F)cc(OCC(F)(F)F)n1)c1ccc(OC(F)(F)F)cc1]

A. Preparation of 2-amino-4,6-Bis(2,2,2-trifluoroethoxy)pyrimidine

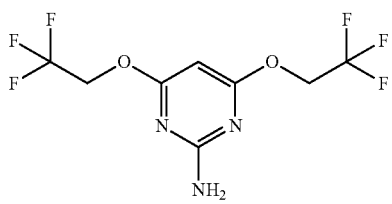 [SMILES: Nc1nc(OCC(F)(F)F)cc(OCC(F)(F)F)n1]

To a solution of trifluoroethanol (9.0 mL, 125 mmol) in anhydrous THF (100 mL) at 0° C. in a 3-neck round bottom flask under an atmosphere of dry $N_2$ was added NaH (4.8 g, 120 mmol, 60% dispersion in mineral oil) over ca. 1 min. After gas evolution ceased and the solution became clear (ca. 20 min), 2-amino-4,6-dichloropyrimdine (8.2 g, 50 mmol) was added. The flask was fitted with a reflux condenser and heated to 62° C. overnight (ca. 15 h). An NMR of a quenched aliquot from the reaction mixture demonstrated the reaction was complete. After the reaction mixture was cooled to ambient temperature it was quenched by addition of 1 N HCl and diluted with EtOAc. The separated organic layer was washed with brine, sat. aq. NaHCO$_3$ and then brine. After drying over MgSO$_4$, filtering and concentrating, the oil thus obtained was dissolved in acetonitrile and washed with hexanes (2×, to remove mineral oil) and concentrated to afford the desired amine as an orange oil (13.9 g, 96% yield): Kugelrohr distillation (high vacuum, 90° C. bath temperature, ice bath for receiving flask) afforded the product as a white solid: m.p.

34-35° C.; $^1$H NMR (CDCl$_3$) δ 5.69 (s, 1H), 4.95 (br s, 2H), 4.69 (q, 4H, J=8.1 Hz); GCMS (EI, 70 eV) m/z 291 (M+).

B. Preparation of 2-isocyanato-4,6-bis(2,2,2-trifluoroethoxy)pyrimidine

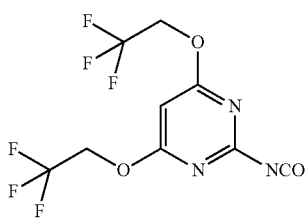

Oxalyl chloride (42.0 mL, 481 mmol) was dissolved in anhydrous 1,4-dioxane (400 mL) under an N$_2$ atmosphere. The resulting solution was heated to 90° C. To the hot solution was slowly added a solution of 2-amino-4,6-bis(2,2,2-trifluoroethoxy)pyrimidine (14.0 g, 48 mmol) in anhydrous 1,4-dioxane (50 mL). After addition of the aminopyrimidine solution was complete, heating was continued for 6 h, the heat removed, and the solution cooled to room temperature. The solution was concentrated and the residue distilled at reduced pressure to afford the product as a clear oil (12.4 g, 82% yield): by 53-54° C. (ca. 0.1 to 0.2 mm Hg): $^1$H NMR (CDCl$_3$) δ 6.19 (s, 1H), 4.82-4.74 (q, 2H, J=8.2 Hz).

C. Preparation of N'-[4,6-bis(2,2,2-trifluoroethoxy)pyrimidin-2-yl-]-N-methyl-N-[4-(trifluoromethoxy)phenyl]urea (7)

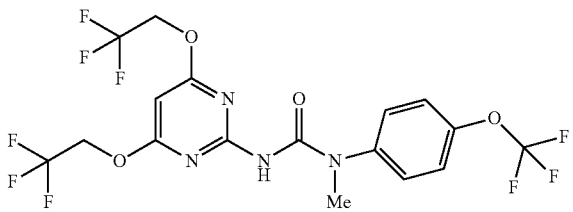 [SMILES: CN(C(=O)Nc1nc(OCC(F)(F)F)cc(OCC(F)(F)F)n1)c1ccc(OC(F)(F)F)cc1]

To a solution of 2-isocyanato-4,6-bis(2,2,2-trifluoroethoxy)pyrimidine (400 mg, 1.26 mmol) in CH$_2$Cl$_2$ (1 mL) was added a solution of N-methyl-4-(trifluoromethoxy)aniline (285 mg, 1.50 mmol) in CH$_2$Cl$_2$ (2 mL). The resulting solution was stirred 18 h and then concentrated. The resulting residue was purified by column chromatography (silica, hexanes/EtOAc) to afford 7 as a white solid (247 mg, 38% yield): m.p. 100-102° C.; $^1$H NMR (CDCl$_3$) δ 7.39 (app s, 4H), 5.96 (s, 1H), 6.82 (bs, 1H), 4.77-4.69 (q, 4H, J=8.5 Hz); ESI/MS 509 (M+H), 507 (M−H).

Example 3

Preparation of N-(4-trifluoromethoxyphenyl)-N'-[4,6-(2,2,2-trifluoroethoxy)pyrimidin-2-yl]urea (3)

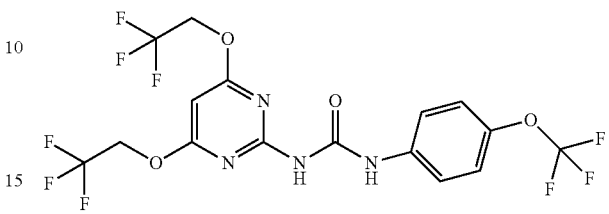

To an anhydrous THF (4.0 mL) solution of the 4-trifluoromethoxyaniline (134 μL, 1.0 mmol) at room temperature was added 2-isocyanato-4,6-bis(2,2,2-trifluoroethoxy)pyrimidine (1.0 mL of a 1.0 M stock solution in THF). After stirring for 45 minutes the solvent was removed under reduced pressure and the solids were then vigorously stirred with hexanes for 10 min. Filtration under reduced pressure afforded 1 as a white flaky solid (358 mg, 72% yield): m.p. 178-180° C.; $^1$H NMR (DMSO-d$_6$) δ 10.36 (s, 1H), 10.25 (s, 1H), 7.66 (d, 2H, J=9.0 Hz), 7.37 (d, 2H, J=9.0 Hz), 6.30 (s, 1H), 5.14 (q, 4H, J=17.8, 9.1 Hz); ESI/MS 495 (M+H), 493 (M−H).

Example 4

Preparation of N-(4-trifluoromethylphenyl)-N'-[4-trifluoromethyl-6-(2,2,2-trifluoroethoxy)pyrimidin-2-yl]urea (102)

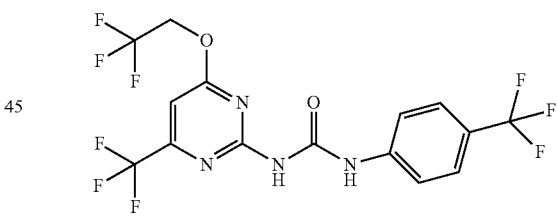

A. Preparation of 2-Amino-4-(trifluoromethyl)-6-(2,2,2-trifluoroethoxy)-pyrimidine

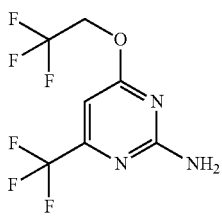 [SMILES: Nc1nc(OCC(F)(F)F)cc(C(F)(F)F)n1]

2,2,2-Trifluoroethanol (2.2 mL, 30 mmol) was slowly added to a suspension of NaH (1.5 g, 36 mmol, 60% dispersion in mineral oil) in anhydrous THF (50 mL) under an $N_2$ atmosphere. To the resulting mixture was added a solution of 2-amino-4-chloro-6-trifluoromethylpyrimidine (5.0 g, 25 mmol; for preparation see: Giner-Sorolla, A. and Bendich, A. *J. Am. Chem. Soc.* 1957, 80, 5744 and Gershon, H. et al. *J. Het. Chem.* 1983, 20, 219) in anhydrous THF (50 mL). The resulting mixture was stirred 18 h at room temperature and the solvent evaporated. The resulting residue was partitioned between $CH_2Cl_2$ (200 mL) and $H_2O$ (200 mL). The organics separated, dried over $MgSO_4$, filtered and evaporated to afford 2-amino-4-(2,2,2-trifluoroethoxy)-6-trifluoromethylpyrimidine as a tan solid (4.9 g, 74% yield): m.p. 108-110° C.; $^1$H NMR (CDCl$_3$) δ 6.54 (s, 1H), 5.53 (bs, 2H), 4.76 (q, 2H, J=8.2 Hz); GCMS (EI, 70 eV) m/z 261 (M+).

B. Preparation of N-(4-trifluoromethylphenyl)-N'-[4-trifluoromethyl-6-(2,2,2-trifluoroethoxy)pyrimidin-2-yl]urea (102)

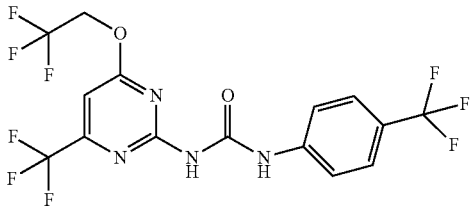 [SMILES: O=C(Nc1ccc(C(F)(F)F)cc1)Nc1nc(OCC(F)(F)F)cc(C(F)(F)F)n1]

To a suspension of NaH (152 mg, 3.8 mmol, 60% dispersion in mineral oil) in anhydrous THF (2 mL) at room temperature was slowly added a solution of 2-amino-4-(trifluoromethyl)-6-(2,2,2-trifluoroethoxy)pyrimidine (0.50 g, 1.9 mmol) in anhydrous THF (2 mL) and the resulting mixture was stirred 20 min. To the mixture was added 4-trifluoromethylphenyl isocyanate (326 µL, 2.28 mmol) and the resulting mixture was allowed to stir at room temperature. After 18 h of stirring the reaction mixture was diluted with 2 N HCl (30 mL). The acidic mixture was extracted with ethyl acetate. The organics were combined, dried over $MgSO_4$, filtered and concentrated. The resulting residue was mixed with ethyl acetate (30 mL), diluted with hexane (100 mL) and allowed to stand at room temperature. After 18 h the insoluble material was filtered and dried in a vacuum oven (50° C.) to afford 102 as a white solid (379 mg, 44% yield): m.p. 197-199° C.; $^1$H NMR (DMSO-d$_6$) δ 10.76 (s, 1H), 10.71 (s, 1H), 7.72 (app s, 4H), 7.35 (s, 1H), 5.25-5.16 (q, 2H, J=8.9 Hz); ESI/MS 448 (M+H), 447 (M–H).

Example 5

Preparation of N-(4-bromophenyl)-N'-[4-ethoxy-6-(2,2,2-trifluoroethoxy)-pyrimidin-2-yl-]-N-methylurea (103)

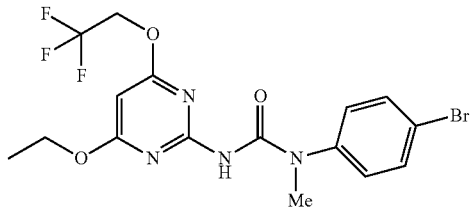 [SMILES: CCOc1cc(OCC(F)(F)F)nc(NC(=O)N(C)c2ccc(Br)cc2)n1]

To a suspension of NaH (320 mg, 8.0 mmol, 60% dispersion in mineral oil) in anhydrous DMF (5 mL) under an $N_2$ atmosphere was added anhydrous EtOH (583 µL, 10 mmol). To this solution was added a solution of N-(4-bromophenyl)-N-[4,6-bis(2,2,2-trifluoroethoxy)pyrimidin-2-yl]-N-methylurea (1.0 g, 2.0 mmol), prepared in a manner similar to 7, in anhydrous DMF (3 mL). The resulting solution was heated (ca. 60° C.) for 2 h, the heat was removed and the solution cooled to room temperature. The solution was diluted with EtOAc (100 mL) and extracted with 2 N HCl (2×50 mL). The organics were dried over $MgSO_4$, filtered and concentrated to afford a brown oil. The brown oil was eluted through a plug of silica using a mixture of hexane and EtOAc and the resulting organic solution concentrated to afford a yellow oil. The yellow oil was further purified by reverse phase chromatography (HPLC grade acetonitrile and water, both with 0.1% acetic acid) to afford 103 as a yellow tacky oil (186 mg, 41% yield): $^1$H NMR (CDCl$_3$) δ 7.64 (d, 2H, J=8.8 Hz), 7.24 (d, 2H, J=8.8 Hz), 6.84 (s, 1H), 4.81-4.72 (q, 2H, J=8.5 Hz), 4.33-4.26 (q, 2H J=7.1 Hz), 1.39-1.37 (t, 3H, J=7.1 Hz); ESI/MS 449, 451 (M+H), 447, 449 (M–H).

Example 6

Preparation of N'-[4,6-bis(2,2,2-trifluoroethoxy)pyrimidin-2-yl]-N-methyl-N-[4-(trifluoromethyl)phenyl]thiourea (131)

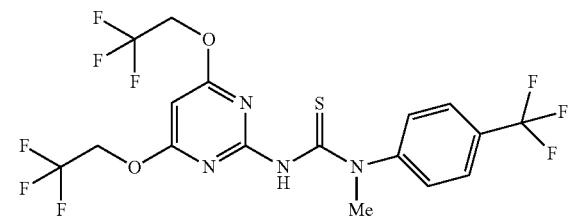 [SMILES: CN(C(=S)Nc1nc(OCC(F)(F)F)cc(OCC(F)(F)F)n1)c1ccc(C(F)(F)F)cc1]

A. Preparation of 4,6-Bis(2,2,2-trifluoroethoxy)pyrimidin-2-yl isothiocyanate

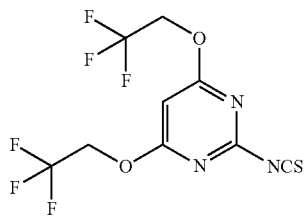

2-Amino-4,6-bis(2,2,2-trifluoroethoxy)pyrimidine (20.0 g, 68.7 mmol) was added to a solution of thiophosgene (15.7 mL, 206 mmol) in anhydrous dioxane (100 mL) under an $N_2$ atmosphere. The resulting solution was heated to reflux. After 18 h the heat was removed and the reaction cooled to room temperature. The dioxane was evaporated to give a dark oil. The dark oil was distilled to afford the product as a light yellow oil (13.7 g, 60% yield); by 83-86° C., (ca 0.2 mmHg):

¹H NMR (CDCl₃) δ 6.24 (s 1H), 4.78 (q, 4H, J=8.2 Hz); GCMS (EI, 70 eV) m/z 333 (M+).

B. Preparation of N'-[4,6-bis(2,2-trifluoroethoxy) pyrimidin-2-yl]-N-methyl-N-[4-trifluoromethyl) phenyl]thiourea (131)

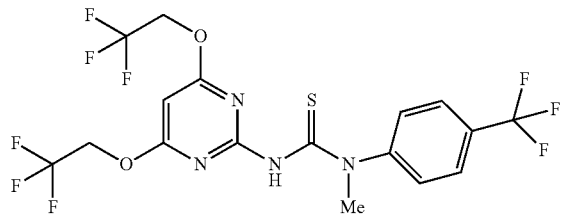 [SMILES: CN(C(=S)Nc1nc(OCC(F)(F)F)cc(OCC(F)(F)F)n1)c1ccc(C(F)(F)F)cc1]

To a solution of 4,6-bis(2,2-trifluoroethoxy)pyrimidin-2-yl isothiocyanate (6.87 mmol) in CH₂Cl₂ (10 mL) was added N-methyl-4-trifluoromethylaniline (6.87 mmol) and the resulting solution was stirred at room temperature. After 18 h the solvent was evaporated and the crude material purified by chromatography (silica, hexane/EtOAc) to afford 131 as a yellow solid (2.15 g, 62% yield): m.p. 109-111° C.; ¹H NMR (CDCl₃) δ 7.76 (d, 2H, J=8.5), 7.46 (d, 3H, J=8.5 Hz), 5.96 (s, 1H), 4.77-4.68 (q, 4H, J=8.5 Hz); ESI/MS 509 (M+H), 507 (M−H).

Example 7

Preparation of N'-[4,6-bis(2,2-trifluoroethoxy)pyrimidin-2-yl-]-N-methyl-N-(4-bromophenyl)urea (41)

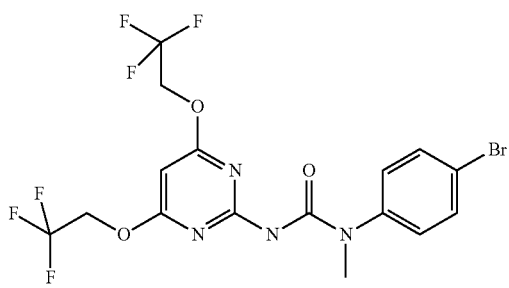 [SMILES: CN(C(=O)Nc1nc(OCC(F)(F)F)cc(OCC(F)(F)F)n1)c1ccc(Br)cc1]

2-Isocyanato-4,6-bis(2,2-trifluoroethoxy)pyrimidine (750 mg, 2.4 mmol) was dissolved in anhydrous dioxane (15 mL). To this solution was added 4-bromo-N-methylaniline (440 mg, 2.36 mmol) and the resulting solution was stirred under an N₂ atmosphere at room temperature. After ca. 12 h an LCMS analysis of the reaction indicated mostly desired product (91%). The reaction was partitioned between EtOAc and water, the organics separated and the aqueous layer extracted with EtOAc (3×50 mL). Organic extracts were combined, washed with water (2×) and once with brine. The organic layer was dried over Na₂SO₄, filtered, and the solvent was removed under reduced pressure to give a yellow oil. The oil was partially purified by column chromatography (silica, hexane/EtOAc) and then recrystallized (EtOAc/cyclohexane) to afford 41 as a white solid (346 mg, 29% yield): m.p. 110-111° C. Anal Calcd for C₁₆H₁₃BrF₆N₄O₃: C, 38.19; H, 2.60; N, 11.13. Found: C, 38.42; H, 2.66; N, 11.20. ¹H NMR (300 MHz, CDCl₃) δ 9.42 (s, 1H), 7.55 (d, 2H, J=4.5 Hz), 7.26 (d, 2H, J=4.5 Hz), 6.14 (s, 1H), 4.99 (q, 4H, J=4.4 Hz), 3.28 (s, 3H).

Example 8

Preparation of N'-[4,6-bis(2,2-trifluoroethoxy)-1,3,5-triazin-2-yl]-N-(4-chlorophenyl)-N-methylurea (121)

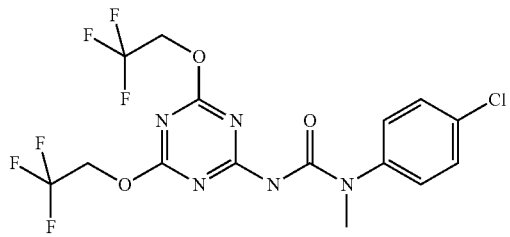 [SMILES: CN(C(=O)Nc1nc(OCC(F)(F)F)nc(OCC(F)(F)F)n1)c1ccc(Cl)cc1]

2-Isocyanato-4,6-bis(2,2-trifluoroethoxy)triazine (8.8 mL, 0.88 mmol of a 0.1M solution in anhydrous THF) was combined with N-methyl-4-chloroaniline (113 mg, 0.88 mmol) and the resulting solution was agitated overnight. After ca. 18 h of agitation the solvent was evaporated and the resulting residue was recrystallized (acetone/cyclohexane) to afford 121 as a white solid (396 mg, 44% yield): m.p. 218-219° C. Anal Calc for C₁₄H₁₀ClF₆N₅O₃: C, 37.73; H, 2.26; N, 15.71. Found: C, 37.92; H, 2.35; N, 15.51. ¹H NMR (300 MHz, DMSO-d₆) δ 10.81 (s, 1H), 10.41 (s, 1H), 7.55 (d, 2H, J=9.0 Hz), 7.42 (d, 2H, J=9.0 Hz), 5.17 (q, 4H, J=8.9 Hz).

Example 9

Preparation of N'-[4,6-bis(2,2-trifluoroethoxy)-1,3,5-triazin-2-yl-]-N-(4-trifluoromethylphenyl)-N-methylurea (118)

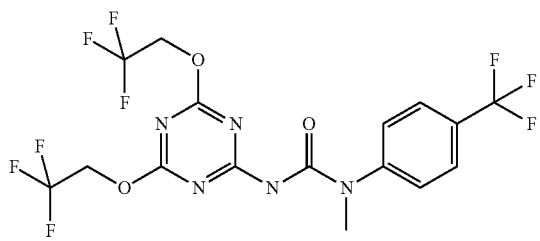 [SMILES: CN(C(=O)Nc1nc(OCC(F)(F)F)nc(OCC(F)(F)F)n1)c1ccc(C(F)(F)F)cc1]

2-Isocyanato-4,6-Bis(2,2-trifluoroethoxy)triazine (8.8 mL, 0.88 mmol of a 0.1M solution in anhydrous THF) was combined with N-methyl-4-(trifluoromethyl)aniline (155 mg, 0.88 mmol) and agitated overnight (ca. 18 h). The solvent was evaporated and the resulting residue recrystallized (EtOAc/cyclohexane) to afford 118 as a white solid (325 mg, 74% yield): m.p. 130-132° C. Anal Calc for C₁₆H₁₂F₉N₅O₃: C, 38.96; H, 2.45; N, 14.20. Found: C, 38.96; H, 2.36; N, 13.88. $^1$H NMR (300 MHz, CDCl$_3$) δ 7.75 (d, 2H, J=8.6 Hz), 7.42 (d, 2H, J=8.6 Hz), 7.11 (s, 1H), 4.80 (q, 4H, J=8.2 Hz), 3.39 (s, 3H).

Example 10

Preparation of N-[4,6-bis(2,2,2-trifluoroethoxy)pyrimidin-2-yl]-N-methyl-N'-[4-(trifluoromethoxy)phenyl]urea (10)

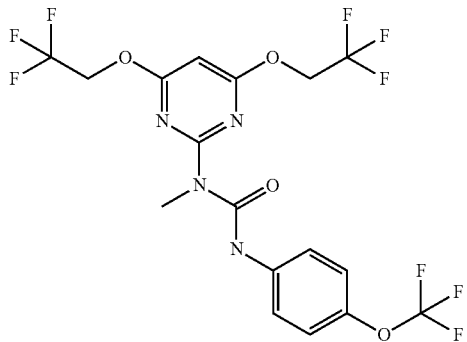 [SMILES: CN(C(=O)Nc1ccc(OC(F)(F)F)cc1)c1nc(OCC(F)(F)F)cc(OCC(F)(F)F)n1]

To a solution of urea 3 (469 mg, 0.95 mmol) in anhydrous DMF (5 mL) was added NaH (46 mg, 1.15 mmol, 60% dispersion in mineral oil) and this mixture was stirred for 30 min at which time methyl iodide (81 µL, 1.24 mmol) was added. The reaction was stirred overnight (ca. 15 hours) at which time the reaction was judged complete (TLC and LCMS). The reaction was quenched by addition of EtOAc and 1N HCl. The separated organic layer was washed with brine and dried over MgSO$_4$. The concentrated filtrate was purified by chromatography (silica, 15 to 30% EtOAc/hexane) to afford 10 as a white solid (145 mg, 30% yield): m.p. 123-125° C.; $^1$H NMR (CDCl$_3$) δ 11.42 (br s, 1H), 7.52 (d, 2H, J=9.1 Hz), 7.22 (d, 2H, J=8.2 Hz), 6.05 (s, 1H), 4.79 (q, 4H, J=7.9 Hz), 3.60 (s, 3H); ESI/MS 509 (M+H), 507 (M−H).

Example 11

Preparation of N-[4,6-bis(2,2,2-trifluoroethoxy)pyrimidin-2-yl]-N,N'-dimethyl-N'-[4-(trifluoromethoxy)phenyl]urea (11)

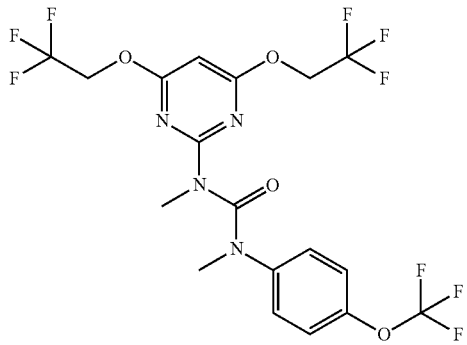 [SMILES: CN(C(=O)N(C)c1nc(OCC(F)(F)F)cc(OCC(F)(F)F)n1)c1ccc(OC(F)(F)F)cc1]

To a solution of urea 3 (975 mg, 1.97 mmol) in DMF (5 mL) was added NaH (200 mg, 5.0 mmol, 60% dispersion in mineral oil) and the resulting mixture was stirred for 30 minutes at which time methyl iodide (337 µL, 5.4 mmol) was added. The reaction was stirred 2 h at which time it was judged complete (TLC). The reaction was quenched by addition of EtOAc and water. The separated organic layer was washed with brine (3×) and then dried over MgSO$_4$. The concentrated filtrate was purified by chromatography (silica, 25-30% EtOAc/hexane) to afford bis-methyl urea 11 as a heavy oil (722 mg, 71% yield): $^1$H NMR (CDCl$_3$) δ 7.21-7.13 (m 4H), 5.75 (s, 1H), 4.71 (q, 4H, J=8.3 Hz), 3.41 (s, 3H), 3.17 (s, 3H); ESI/MS 523 (M+H).

Example 12

Preparation of N-Benzyloxymethyl-N-[4,6-bis-(2,2,2-trifluoroethoxy)pyrimidin-2-yl]-N'-[(4-trifluoromethyl)phenyl]urea (19)

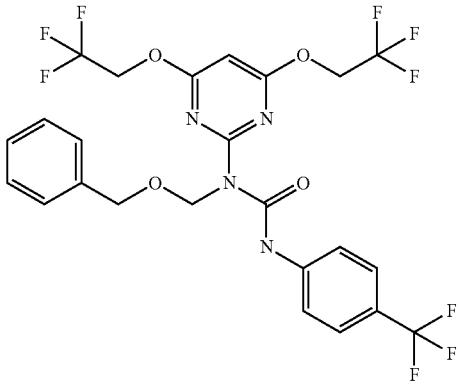

To a solution of urea 1 (2.00 g, 4.18 mmol) in anhydrous DMF (20 mL) at ambient temperature was added NaH (167 mg, 4.2 mmol, 60% dispersion in mineral oil). After stirring for 20 min a solution of benzyloxymethyl chloride (1.09 g, 60% technical solution) in anhydrous DMF (2 mL) was added over 2 min. After 2 h the reaction was judged complete (TLC). The reaction was quenched by the addition of water and EtOAc. The separated organic layer was washed with water (3×), once with brine, and was dried over MgSO$_4$. The concentrated filtrate was purified by chromatography (silica, 10-20% EtOAc/hexane) to afford 19 as a white solid (2.29 g, 91% yield): m.p. 105-107° C.; $^1$H NMR (CDCl$_3$) δ 11.25 (br s, 1H), 7.61 (app s, 4H), 7.30 (5H), 6.07 (s, 1H), 5.81 (s, 2H), 4.73 (s, 2H), 4.68 (q, 4H, J=8.0 Hz); ESI/MS 590 (M+H), 597 (M−H).

Example 13

Preparation of N-Benzyloxymethyl-N'-[4,6-bis(2,2,2-trifluoroethoxy)pyrimidin-2-yl]-N'-ethoxymethyl-N'-[4-(trifluoromethyl)phenyl]urea (33)

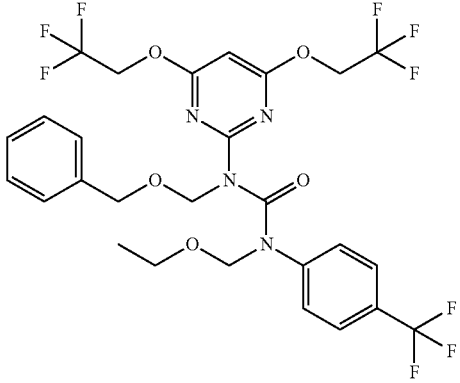 [SMILES: CCOCN(C(=O)N(COCc1ccccc1)c1nc(OCC(F)(F)F)cc(OCC(F)(F)F)n1)c1ccc(C(F)(F)F)cc1]

To a solution of 19 (10.03 g, 16.7 mmol) in anhydrous DMF (100 mL), with an internal temperature of ≤−10° C., was added NaH (0.74 g, 18.4 mmol, 60% dispersion in mineral oil) over 5 min. To the resulting clear yellow solution, after stirring for 30 min, was added a solution of chloromethyl ethyl ether (1.85 mL, 20 mmol) in anhydrous DMF (6.0 mL) over 12 min via syringe pump. After stirring for 2.5 h at −10° C., analysis of a quenched aliquot showed the reaction was complete (TLC and LCMS). The reaction mixture was poured into a mixture of EtOAc, dilute HCl, and ice. After shaking the layers were separated. The organic layer was washed with water and the aqueous layer was back extracted with EtOAc. The combined organic layers were washed with water (2×), brine, and dried over MgSO$_4$. The filtered concentrate was purified by chromatography (silica, 15-20% EtOAc/hex) to afford 33 as a white solid (8.0 g, 73% yield, 95% purity): m.p. 62-65° C.; $^1$H NMR (CDCl$_3$) δ 7.4-7.29 (m, 9H), 5.74 (s, 1H), 5.31 (s, 2H), 5.22 (s, 2H), 4.72 (s, 2H), 4.61 (q, 4H, J=8.5 Hz), 3.75 (q, 2H, J=7.1 Hz), 1.25 (t, 3H, J=7.2 Hz); ESI/MS 612 (M−EtOH), 716 (M+CH$_3$CO$_2$H).

Example 14

Preparation of N'-[4,6-Bis(2,2,2-trifluoroethoxy)pyrimidin-2-yl]-N-ethoxymethyl-N-4-trifluoromethylphenyl)urea (34)

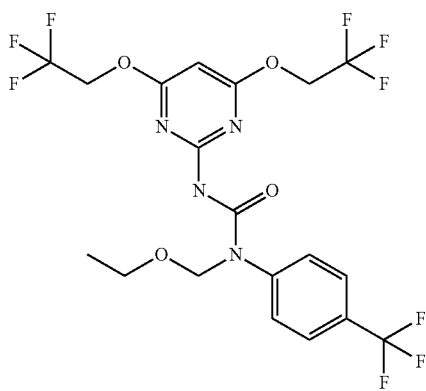 [SMILES: CCOCN(C(=O)Nc1nc(OCC(F)(F)F)cc(OCC(F)(F)F)n1)c1ccc(C(F)(F)F)cc1]

To a heavy walled hydrogenation jar containing a suspension of palladium hydroxide on carbon (2.1 g, 20%, 60% moisture, 10% w/w) in EtOAc (50 mL) at ambient temperature was added a solution of 33 (21.2 g, 32.3 mmol) in MeOH/EtOAc (150/150 mL). After the addition was complete the dead space atmosphere was reduced in vacuo then backfilled with nitrogen (3×). Next, reduction of pressure was followed by charging the flask with 30 psi hydrogen. The reaction was allowed to stir for 2.5 h at which point the reaction was judged complete (TLC). The reaction mixture was filtered under reduced pressure over Celite and concentrated to an oil which was determined to be the hydroxymethyl compound by $^1$H NMR analysis. The oil was purified by column chromatography (silica, hexanes/EtOAc). The early eluting fractions (4.3 g) were again subjected to purification by column chromatography (silica, hexanes/EtOAc) to afford highly pure product (1.7 g). The middle eluting fractions (judged to be 88% pure by LCMS) were recrystallized using a 5% CH$_2$Cl$_2$/hexanes system to afford highly pure 34 as a white solid (11.8 g total, 68% yield): m.p. 65-70° C.; $^1$H NMR (CDCl$_3$) δ 7.75 (d, 2H, J=8.3 Hz), 7.61 (br s, 1H), 7.52 (d, 2H, J=8.3 Hz), 6.01 (s, 1H), 5.19 (s, 2H), 4.75 (q, 4H, J=16.8, 8.2 Hz), 3.72 (q, 2H, J=14.2, 7.1 Hz), 1.31 (t, 3H, J=7.0 Hz); ESI/MS 535 (M−H).

Example 15

Preparation of N'-[4,6-bis(2,2,2-trifluoroethoxy)pyrimidin-2-yl]-N-(4-chlorophenyl)-N-methoxyurea (65)

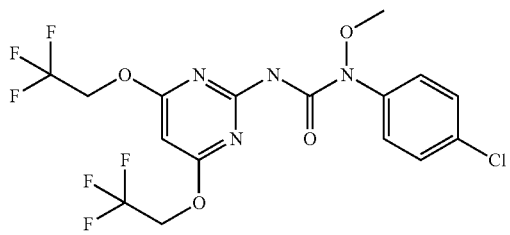 [SMILES: CON(C(=O)Nc1nc(OCC(F)(F)F)cc(OCC(F)(F)F)n1)c1ccc(Cl)cc1]

A. Preparation of N'-[4,6-bis(2,2,2-trifluoroethoxy)pyrimidin-2-yl]-N-(4-chlorophenyl)-N-hydroxyurea (64)

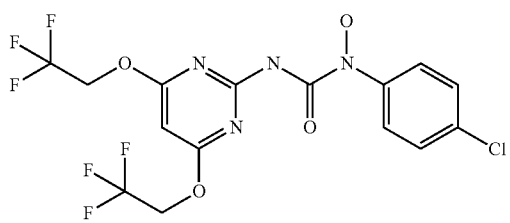 [SMILES: O=C(Nc1nc(OCC(F)(F)F)cc(OCC(F)(F)F)n1)N(O)c1ccc(Cl)cc1]

To a solution of 4-chloro-N-hydroxyaniline (0.423 g, 2.95 mmol (prepared according to the procedure of Rondestwedt Jr., C. S. and Johnson, T. A. *Synthesis* 1977, p 850-851) in THF (10 mL) was added the 2-isocyanato-4,6-bis(2,2,2-trifluoroethoxy)pyrimidine (2.0 g, 6.3 mmol) in THF (10 mL) and the mixture stirred at room temperature for 12 h. The mixture was concentrated in vacuo to give a brown solid. This solid was purified by reverse phase column chromatography (CH$_3$CN/H$_2$O) to afford 64 as a dark brown gum (448 mg, 36% yield): ESI/MS 461 (M+H), 459 (M−H); $^1$H NMR (DMSO-d$_6$): δ 11.04 (S, 1H, 9.51 (S, 1H), 7.63 (d, 2H, J=6.6 Hz), 7.41 (d, 2H, J=6.6 Hz), 6.30 (s, 1H), 5.05 (m, 4H).

B. Preparation of N'-[4,6-bis(2,2,2-trifluoroethoxy)pyrimidin-2-yl]-N-(4-chlorophenyl)-N-methoxyurea (65)

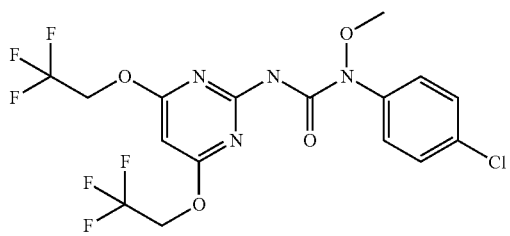 [SMILES: CON(C(=O)Nc1nc(OCC(F)(F)F)cc(OCC(F)(F)F)n1)c1ccc(Cl)cc1]

A dry round bottom flask was charged with the N-hydroxy substrate 65 (100 mg, 0.217 mmol) and anhydrous THF (2 mL). The mixture was cooled to 0° C., sodium hydride (0.23 mmol, 9.13 mg, 60% dispersion in mineral oil) was added in one portion, and the resulting mixture stirred for 10 min. To the mixture was added MeI (59 mg, 0.42 mmol). After stirring at 0° C. for 3 h, the reaction is diluted with ethyl acetate (50 mL) and water (10 mL). The organic phase was separated, rinsed with brine, dried over Na$_2$SO$_4$, filtered and concentrated under vacuum on a rotary evaporator to give a brown solid. This solid was recrystallized (Et$_2$O/hexanes) to afford 65 as a brown solid (40 mg, 38%). The mother liquor was concentrated and purified by column chromatography (silica gel, hexanes/EtOAc) to give additional product (tan solid, 30 mg, 29% yield): m.p. 275-276° C.; $^1$H NMR (DMSO-d$_6$) δ 7.49 (m, 4H), 6.33 (s, 1H), 5.09 (m, 4H), 3.73 (s, 3H).

Example 16

Preparation of N'[3-fluoro-4,6-bis(2,2,2-trifluoroethoxy)pyridin-2-yl-]-N-methyl-N-(4-bromophenyl)urea (X)

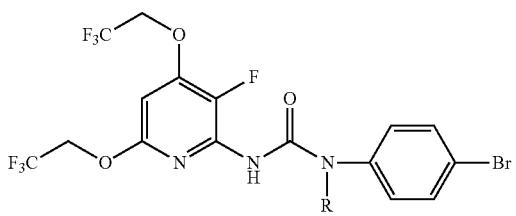

A. Preparation of 3-Chloro-2,5,6-trifluoro-4-(2,2,2-trifluoroethoxy)pyridine

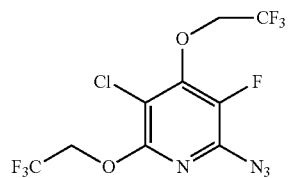

3-Chloro-2,4,5,6-tetrafluoropyridine (18.0 g, 97.0 mmol) was dissolved in anhydrous THF (100 mL) under an N$_2$ atmosphere and the resulting solution cooled to −78° C. To the cold solution was slowly added a solution of sodium 2,2,2-trifluoroethoxide (97 mmol), prepared from trifluoroethanol (7.1 mL, 97.0 mmol) and NaH (3.88 g, 97.0 mmol, 60% dispersion in mineral oil), in anhydrous THF (100 mL). The resulting mixture was slowly warmed to ambient temperature. After 18 h at ambient temperature a GC analysis indicates all the starting material was consumed. The volatiles were evaporated and the residue dissolved in CH$_2$Cl$_2$ (200 mL). The organics were washed with H$_2$O (3×100 mL), dried (MgSO$_4$), filtered and concentrated to give the crude product as a yellow oil. The yellow oil was distilled at reduced pressure to afford 3-chloro-2,5,6-trifluoro-4-(2,2,2-trifluoroethoxy)pyridine as a clear oil (16.3 g, 63% yield): by 48° C. (ca 0.2 mm Hg); $^1$H NMR (CDCl$_3$) δ 4.81-4.78 (dq, J=1.6, 7.7 Hz); GC-MS (EI, 70 eV) m/z (% relative intensity) 267 (33), 265 (100), 248 (5), 246 (16), 198 (22), 196 (60).

B. Preparation of 6-Azido-2,4-bis(2,2,2-trifluoroethoxy)-3-chloro-5-fluoropyridine

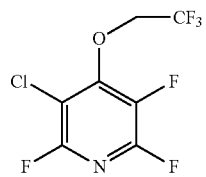 [SMILES: Fc1nc(F)c(Cl)c(OCC(F)(F)F)c1F]

3-Chloro-2,5,6-trifluoro-4-(2,2,2-trifluoroethoxy)pyridine (13.1 g, 49.3 mmol), was dissolved in anhydrous THF (50 mL). To the reaction mixture was added sodium azide (3.84 g, 59.2 mmol) and 18-crown-6 (1.0 g, 3.8 mmol). A GC analysis after 2 h indicates all the starting material had been consumed. The volatiles were evaporated and the residue mixed with EtOAc (200 mL). The organics were washed with H$_2$O (3×100 mL), dried (MgSO$_4$), filtered and concentrated to give the crude product as a brown oil. $^1$H NMR (CDCl$_3$) δ 4.74-4.67 (dq, J=1.4, 7.7 Hz); GC-MS (EI, 70 eV) m/z (% relative intensity) 290 (30), 288 (100). The crude material is used without further purification. The brown oil was dissolved in anhydrous THF (50 mL) under an N$_2$ atmosphere and the solution cooled to 0° C. To the cold solution was slowly added a solution of sodium 2,2,2-trifluoroethoxide (54 mmol), prepared by adding 2,2,2-trifluoroethanol (3.95 mL, 54 mmol) to a suspension of NaH (2.17 g, 54 mmol, 60% dispersion in mineral oil) in anhydrous THF (100 mL). After 18 h the volatiles were evaporated and the residue mixed this CH$_2$Cl$_2$ (200 mL). The organics were washed with H$_2$O (3×100 mL), dried (MgSO$_4$), filtered and concentrated to give the crude product as a brown oil. The oil was purified by column chromatography (SiO$_2$, hexane/EtOAc) to afford the product as a yellow crystalline solid (14.0 g, 77% yield): mp 52-54° C.; $^1$H NMR (CDCl$_3$) δ 4.83-4.75 (q, J=8.2 Hz, 2H), 4.70-4.62 (dq, J=1.1, 7.7 Hz, 2H); GC-MS (EI, 70 eV) m/z (% relative intensity) 370 (6), 368 (20), 273 (34), 271 (100), 190 (11), 188 (34).

C. Preparation of 2-Amino-fluoro-4,6-bis(2,2,2-trifluoroethoxy)pyridine

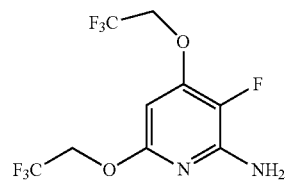

A 350 mL stainless steel pressure reactor equipped with a mechanical stirrer was charged with 6-azido-2,4-bis(2,2,2-trifluoroethoxy)-3-chloro-5-fluoropyridine (14.0 g, 38.0 mmol), EtOH (50 mL), and palladium on carbon (10%, 4.0 g). The reactor was sealed and pressurized with H$_2$ (500 psi). The pressurized reactor was heated to 100° C. After 18 h the pressurized reactor was cooled to ambient temperature. A GC analysis indicated all the starting material was consumed. The reaction was filtered and the volatiles evaporated to afford the crude product as a brown oil. The brown oil was purified by column chromatography (SiO$_2$, hexane/EtOAc) to afford the product as a brown crystalline solid (7.29 g, 62% yield): mp 43-45° C.; $^1$H NMR (CDCl$_3$) δ 5.84 (d, J=4.1 Hz, 1H), 5.85-4.56 (q, J=8.5, 2H), 4.49-4.37 (m, 4H); GC-MS (EI, 70 eV) m/z (% relative intensity) 308 (100), 289 (26), 239 (74).

D. Preparation of 4-Nitrophenyl-3-fluoro-4,6-bis(2,2,2-trifluoroethoxy)pyridin-2-ylcarbamate

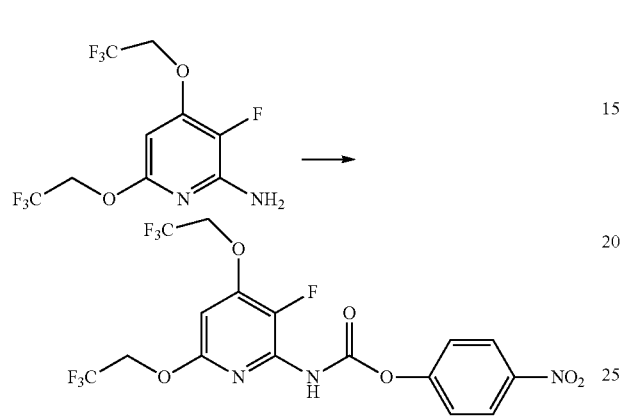

A solution of 2-amino-fluoro-4,6-bis(2,2,2-trifluoroethoxy)pyridine (1.32 g, 4.3 mmol) in CH$_2$Cl$_2$ (10 mL) was added to a solution of 4-nitrophenyl chloroformate (2.6 g, 13 mmol) in CH$_2$Cl$_2$ (10 mL). After 96 h the CH$_2$Cl$_2$ was evaporated and the residue mixed with hexanes (50 mL), stirred 4 h and filtered. The resulting white solid was mixed with Et$_2$O (50 mL), stirred 4 h, filtered, and allowed to air dry (ca 4 h) to afford the product as a white solid (1.74 g, 86% yield): mp 111-115; $^1$H NMR (CDCl$_3$) δ 8.32 (d, J=9.3 Hz, 2H) 7.43 (d, J=9.1 Hz, 2H) 7.24 (bs, 1H), 6.31 (d, J=4.7), 4.78-4.69 (q, J=8.2 Hz, 2H), 4.53-4.45 (q, J=7.8 Hz, 2H).

E. Preparation of N'[3-fluoro-4,6-bis(2,2,2-trifluoroethoxy)pyridin-2-yl-]-N-methyl-N-(4-bromophenyl)urea

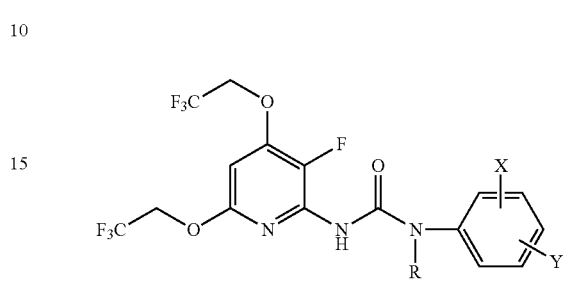

4-Nitrophenyl-3-fluoro-4,6-bis(2,2,2-trifluoroethoxy)pyridin-2-ylcarbamate (520 mg, 1.1 mmol) was dissolved in anhydrous THF (3 mL). To this solution was added N-methyl-4-bromoaniline (200 mg, 1.1 mmol). The reaction was allowed to stir for 12 d. The THF was evaporated and the crude material purified by reverse phase chromatography (HPLC grade CH$_3$CN and H$_2$O, both with 0.1% acetic acid) to afford the product as a tan solid (275 mg, 48% yield): mp 89-90° C.; $^1$H NMR (CDCl$_3$) δ 8.78 (s, 1H), 7.57 (d, J=8.8 Hz, 2H), 7.29 (d, J=8.8 Hz, 2H), 6.79 (d, J=4.7 Hz, 1H), 5.04-4.95 (q, J=8.8 Hz, 2H), 4.94-4.85 (q, J=9.1 Hz, 2H), 3.27 (s, 3H); ESI/MS 520, 522 (M+H), 518, 520 (M−H).

The compounds identified in Table 1 were prepared using the procedures illustrated in the foregoing examples.

TABLE 1

Insecticidal Compounds

| Compound Number | Molecular Structure | Melting Point (° C.) | Appearance | Mol Ion (M + H), (M − H) |
|---|---|---|---|---|
| 1 | 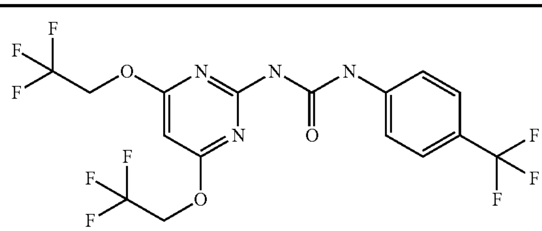 | 166-167 | white solid | (479), (477) |
| 2 | 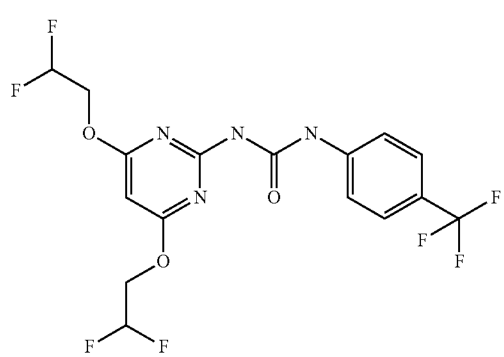 [SMILES: O=C(Nc1ccc(C(F)(F)F)cc1)Nc1nc(OCC(F)F)cc(OCC(F)F)n1] | 188-190 | white powder | (443), (440) |

TABLE 1-continued
| | | Insecticidal Compounds | | |
|---|---|---|---|---|
| Compound Number | Molecular Structure | Melting Point (° C.) | Appearance | Mol Ion (M + H), (M − H) |
| 3 | 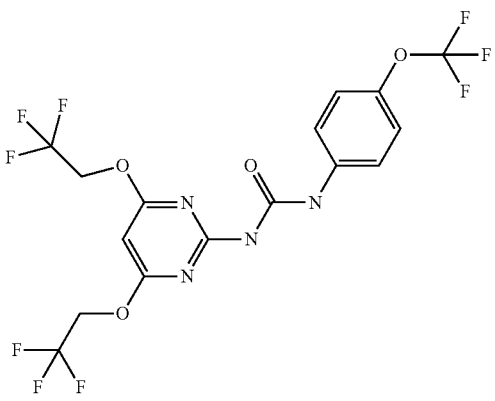 [SMILES: O=C(Nc1ccc(OC(F)(F)F)cc1)Nc1nc(OCC(F)(F)F)cc(OCC(F)(F)F)n1] | 167-168 | white solid | (495), (493) |
| 4 | 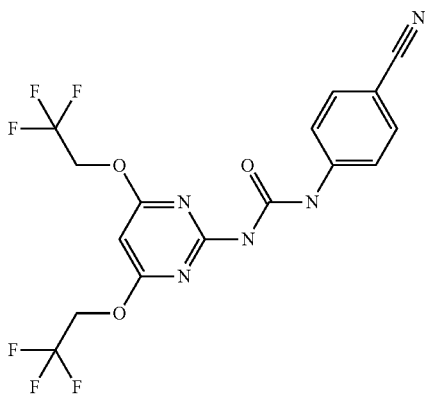 [SMILES: N#Cc1ccc(NC(=O)Nc2nc(OCC(F)(F)F)cc(OCC(F)(F)F)n2)cc1] | 252-253 | yellow solid | (436), (434) |
| 5 | 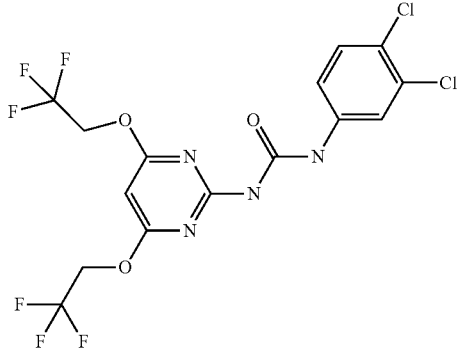 [SMILES: O=C(Nc1ccc(Cl)c(Cl)c1)Nc1nc(OCC(F)(F)F)cc(OCC(F)(F)F)n1] | 216-218 | tan solid | (479), (477) |

TABLE 1-continued

Insecticidal Compounds

| Compound Number | Molecular Structure | Melting Point (° C.) | Appearance | Mol Ion (M + H), (M − H) |
|---|---|---|---|---|
| 6 | 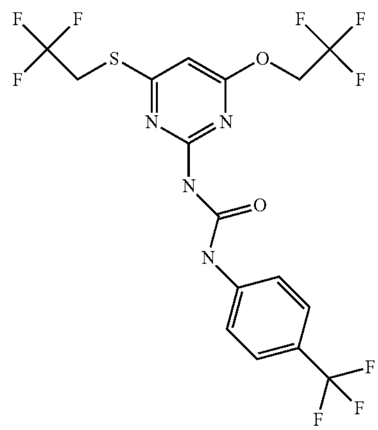 [SMILES: O=C(Nc1ccc(C(F)(F)F)cc1)Nc1nc(OCC(F)(F)F)cc(SCC(F)(F)F)n1] | 206-208 | white solid | (495), (493) |
| 7 | 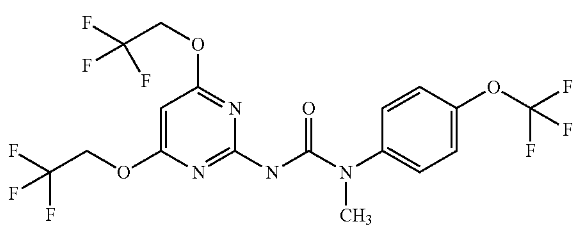 [SMILES: CN(C(=O)Nc1nc(OCC(F)(F)F)cc(OCC(F)(F)F)n1)c1ccc(OC(F)(F)F)cc1] | 100-102 | white solid | (509), (507) |
| 8 | 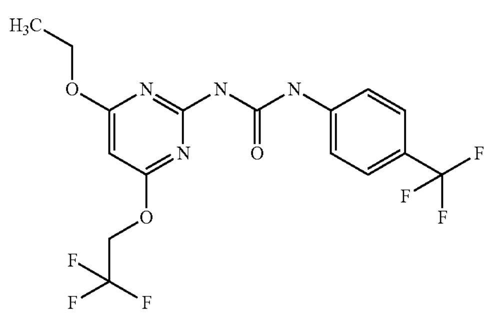 [SMILES: CCOc1cc(OCC(F)(F)F)nc(NC(=O)Nc2ccc(C(F)(F)F)cc2)n1] | 206-210 | light pink solid (71% pure by $^1$H NMR) | (426), (423) |
| 9 | 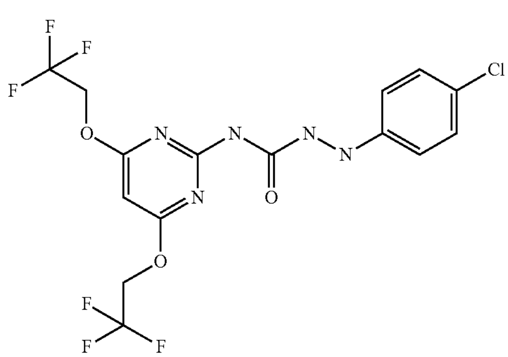 [SMILES: O=C(NNc1ccc(Cl)cc1)Nc1nc(OCC(F)(F)F)cc(OCC(F)(F)F)n1] | — | orange oil | (461), (457) |

TABLE 1-continued

Insecticidal Compounds

| Compound Number | Molecular Structure | Melting Point (° C.) | Appearance | Mol Ion (M + H), (M − H) |
|---|---|---|---|---|
| 10 | 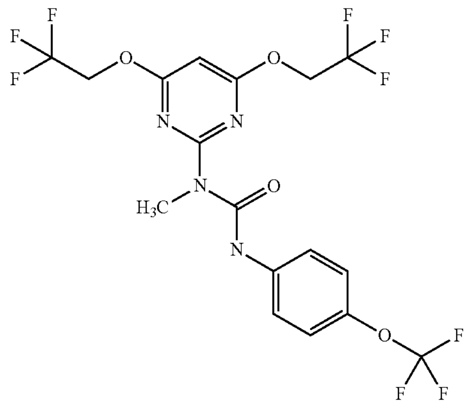 [SMILES: CN(C(=O)Nc1ccc(OC(F)(F)F)cc1)c1nc(OCC(F)(F)F)cc(OCC(F)(F)F)n1] | 123-125 | white solid | (509), (507) |
| 11 | 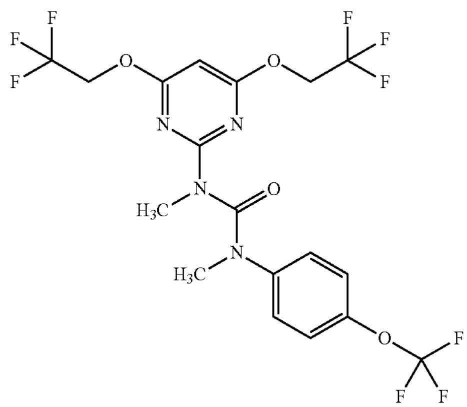 [SMILES: CN(C(=O)N(C)c1nc(OCC(F)(F)F)cc(OCC(F)(F)F)n1)c1ccc(OC(F)(F)F)cc1] | — | clear oil | (523, M + 1) |
| 12 | 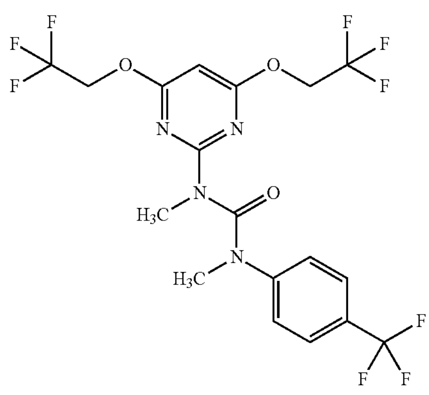 [SMILES: CN(C(=O)N(C)c1nc(OCC(F)(F)F)cc(OCC(F)(F)F)n1)c1ccc(C(F)(F)F)cc1] | 80-82 | white solid | (507, M + 1) |
| 13 | 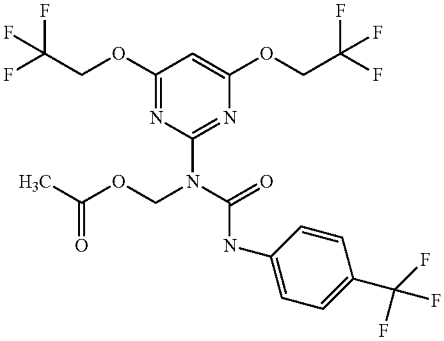 [SMILES: CC(=O)OCN(C(=O)Nc1ccc(C(F)(F)F)cc1)c1nc(OCC(F)(F)F)cc(OCC(F)(F)F)n1] | 108-110 | white solid | (549, M − 1) |

TABLE 1-continued

Insecticidal Compounds

| Compound Number | Molecular Structure | Melting Point (° C.) | Appearance | Mol Ion (M + H), (M − H) |
|---|---|---|---|---|
| 14 | 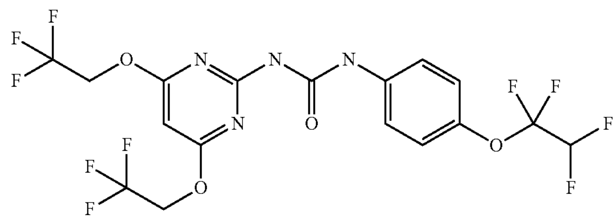 [SMILES: O=C(Nc1ccc(OC(F)(F)C(F)F)cc1)Nc1nc(OCC(F)(F)F)cc(OCC(F)(F)F)n1] | 184-187 | white solid | (527), (525) |
| 15 | 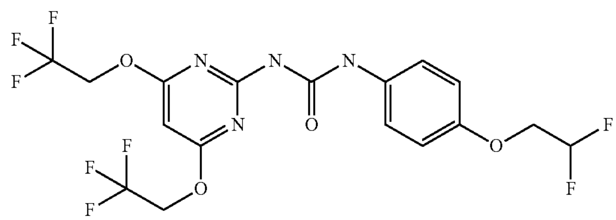 [SMILES: O=C(Nc1ccc(OCC(F)F)cc1)Nc1nc(OCC(F)(F)F)cc(OCC(F)(F)F)n1] | 190-191 | white solid | (491), (489) |
| 16 | 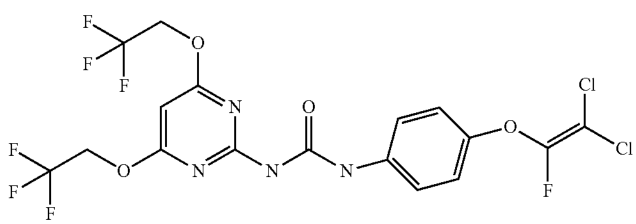 [SMILES: O=C(Nc1ccc(OC(F)=C(Cl)Cl)cc1)Nc1nc(OCC(F)(F)F)cc(OCC(F)(F)F)n1] | 167-168 | white solid | (539), (538) |
| 17 | 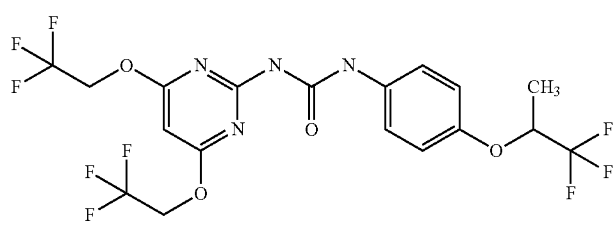 [SMILES: CC(Oc1ccc(NC(=O)Nc2nc(OCC(F)(F)F)cc(OCC(F)(F)F)n2)cc1)C(F)(F)F] | 191.5-192.5 | white solid | (523), (NA) |
| 18 | 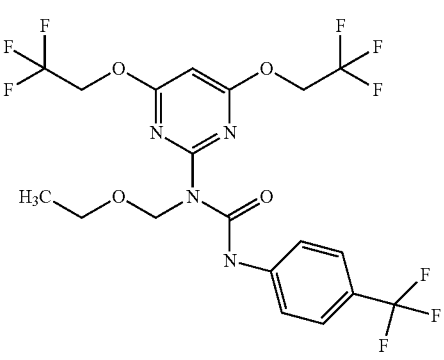 [SMILES: CCOCN(C(=O)Nc1ccc(C(F)(F)F)cc1)c1nc(OCC(F)(F)F)cc(OCC(F)(F)F)n1] | 90-92 | white solid | (537), (535) |

TABLE 1-continued

Insecticidal Compounds

| Compound Number | Molecular Structure | Melting Point (° C.) | Appearance | Mol Ion (M + H), (M − H) |
|---|---|---|---|---|
| 19 | 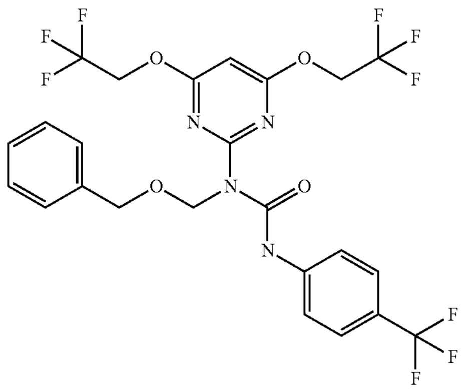 [SMILES: O=C(Nc1ccc(C(F)(F)F)cc1)N(COCc1ccccc1)c1nc(OCC(F)(F)F)cc(OCC(F)(F)F)n1] | 105-107 | white solid | (599), (597) |
| 20 | 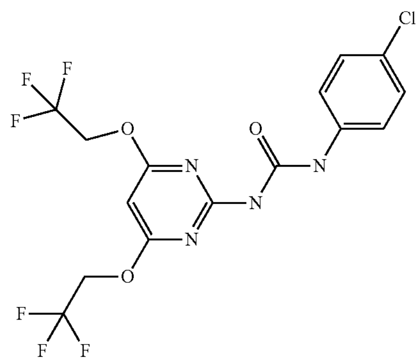 [SMILES: O=C(Nc1ccc(Cl)cc1)Nc1nc(OCC(F)(F)F)cc(OCC(F)(F)F)n1] | NA | white solid | (445), (443) |
| 21 | 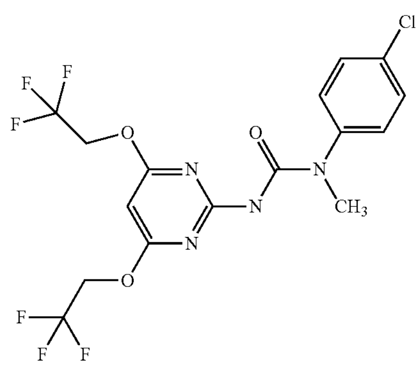 [SMILES: CN(C(=O)Nc1nc(OCC(F)(F)F)cc(OCC(F)(F)F)n1)c1ccc(Cl)cc1] | NA | white solid | (459), (457) |
| 22 | 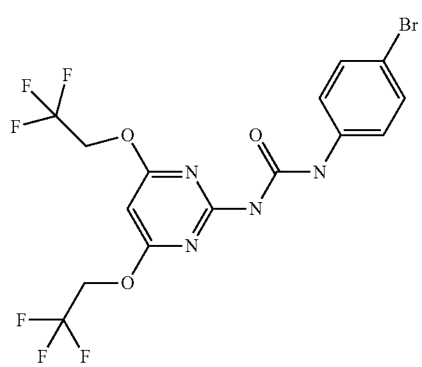 [SMILES: O=C(Nc1ccc(Br)cc1)Nc1nc(OCC(F)(F)F)cc(OCC(F)(F)F)n1] | NA | white solid | (491, 492), (490, 489) |

TABLE 1-continued
Insecticidal Compounds
| Compound Number | Molecular Structure | Melting Point (° C.) | Appearance | Mol Ion (M + H), (M − H) |
|---|---|---|---|---|
| 23 | 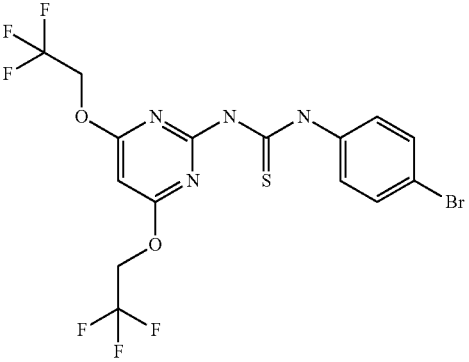 [SMILES: FC(F)(F)COc1cc(OCC(F)(F)F)nc(NC(=S)Nc2ccc(Br)cc2)n1] | 195-201 | white solid | (508), (504) |
| 24 | 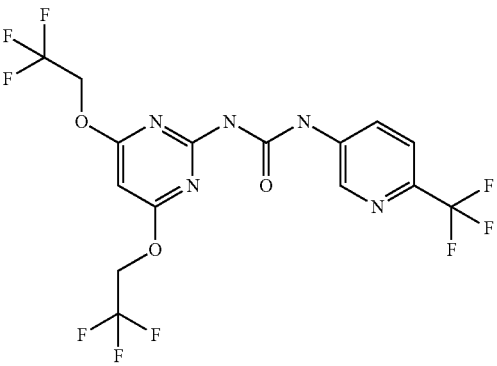 [SMILES: O=C(Nc1ccc(C(F)(F)F)nc1)Nc1nc(OCC(F)(F)F)cc(OCC(F)(F)F)n1] | 159-162 | white solid | (480), (478) |
| 25 | 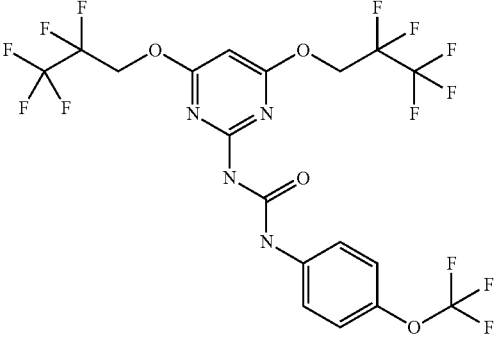 [SMILES: O=C(Nc1ccc(OC(F)(F)F)cc1)Nc1nc(OCC(F)(F)C(F)(F)F)cc(OCC(F)(F)C(F)(F)F)n1] | 174-175 | white solid | (595), (594) |
| 26 | 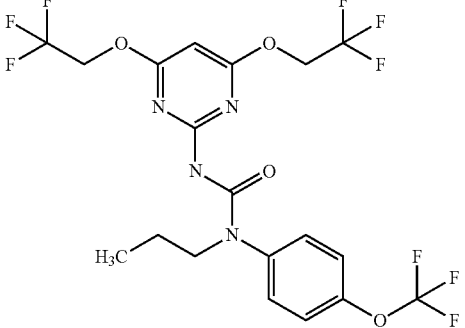 | 105-106 | tan solid | (537), (535) |

TABLE 1-continued

Insecticidal Compounds

| Compound Number | Molecular Structure | Melting Point (° C.) | Appearance | Mol Ion (M + H), (M − H) |
|---|---|---|---|---|
| 27 | 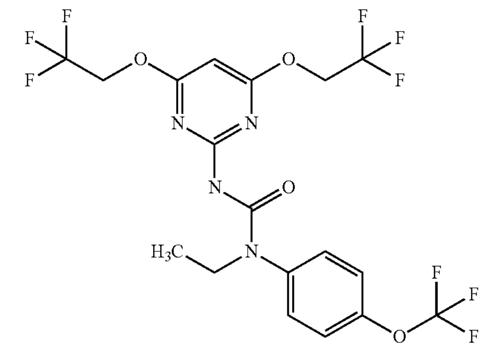 [SMILES: CCN(C(=O)Nc1nc(OCC(F)(F)F)cc(OCC(F)(F)F)n1)c1ccc(OC(F)(F)F)cc1] | 104-106 | tan solid | (523), (521) |
| 28 | 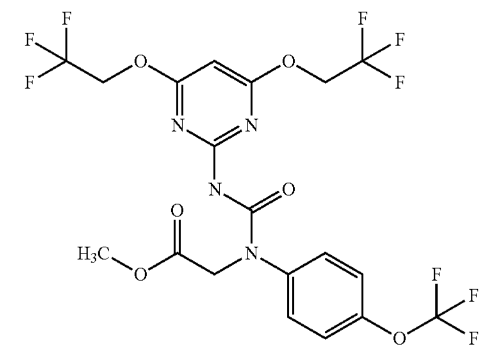 [SMILES: COC(=O)CN(C(=O)Nc1nc(OCC(F)(F)F)cc(OCC(F)(F)F)n1)c1ccc(OC(F)(F)F)cc1] | 147-149 | white crystals | (567), (565) |
| 29 | 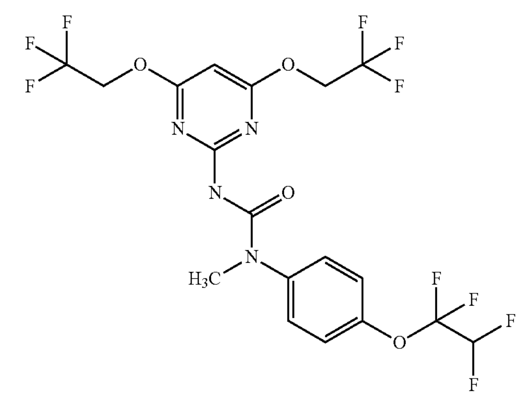 [SMILES: CN(C(=O)Nc1nc(OCC(F)(F)F)cc(OCC(F)(F)F)n1)c1ccc(OC(F)(F)C(F)F)cc1] | 105-108 | white needles | (541), (539) |
| 30 | 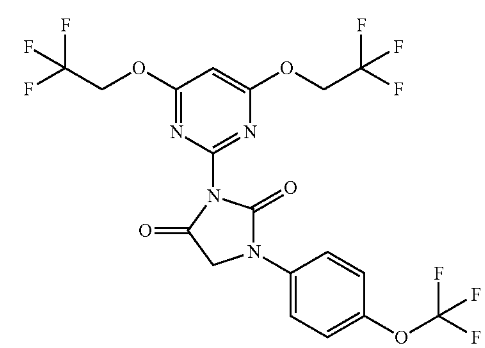 [SMILES: O=C1CN(c2ccc(OC(F)(F)F)cc2)C(=O)N1c1nc(OCC(F)(F)F)cc(OCC(F)(F)F)n1] | 100-102 | white solid | (535), (533) |

TABLE 1-continued

Insecticidal Compounds

| Compound Number | Molecular Structure | Melting Point (° C.) | Appearance | Mol Ion (M + H), (M − H) |
|---|---|---|---|---|
| 31 | 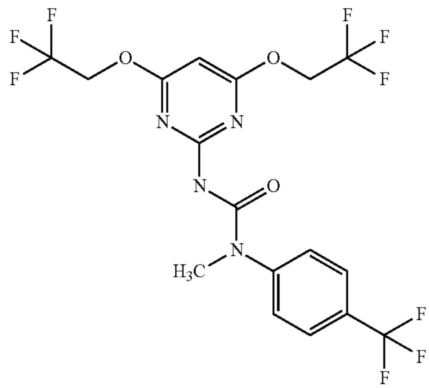 [SMILES: CN(C(=O)Nc1nc(OCC(F)(F)F)cc(OCC(F)(F)F)n1)c1ccc(C(F)(F)F)cc1] | 65-67 | white solid | (493), (491) |
| 32 | 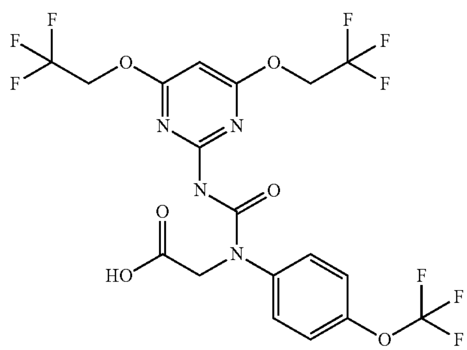 [SMILES: O=C(O)CN(C(=O)Nc1nc(OCC(F)(F)F)cc(OCC(F)(F)F)n1)c1ccc(OC(F)(F)F)cc1] | 149-151 | white powder | (553), (551) |
| 33 | 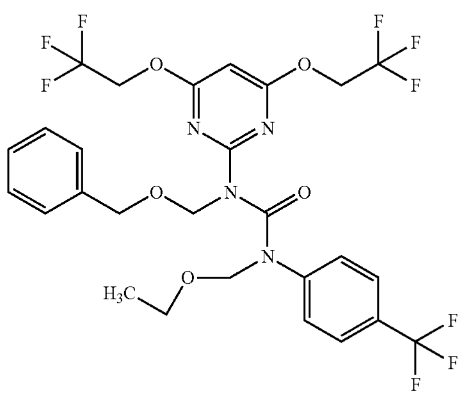 | 62-65 | white powder | (612, M − EtOH), (716 M + HOAc). |
| 34 | 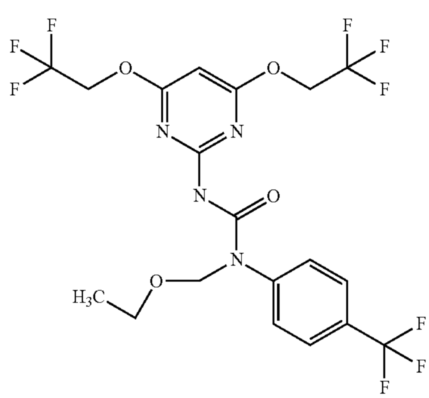 [SMILES: CCOCN(C(=O)Nc1nc(OCC(F)(F)F)cc(OCC(F)(F)F)n1)c1ccc(C(F)(F)F)cc1] | 65-70 | white solid | (537), (535) |

TABLE 1-continued

| Compound Number | Molecular Structure | Melting Point (° C.) | Appearance | Mol Ion (M + H), (M − H) |
|---|---|---|---|---|
| 35 | 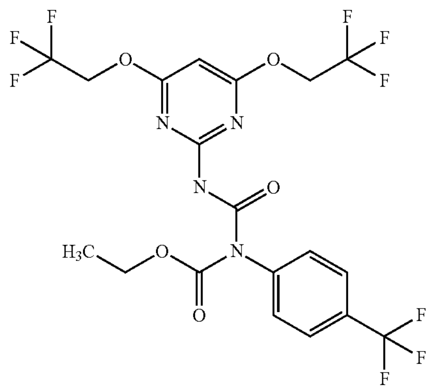 [SMILES: CCOC(=O)N(C(=O)Nc1nc(OCC(F)(F)F)cc(OCC(F)(F)F)n1)c1ccc(C(F)(F)F)cc1] | 115-118 | white fluffy solid | (551), (NA) |
| 36 | 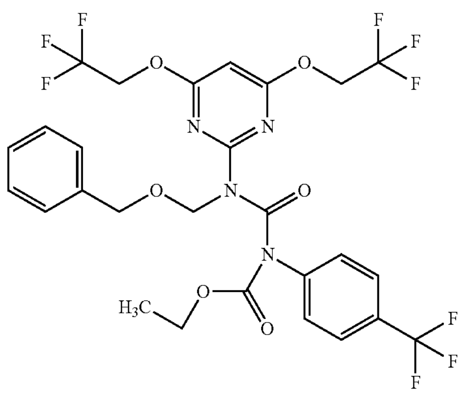 [SMILES: CCOC(=O)N(C(=O)N(COCc1ccccc1)c1nc(OCC(F)(F)F)cc(OCC(F)(F)F)n1)c1ccc(C(F)(F)F)cc1] | — | clear oil | (564, M − BnOH) |
| 37 | 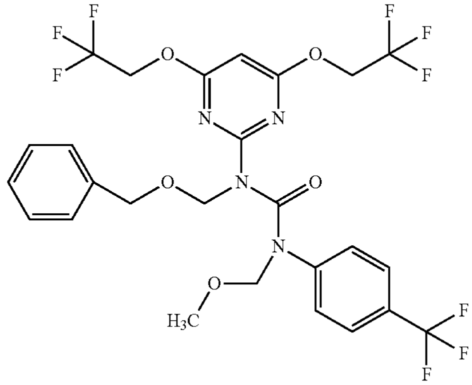 [SMILES: COCN(C(=O)N(COCc1ccccc1)c1nc(OCC(F)(F)F)cc(OCC(F)(F)F)n1)c1ccc(C(F)(F)F)cc1] | 75-80 | white solid | (701, M + AcOH − 1) |

TABLE 1-continued

| Insecticidal Compounds | | | | |
|---|---|---|---|---|
| Compound Number | Molecular Structure | Melting Point (° C.) | Appearance | Mol Ion (M + H), (M − H) |
| 38 | | 80-85 | white solid | (551), (549) |
| 39 | | 62-65 | white solid | (523), (521) |
| 40 | | 132-133 | white solid | (519, 517), (517, 515) |
| 41 | | 110-111 | white solid | (505, 503), (503, 501) |
| 42 | | 135-136 | white solid | (506, 504), (504, 502) |

TABLE 1-continued

Insecticidal Compounds

| Compound Number | Molecular Structure | Melting Point (° C.) | Appearance | Mol Ion (M + H), (M − H) |
|---|---|---|---|---|
| 43 | 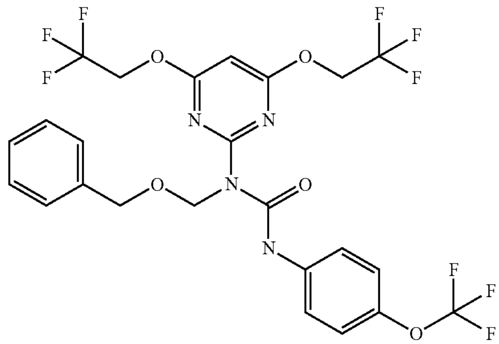 [SMILES: O=C(Nc1ccc(OC(F)(F)F)cc1)N(COCc1ccccc1)c1nc(OCC(F)(F)F)cc(OCC(F)(F)F)n1] | 82-85 | white solid | 615 (M + 1) |
| 44 | 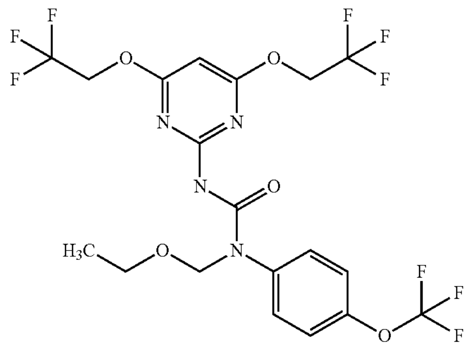 [SMILES: CCOCN(C(=O)Nc1nc(OCC(F)(F)F)cc(OCC(F)(F)F)n1)c1ccc(OC(F)(F)F)cc1] | 54-55 | white solid | (553), (551) |
| 45 | 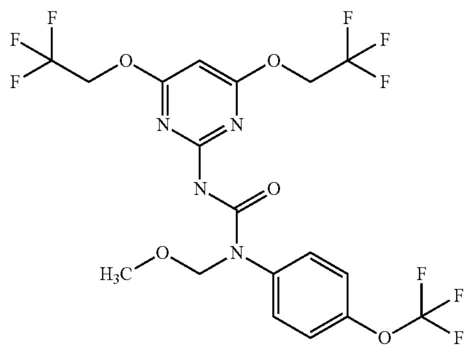 [SMILES: COCN(C(=O)Nc1nc(OCC(F)(F)F)cc(OCC(F)(F)F)n1)c1ccc(OC(F)(F)F)cc1] | 58-60 | white solid | (539), (537) |
| 46 | 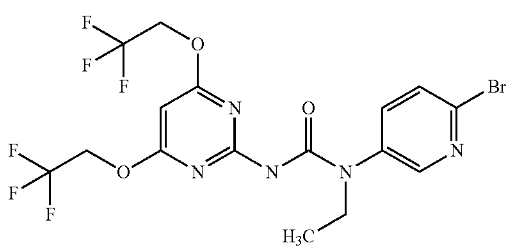 [SMILES: CCN(C(=O)Nc1nc(OCC(F)(F)F)cc(OCC(F)(F)F)n1)c1ccc(Br)nc1] | 73-74 | yellow glass | (520, 518), (518, 516) |
| 47 | 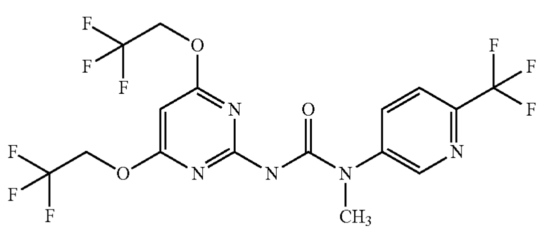 [SMILES: CN(C(=O)Nc1nc(OCC(F)(F)F)cc(OCC(F)(F)F)n1)c1ccc(C(F)(F)F)nc1] | 106-109 | yellow glass | (494), (492) |

TABLE 1-continued

Insecticidal Compounds

| Compound Number | Molecular Structure | Melting Point (° C.) | Appearance | Mol Ion (M + H), (M − H) |
|---|---|---|---|---|
| 48 | 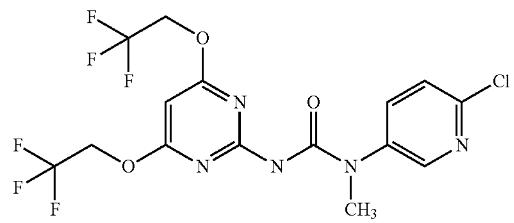 [SMILES: CN(C(=O)Nc1nc(OCC(F)(F)F)cc(OCC(F)(F)F)n1)c1ccc(Cl)nc1] | 132-134 | yellow glass | (460), (458) |
| 49 | 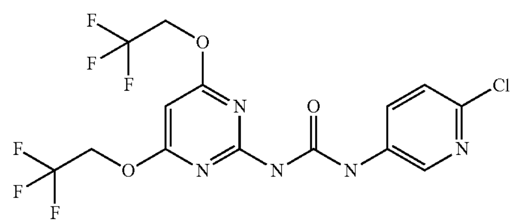 [SMILES: O=C(Nc1ccc(Cl)nc1)Nc1nc(OCC(F)(F)F)cc(OCC(F)(F)F)n1] | 158-160 | white solid | (446), (444) |
| 50 | 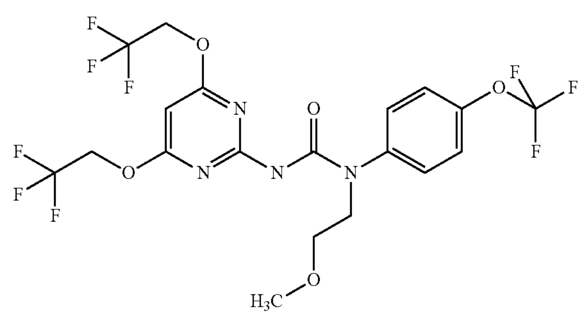 [SMILES: COCCN(C(=O)Nc1nc(OCC(F)(F)F)cc(OCC(F)(F)F)n1)c1ccc(OC(F)(F)F)cc1] | 87-88 | white glassy solid | (553), (551) |
| 51 | 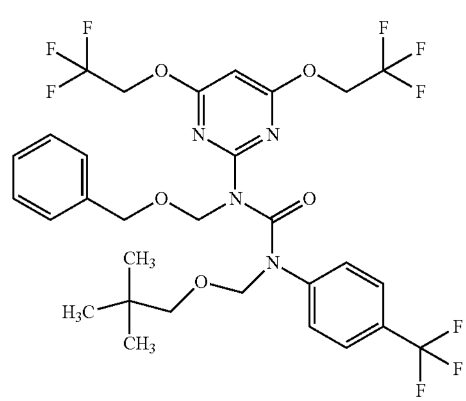 [SMILES: CC(C)(C)COCN(C(=O)N(COCc1ccccc1)c1nc(OCC(F)(F)F)cc(OCC(F)(F)F)n1)c1ccc(C(F)(F)F)cc1] | — | clear oil | (611, M − tBuCH$_2$OH) |

TABLE 1-continued

Insecticidal Compounds

| Compound Number | Molecular Structure | Melting Point (° C.) | Appearance | Mol Ion (M + H), (M − H) |
|---|---|---|---|---|
| 52 | 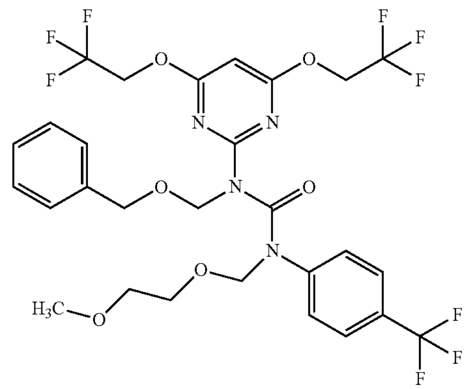 [SMILES: COCCOCN(C(=O)N(COCc1ccccc1)c1nc(OCC(F)(F)F)cc(OCC(F)(F)F)n1)c1ccc(C(F)(F)F)cc1] | — | clear oil | (611, M − CH₃OCH₂CH₂O) |
| 53 | 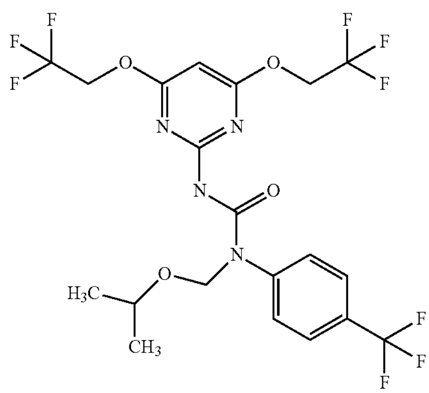 [SMILES: CC(C)OCN(C(=O)Nc1nc(OCC(F)(F)F)cc(OCC(F)(F)F)n1)c1ccc(C(F)(F)F)cc1] | 55-58 | white solid | (551), (549) |
| 54 | 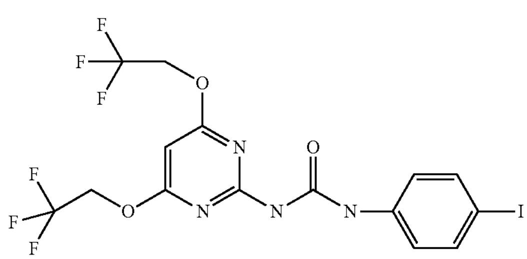 [SMILES: O=C(Nc1ccc(I)cc1)Nc1nc(OCC(F)(F)F)cc(OCC(F)(F)F)n1] | 200-202 | white solid | (537), (535) |
| 55 | 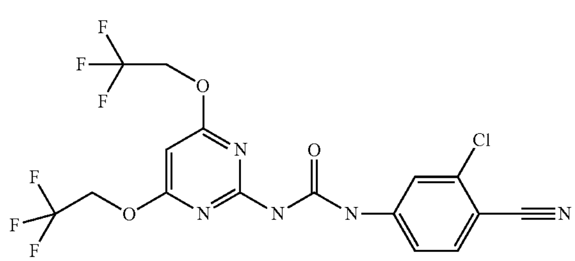 [SMILES: N#Cc1ccc(NC(=O)Nc2nc(OCC(F)(F)F)cc(OCC(F)(F)F)n2)cc1Cl] | 225-226 | tan solid | (470), (468) |

TABLE 1-continued

Insecticidal Compounds

| Compound Number | Molecular Structure | Melting Point (° C.) | Appearance | Mol Ion (M + H), (M − H) |
|---|---|---|---|---|
| 56 | 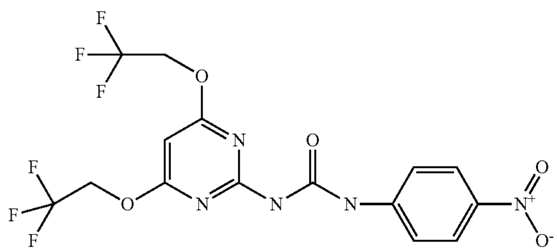 [SMILES: O=C(Nc1ccc([N+](=O)[O-])cc1)Nc1nc(OCC(F)(F)F)cc(OCC(F)(F)F)n1] | 233-234 | tan solid | (456), (454) |
| 57 | 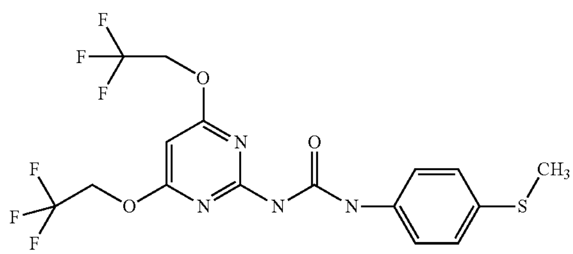 [SMILES: CSc1ccc(NC(=O)Nc2nc(OCC(F)(F)F)cc(OCC(F)(F)F)n2)cc1] | 217-218 | tan solid | (457), (455) |
| 58 | 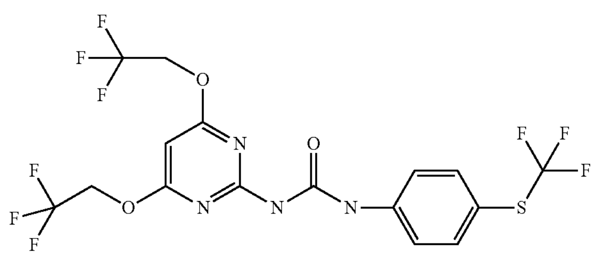 [SMILES: O=C(Nc1ccc(SC(F)(F)F)cc1)Nc1nc(OCC(F)(F)F)cc(OCC(F)(F)F)n1] | 195-197 | yellow solid | (511), (509) |
| 59 | 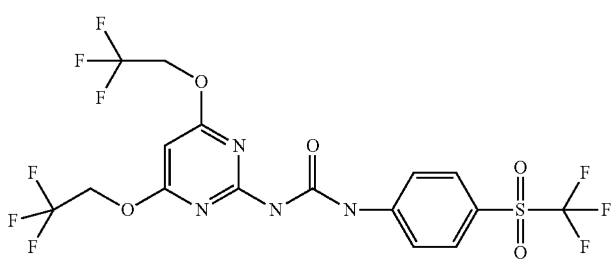 [SMILES: O=C(Nc1ccc(S(=O)(=O)C(F)(F)F)cc1)Nc1nc(OCC(F)(F)F)cc(OCC(F)(F)F)n1] | 225-227 | white solid | (543), (541) |
| 60 | 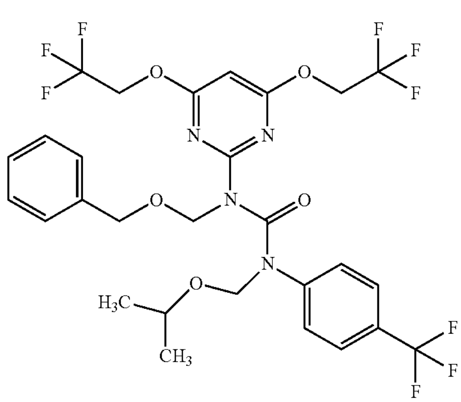 [SMILES: CC(C)OCN(C(=O)N(COCc1ccccc1)c1nc(OCC(F)(F)F)cc(OCC(F)(F)F)n1)c1ccc(C(F)(F)F)cc1] | — | clear oil | (611, M − tBuCH$_2$OH) |

TABLE 1-continued

Insecticidal Compounds

| Compound Number | Molecular Structure | Melting Point (° C.) | Appearance | Mol Ion (M + H), (M − H) |
|---|---|---|---|---|
| 61 | 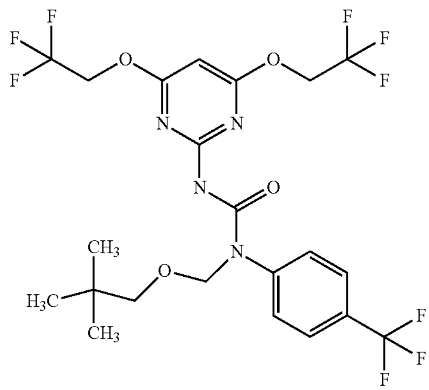 [SMILES: CC(C)(C)COCN(C(=O)Nc1nc(OCC(F)(F)F)cc(OCC(F)(F)F)n1)c1ccc(C(F)(F)F)cc1] | 113-115 | white solid | (579), (577) |
| 62 | 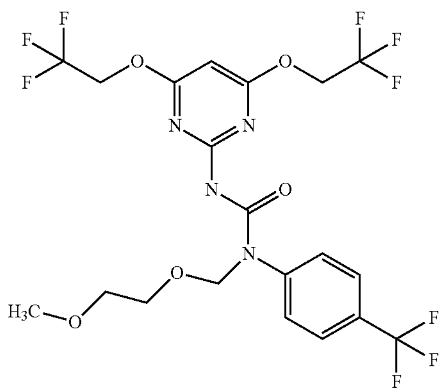 [SMILES: COCCOCN(C(=O)Nc1nc(OCC(F)(F)F)cc(OCC(F)(F)F)n1)c1ccc(C(F)(F)F)cc1] | — | clear oil | (567), (565) |
| 63 | 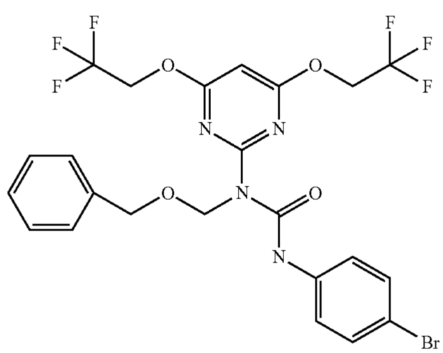 [SMILES: O=C(Nc1ccc(Br)cc1)N(COCc1ccccc1)c1nc(OCC(F)(F)F)cc(OCC(F)(F)F)n1] | 105-107 | white solid | (609, 611) |
| 64 | 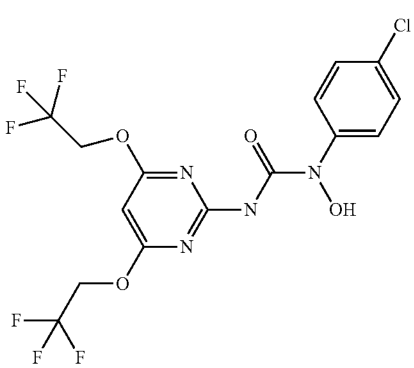 | NA | brown gum | (461), (459) |

TABLE 1-continued

Insecticidal Compounds

| Compound Number | Molecular Structure | Melting Point (° C.) | Appearance | Mol Ion (M + H), (M − H) |
|---|---|---|---|---|
| 65 | 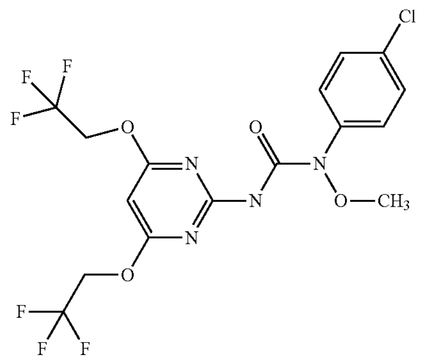 [SMILES: CON(C(=O)Nc1nc(OCC(F)(F)F)cc(OCC(F)(F)F)n1)c1ccc(Cl)cc1] | 275-276 | tan solid | (475), (473) |
| 66 | 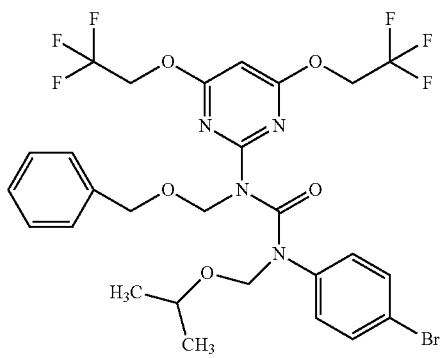 [SMILES: CC(C)OCN(C(=O)N(COCc1ccccc1)c1nc(OCC(F)(F)F)cc(OCC(F)(F)F)n1)c1ccc(Br)cc1] | — | clear oil | (621, 623, M − iPrOH), (NA) |
| 67 | 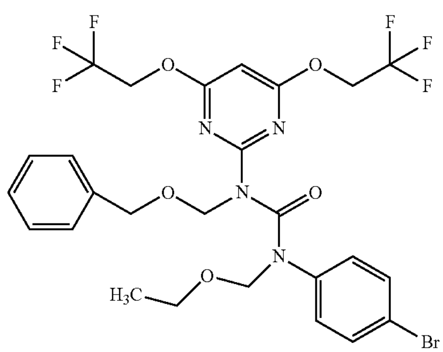 [SMILES: CCOCN(C(=O)N(COCc1ccccc1)c1nc(OCC(F)(F)F)cc(OCC(F)(F)F)n1)c1ccc(Br)cc1] | — | clear oil | (621, 623, M − EtOH), (NA) |
| 68 | 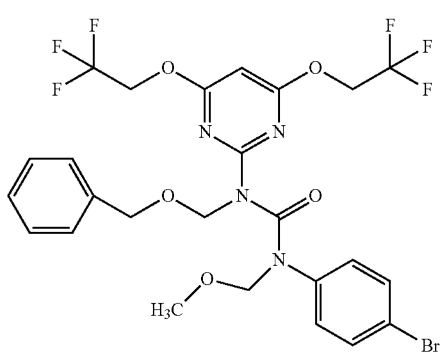 [SMILES: COCN(C(=O)N(COCc1ccccc1)c1nc(OCC(F)(F)F)cc(OCC(F)(F)F)n1)c1ccc(Br)cc1] | n/a | clear oil | (621, 623, M − MeOH), (NA) |

TABLE 1-continued

Insecticidal Compounds

| Compound Number | Molecular Structure | Melting Point (° C.) | Appearance | Mol Ion (M + H), (M − H) |
|---|---|---|---|---|
| 69 | 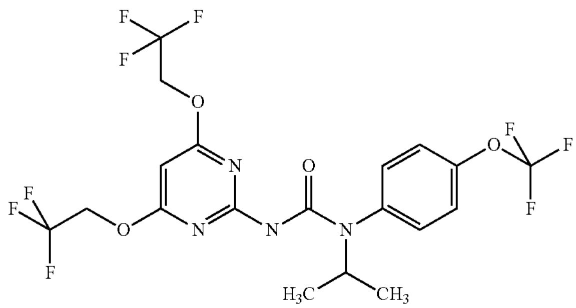 [SMILES: CC(C)N(C(=O)Nc1nc(OCC(F)(F)F)cc(OCC(F)(F)F)n1)c1ccc(OC(F)(F)F)cc1] | n/a | white solid | (537), (535) |
| 70 | 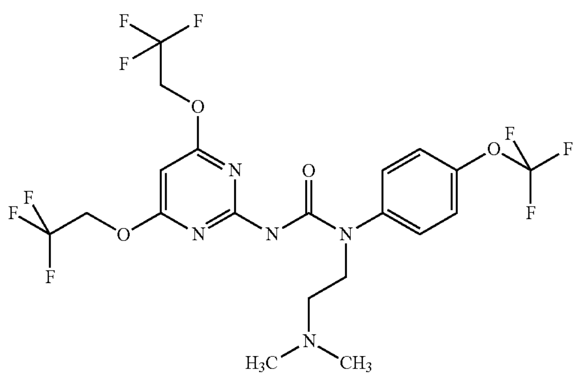 [SMILES: CN(C)CCN(C(=O)Nc1nc(OCC(F)(F)F)cc(OCC(F)(F)F)n1)c1ccc(OC(F)(F)F)cc1] | n/a | yellow oil | (566), (564) |
| 71 | 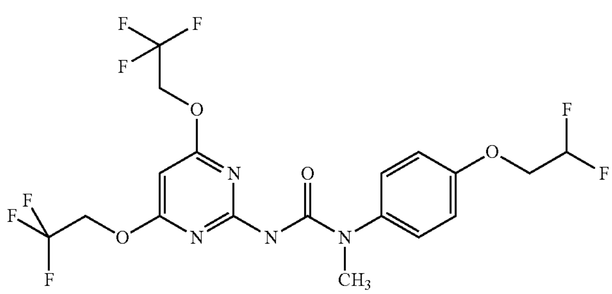 [SMILES: CN(C(=O)Nc1nc(OCC(F)(F)F)cc(OCC(F)(F)F)n1)c1ccc(OCC(F)F)cc1] | 126-127 | white solid | (505), (503) |
| 72 | 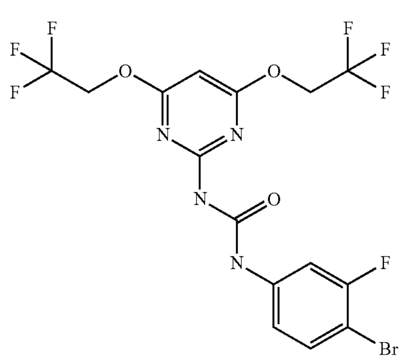 [SMILES: O=C(Nc1ccc(Br)c(F)c1)Nc1nc(OCC(F)(F)F)cc(OCC(F)(F)F)n1] | 210 | white solid | (507, 509), (505, 507) |

TABLE 1-continued
Insecticidal Compounds
| Compound Number | Molecular Structure | Melting Point (° C.) | Appearance | Mol Ion (M + H), (M − H) |
|---|---|---|---|---|
| 73 | 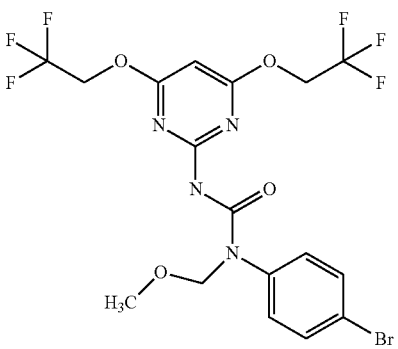 [SMILES: COCN(C(=O)Nc1nc(OCC(F)(F)F)cc(OCC(F)(F)F)n1)c1ccc(Br)cc1] | — | semi-solid | (531, 533, M − 1) |
| 74 | 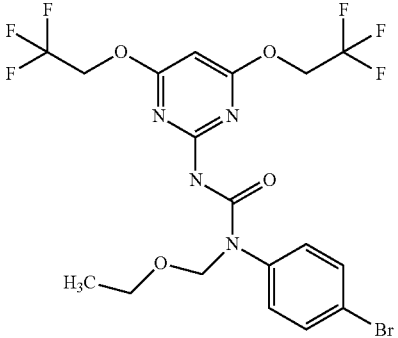 [SMILES: CCOCN(C(=O)Nc1nc(OCC(F)(F)F)cc(OCC(F)(F)F)n1)c1ccc(Br)cc1] | — | white wax | (547, 549), (545, 547) |
| 75 | 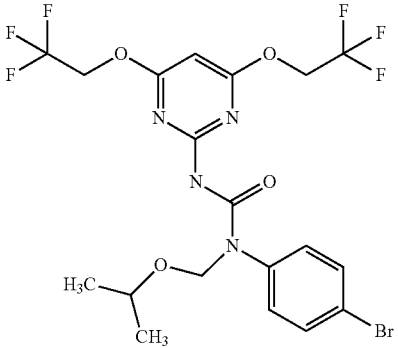 [SMILES: CC(C)OCN(C(=O)Nc1nc(OCC(F)(F)F)cc(OCC(F)(F)F)n1)c1ccc(Br)cc1] | — | clear oil | (561, 563), (559, 561) |
| 76 | 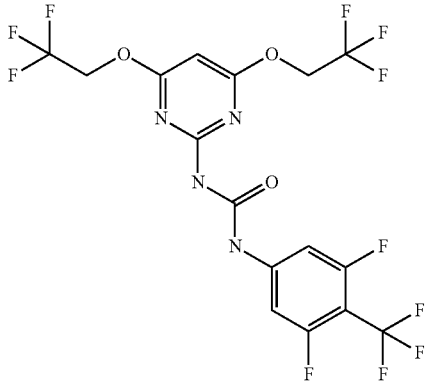 [SMILES: O=C(Nc1cc(F)c(C(F)(F)F)c(F)c1)Nc1nc(OCC(F)(F)F)cc(OCC(F)(F)F)n1] | 172-174 | white solid | (515) (513) |

TABLE 1-continued

Insecticidal Compounds

| Compound Number | Molecular Structure | Melting Point (° C.) | Appearance | Mol Ion (M + H), (M − H) |
|---|---|---|---|---|
| 77 | 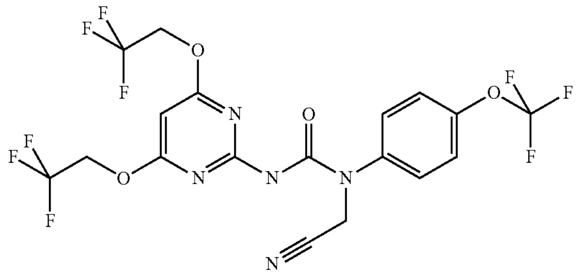 [SMILES: N#CCN(C(=O)Nc1nc(OCC(F)(F)F)cc(OCC(F)(F)F)n1)c1ccc(OC(F)(F)F)cc1] | n/a | yellow solid | (534), (532) |
| 78 | 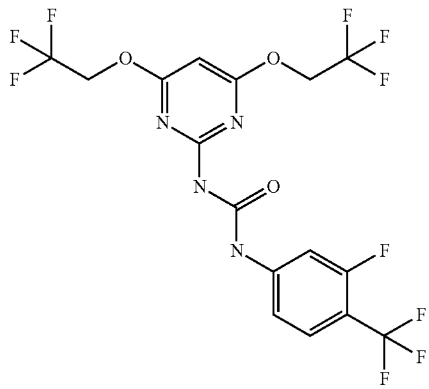 [SMILES: O=C(Nc1ccc(C(F)(F)F)c(F)c1)Nc1nc(OCC(F)(F)F)cc(OCC(F)(F)F)n1] | 172-175 | white solid | (497), (498) |
| 79 | 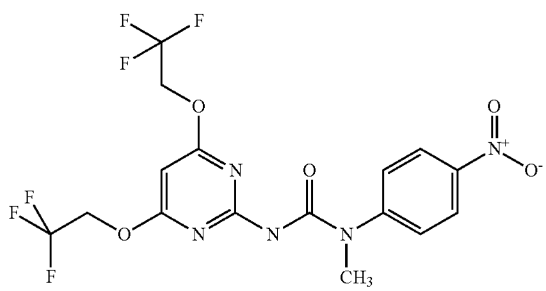 [SMILES: CN(C(=O)Nc1nc(OCC(F)(F)F)cc(OCC(F)(F)F)n1)c1ccc([N+](=O)[O-])cc1] | 150-151 | white solid | (470), (468) |
| 80 | 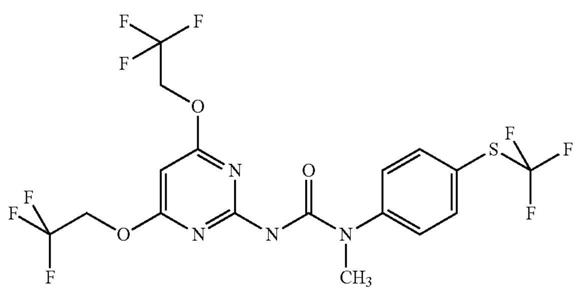 [SMILES: CN(C(=O)Nc1nc(OCC(F)(F)F)cc(OCC(F)(F)F)n1)c1ccc(SC(F)(F)F)cc1] | 86-87 | white solid | (525), (523) |
| 81 | 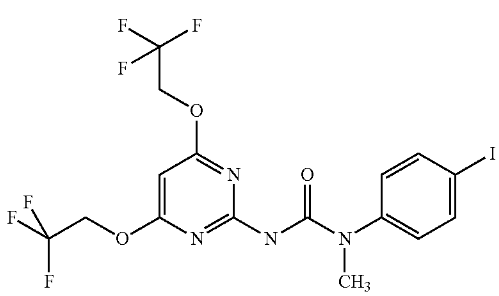 [SMILES: CN(C(=O)Nc1nc(OCC(F)(F)F)cc(OCC(F)(F)F)n1)c1ccc(I)cc1] | 134-135 | off white solid | (551), (549) |

TABLE 1-continued

Insecticidal Compounds

| Compound Number | Molecular Structure | Melting Point (° C.) | Appearance | Mol Ion (M + H), (M − H) |
|---|---|---|---|---|
| 82 | 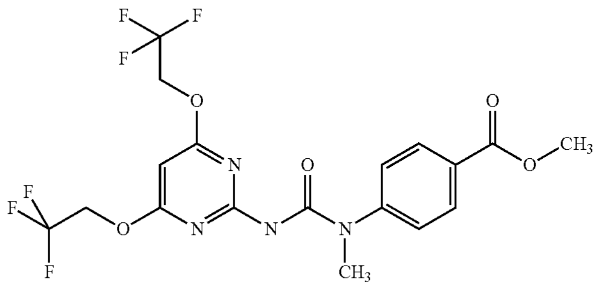 [SMILES: COC(=O)c1ccc(N(C)C(=O)Nc2nc(OCC(F)(F)F)cc(OCC(F)(F)F)n2)cc1] | 166-167 | off white solid | (483), (481) |
| 83 | 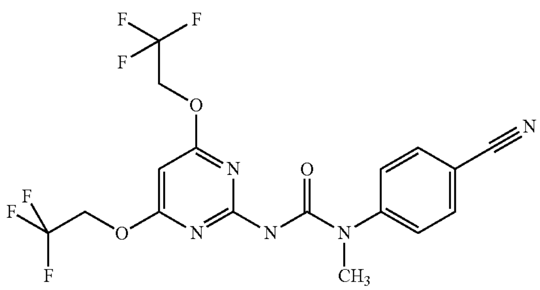 [SMILES: CN(C(=O)Nc1nc(OCC(F)(F)F)cc(OCC(F)(F)F)n1)c1ccc(C#N)cc1] | 114-116 | off white solid | (450), (448) |
| 84 | 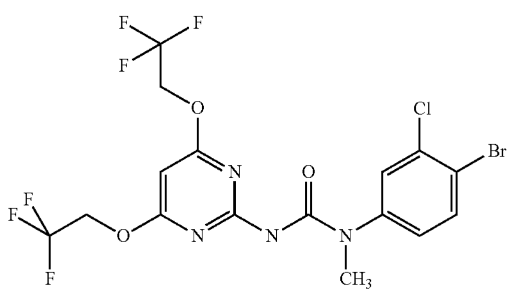 [SMILES: CN(C(=O)Nc1nc(OCC(F)(F)F)cc(OCC(F)(F)F)n1)c1ccc(Br)c(Cl)c1] | 121-123 | off white solid | (539, 537), (537, 535) |
| 85 | 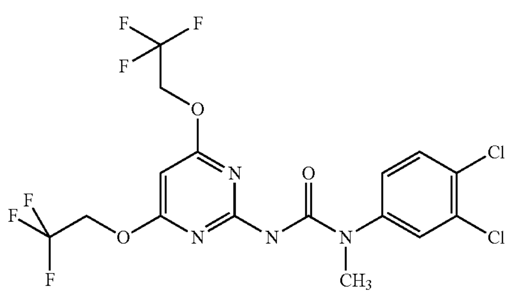 [SMILES: CN(C(=O)Nc1nc(OCC(F)(F)F)cc(OCC(F)(F)F)n1)c1ccc(Cl)c(Cl)c1] | 120-122 | white solid | (495, 493), (493, 491) |
| 86 | 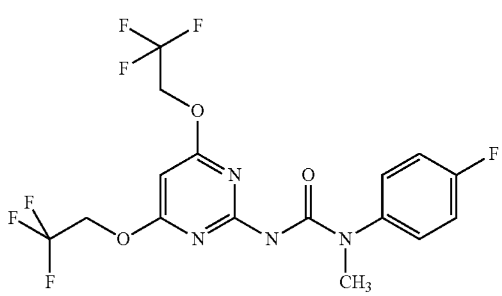 [SMILES: CN(C(=O)Nc1nc(OCC(F)(F)F)cc(OCC(F)(F)F)n1)c1ccc(F)cc1] | 150-155 | purple solid | (443), (441) |

TABLE 1-continued

| | Insecticidal Compounds | | | |
|---|---|---|---|---|
| Compound Number | Molecular Structure | Melting Point (° C.) | Appearance | Mol Ion (M + H), (M − H) |
| 87 | | 80-84 | white solid | (600), (598) |
| 88 | | — | clear oil | (658), (716, M + AcOH − 1) |
| 89 | | — | clear oil | (644) (702, M + AcOH − 1) |

TABLE 1-continued

Insecticidal Compounds

| Compound Number | Molecular Structure | Melting Point (° C.) | Appearance | Mol Ion (M + H), (M − H) |
|---|---|---|---|---|
| 90 | 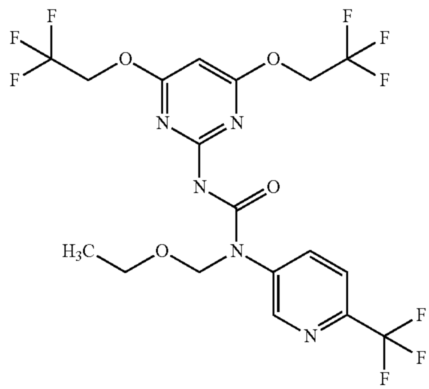 [SMILES: CCOCN(C(=O)Nc1nc(OCC(F)(F)F)cc(OCC(F)(F)F)n1)c1ccc(C(F)(F)F)nc1] | 112-113 | white solid | (492, M − EtOH) (536) |
| 91 | 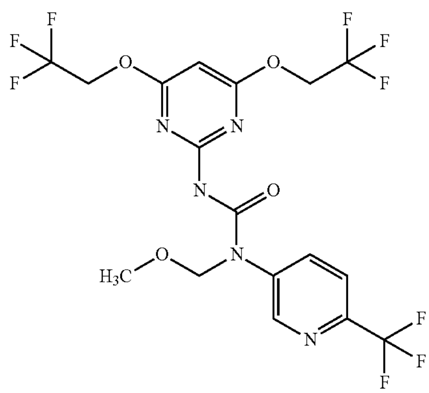 [SMILES: COCN(C(=O)Nc1nc(OCC(F)(F)F)cc(OCC(F)(F)F)n1)c1ccc(C(F)(F)F)nc1] | 111-112 | white solid | (492, M − EtOH) (522) |
| 92 | 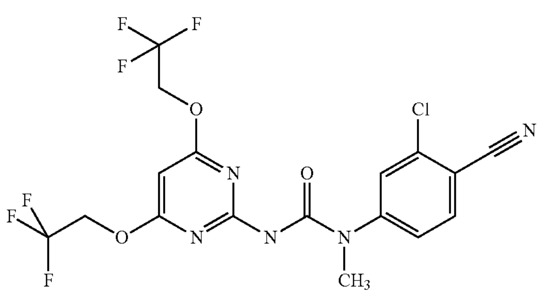 [SMILES: CN(C(=O)Nc1nc(OCC(F)(F)F)cc(OCC(F)(F)F)n1)c1ccc(C#N)c(Cl)c1] | 165-166 | white solid | (484), (482) |
| 93 | 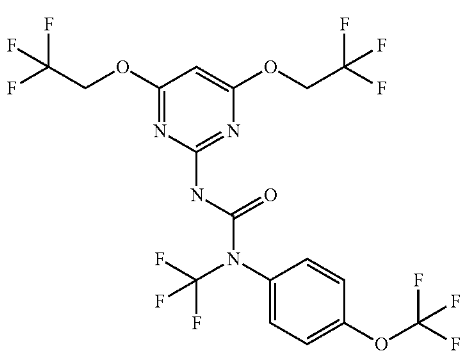 [SMILES: O=C(Nc1nc(OCC(F)(F)F)cc(OCC(F)(F)F)n1)N(c1ccc(OC(F)(F)F)cc1)C(F)(F)F] | 157-160 | white solid | (563), (561) |

TABLE 1-continued

Insecticidal Compounds

| Compound Number | Molecular Structure | Melting Point (° C.) | Appearance | Mol Ion (M + H), (M − H) |
|---|---|---|---|---|
| 94 | 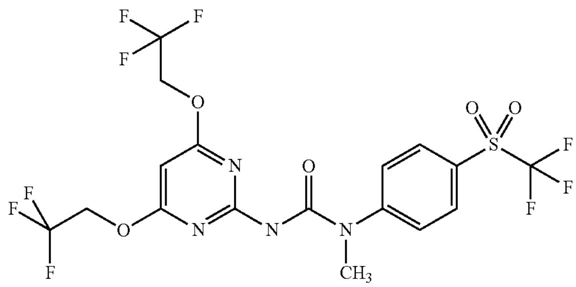 [SMILES: CN(C(=O)Nc1nc(OCC(F)(F)F)cc(OCC(F)(F)F)n1)c1ccc(S(=O)(=O)C(F)(F)F)cc1] | | clear glass | (557), (555) |
| 95 | 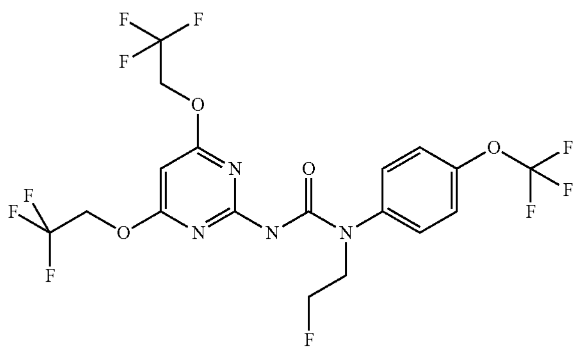 [SMILES: O=C(Nc1nc(OCC(F)(F)F)cc(OCC(F)(F)F)n1)N(CCF)c1ccc(OC(F)(F)F)cc1] | 119-120 | white solid | (541), (539) |
| 96 | 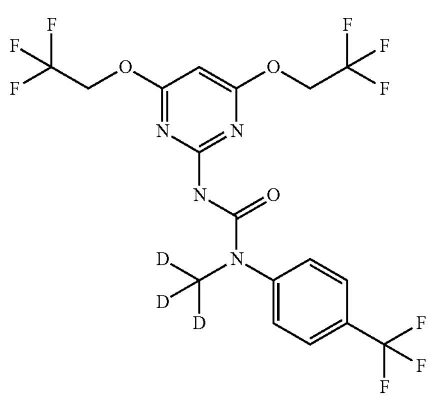 [SMILES: [2H]C([2H])([2H])N(C(=O)Nc1nc(OCC(F)(F)F)cc(OCC(F)(F)F)n1)c1ccc(C(F)(F)F)cc1] | 68-72 | white solid | (496), (494) |
| 97 | 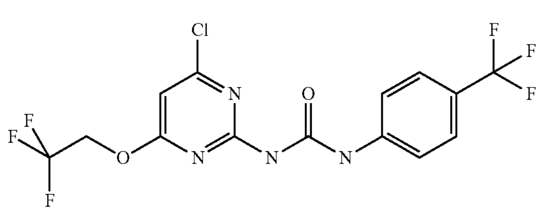 [SMILES: O=C(Nc1ccc(C(F)(F)F)cc1)Nc1nc(Cl)cc(OCC(F)(F)F)n1] | 220-223 | white solid | (415), (413) |

TABLE 1-continued

Insecticidal Compounds

| Compound Number | Molecular Structure | Melting Point (° C.) | Appearance | Mol Ion (M + H), (M − H) |
|---|---|---|---|---|
| 98 | 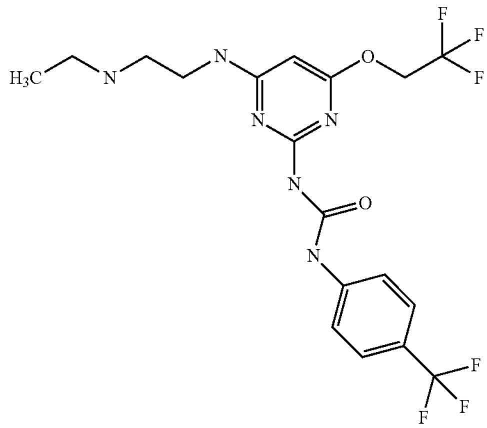 [SMILES: CCNCCNc1cc(OCC(F)(F)F)nc(NC(=O)Nc2ccc(C(F)(F)F)cc2)n1] | 183-185 | white solid | (466), (465) |
| 99 | 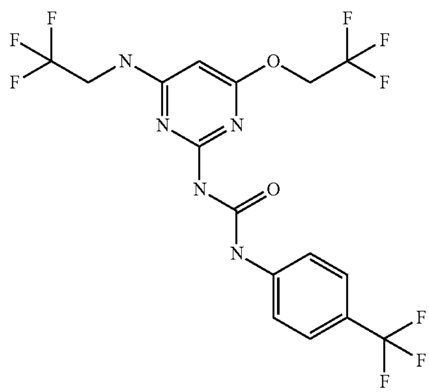 | 194-196 | white solid | (478), (476) |
| 100 | 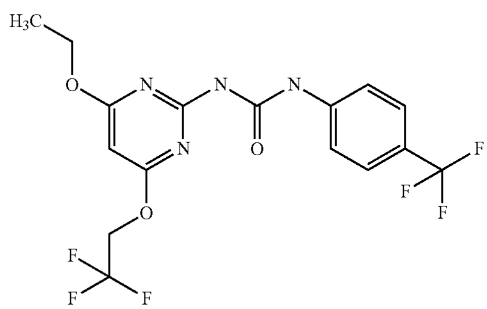 [SMILES: CCOc1cc(OCC(F)(F)F)nc(NC(=O)Nc2ccc(C(F)(F)F)cc2)n1] | 206-210 | light pink powder | (425), (423) |
| 101 | 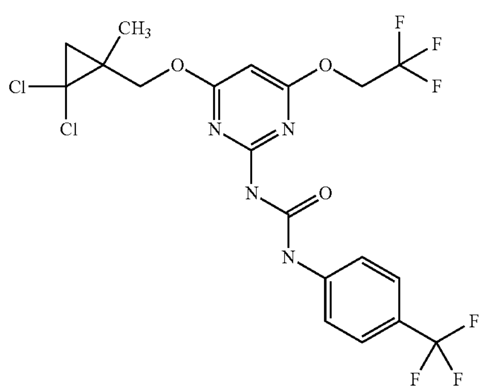 [SMILES: CC1(COc2cc(OCC(F)(F)F)nc(NC(=O)Nc3ccc(C(F)(F)F)cc3)n2)CC1(Cl)Cl] | n/a | white solid | (533), (531) |

TABLE 1-continued

Insecticidal Compounds

| Compound Number | Molecular Structure | Melting Point (° C.) | Appearance | Mol Ion (M + H), (M − H) |
|---|---|---|---|---|
| 102 | 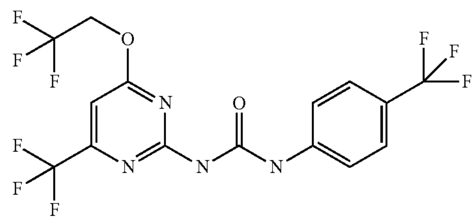 [SMILES: O=C(Nc1ccc(C(F)(F)F)cc1)Nc1nc(OCC(F)(F)F)cc(C(F)(F)F)n1] | 197-199 | white solid | (449), (447) |
| 103 | 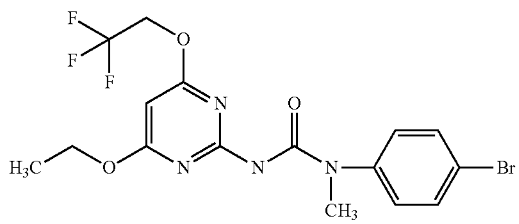 [SMILES: CCOc1cc(OCC(F)(F)F)nc(NC(=O)N(C)c2ccc(Br)cc2)n1] | n/a | yellow tacky oil | (449, 451), (447, 449) |
| 104 | 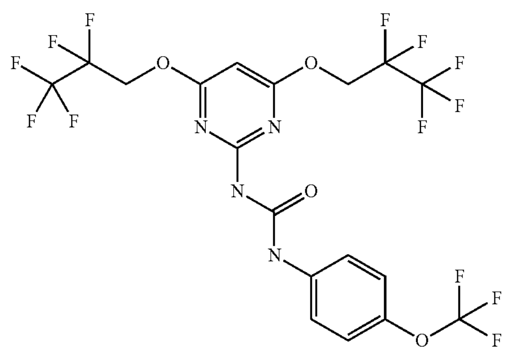 [SMILES: O=C(Nc1ccc(OC(F)(F)F)cc1)Nc1nc(OCC(F)(F)C(F)(F)F)cc(OCC(F)(F)C(F)(F)F)n1] | 174-175 | white solid | (595), (593) |
| 105 | 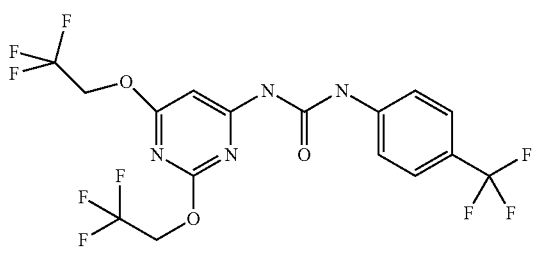 [SMILES: O=C(Nc1ccc(C(F)(F)F)cc1)Nc1cc(OCC(F)(F)F)nc(OCC(F)(F)F)n1] | 180-182 | yellow solid | (479), (477) |
| 106 | 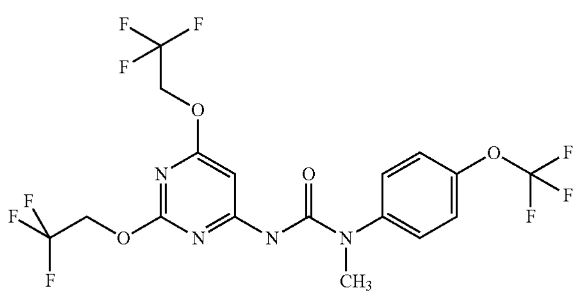 [SMILES: CN(C(=O)Nc1cc(OCC(F)(F)F)nc(OCC(F)(F)F)n1)c1ccc(OC(F)(F)F)cc1] | n/a | clear glass | (509), (507) |

TABLE 1-continued
Insecticidal Compounds
| Compound Number | Molecular Structure | Melting Point (° C.) | Appearance | Mol Ion (M + H), (M − H) |
|---|---|---|---|---|
| 107 | 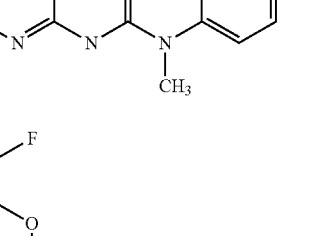 | n/a | yellow glass | (493), (491) |
| 108 | 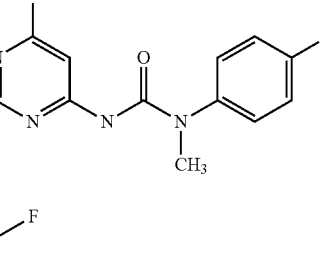 | n/a | yellow glass | (505, 503), (503, 501) |
| 109 | 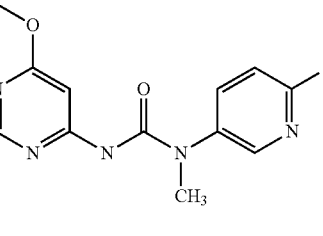 | n/a | clear glass | (506, 504), (504, 501) |
| 110 | 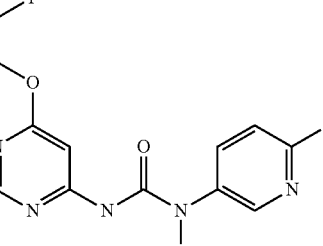 | n/a | clear glass | (460), (458) |
| 111 | 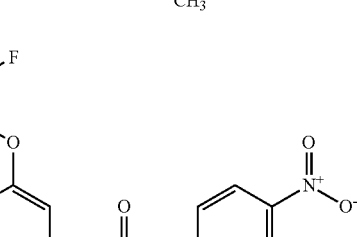 | n/a | yellow oil | (470), (468) |

TABLE 1-continued

Insecticidal Compounds

| Compound Number | Molecular Structure | Melting Point (° C.) | Appearance | Mol Ion (M + H), (M − H) |
|---|---|---|---|---|
| 112 | 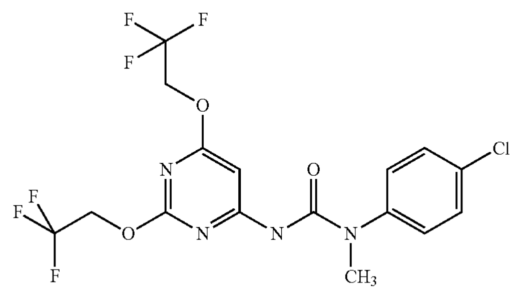 [SMILES: CN(C(=O)Nc1cc(OCC(F)(F)F)nc(OCC(F)(F)F)n1)c1ccc(Br)cc1] | n/a | yellow glass | (459), (457) |
| 113 | 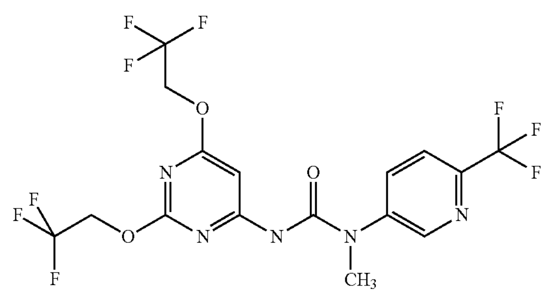 [SMILES: CN(C(=O)Nc1cc(OCC(F)(F)F)nc(OCC(F)(F)F)n1)c1ccc(C(F)(F)F)nc1] | 112-113 | white solid | (494), (NA) |
| 114 | 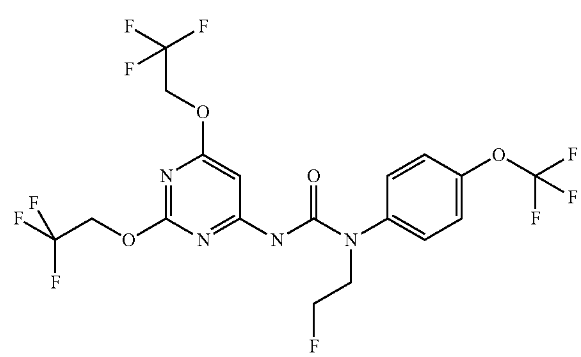 [SMILES: O=C(Nc1cc(OCC(F)(F)F)nc(OCC(F)(F)F)n1)N(CCF)c1ccc(OC(F)(F)F)cc1] | n/a | clear glass | (541), (539) |
| 115 | 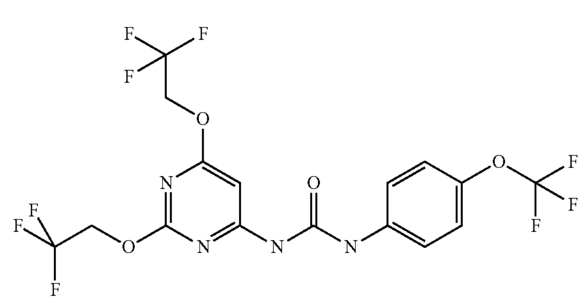 [SMILES: O=C(Nc1ccc(OC(F)(F)F)cc1)Nc1cc(OCC(F)(F)F)nc(OCC(F)(F)F)n1] | 187-190 | white solid | (495), (493) |

TABLE 1-continued

Insecticidal Compounds

| Compound Number | Molecular Structure | Melting Point (° C.) | Appearance | Mol Ion (M + H), (M − H) |
|---|---|---|---|---|
| 116 | 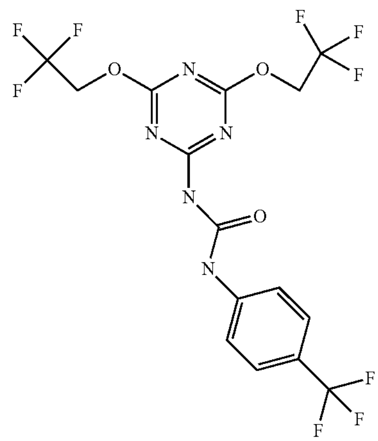 [SMILES: O=C(Nc1ccc(C(F)(F)F)cc1)Nc1nc(OCC(F)(F)F)nc(OCC(F)(F)F)n1] | 200-202 | white solid | (480), (478) |
| 117 | 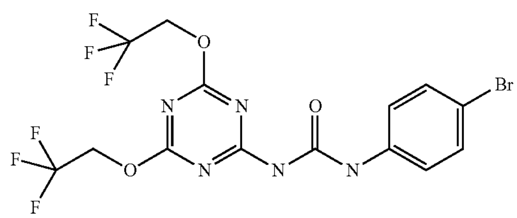 [SMILES: O=C(Nc1ccc(Br)cc1)Nc1nc(OCC(F)(F)F)nc(OCC(F)(F)F)n1] | 213-215 | white solid | (492, 490), (490, 488) |
| 118 | 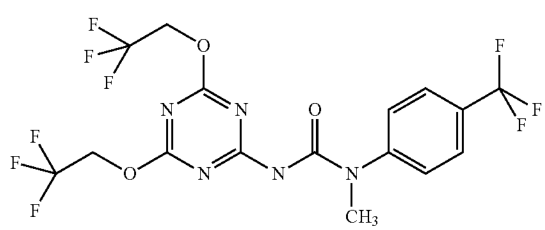 [SMILES: CN(C(=O)Nc1nc(OCC(F)(F)F)nc(OCC(F)(F)F)n1)c1ccc(C(F)(F)F)cc1] | 130-132 | white solid | (494), (492) |
| 119 | 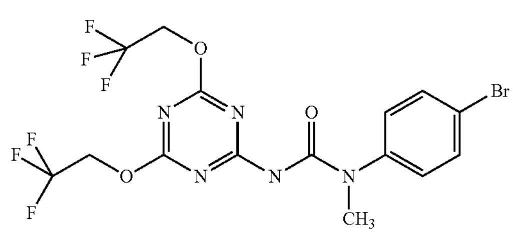 [SMILES: CN(C(=O)Nc1nc(OCC(F)(F)F)nc(OCC(F)(F)F)n1)c1ccc(Br)cc1] | 110-112 | white glass | (506, 504), (504, 502) |
| 120 | 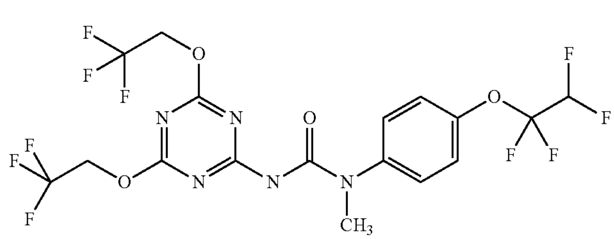 [SMILES: CN(C(=O)Nc1nc(OCC(F)(F)F)nc(OCC(F)(F)F)n1)c1ccc(OC(F)(F)C(F)F)cc1] | 102-104 | white solid | (542), (540) |

TABLE 1-continued

Insecticidal Compounds

| Compound Number | Molecular Structure | Melting Point (° C.) | Appearance | Mol Ion (M + H), (M − H) |
| --- | --- | --- | --- | --- |
| 121 | 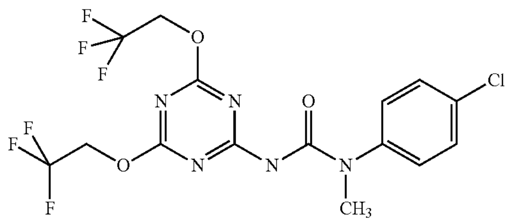 [SMILES: CN(C(=O)Nc1nc(OCC(F)(F)F)nc(OCC(F)(F)F)n1)c1ccc(Cl)cc1] | n/a | brown glass | (462, 460), (458) |
| 122 | 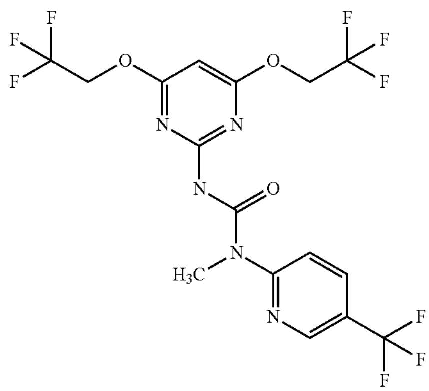 | 140-143 | white solid | (494), (492) |
| 123 | 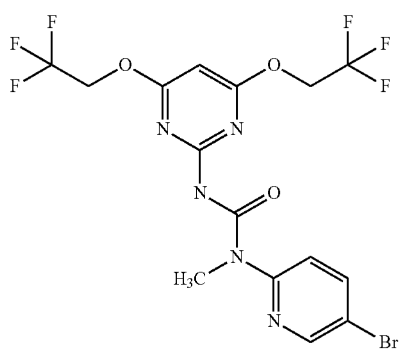 [SMILES: CN(C(=O)Nc1nc(OCC(F)(F)F)cc(OCC(F)(F)F)n1)c1ccc(Br)cn1] | 149-151 | white solid | (506, 504), (504, 502) |
| 124 | 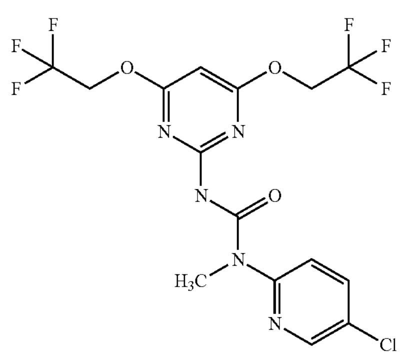 | 148-150 | white solid | (460), (458) |

TABLE 1-continued

Insecticidal Compounds

| Compound Number | Molecular Structure | Melting Point (° C.) | Appearance | Mol Ion (M + H), (M − H) |
|---|---|---|---|---|
| 125 | 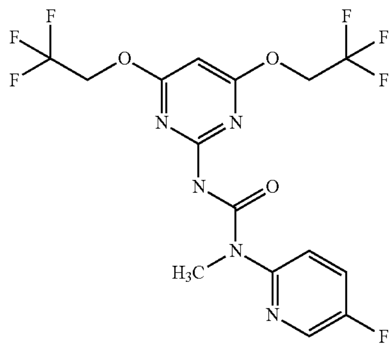 | 135-137 | white solid | (444), (442) |
| 126 | 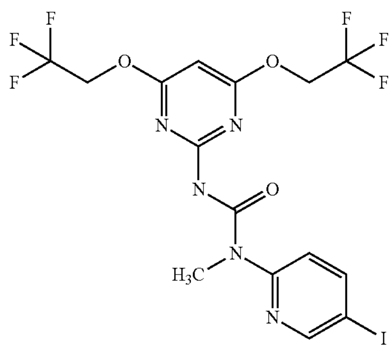 [SMILES: CN(C(=O)Nc1nc(OCC(F)(F)F)cc(OCC(F)(F)F)n1)c1ccc(I)cn1] | 150-152 | yellow solid | (552), (550) |
| 127 | 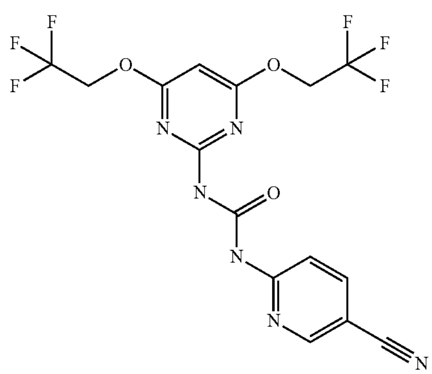 [SMILES: N#Cc1ccc(NC(=O)Nc2nc(OCC(F)(F)F)cc(OCC(F)(F)F)n2)nc1] | 215-218 | white solid | (437), (435) |
| 128 | 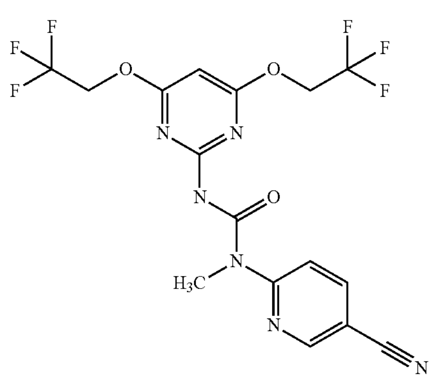 [SMILES: CN(C(=O)Nc1nc(OCC(F)(F)F)cc(OCC(F)(F)F)n1)c1ccc(C#N)cn1] | 173-176 | white solid | (451), (449) |

TABLE 1-continued

Insecticidal Compounds

| Compound Number | Molecular Structure | Melting Point (° C.) | Appearance | Mol Ion (M + H), (M − H) |
|---|---|---|---|---|
| 129 | 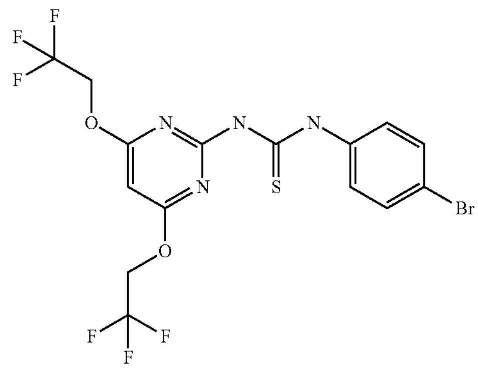 [SMILES: FC(F)(F)COc1cc(OCC(F)(F)F)nc(NC(=S)Nc2ccc(Br)cc2)n1] | 195-201 | white solid | (505), (507) |
| 130 | 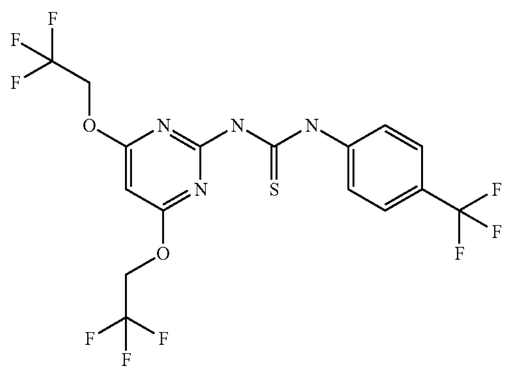 [SMILES: FC(F)(F)COc1cc(OCC(F)(F)F)nc(NC(=S)Nc2ccc(C(F)(F)F)cc2)n1] | 176-179 | white solid | (493), (496) |
| 131 | 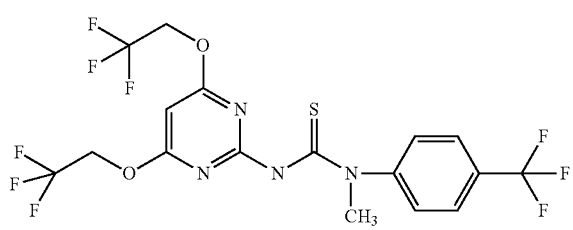 [SMILES: CN(C(=S)Nc1nc(OCC(F)(F)F)cc(OCC(F)(F)F)n1)c1ccc(C(F)(F)F)cc1] | 109-111 | yellow solid | (509), (507) |
| 132 | 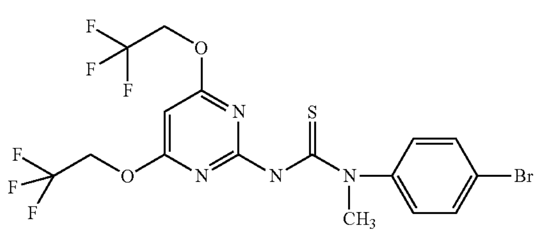 [SMILES: CN(C(=S)Nc1nc(OCC(F)(F)F)cc(OCC(F)(F)F)n1)c1ccc(Br)cc1] | 116-118 | yellow solid | (519, 521), (517, 519) |
| 133 | 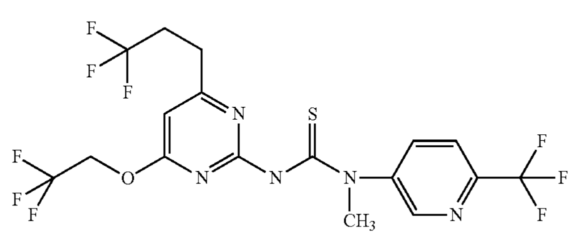 [SMILES: CN(C(=S)Nc1nc(CCC(F)(F)F)cc(OCC(F)(F)F)n1)c1ccc(C(F)(F)F)nc1] | 124-127 | yellow solid | (510), (508) |

TABLE 1-continued

Insecticidal Compounds

| Compound Number | Molecular Structure | Melting Point (° C.) | Appearance | Mol Ion (M + H), (M − H) |
|---|---|---|---|---|
| 134 | 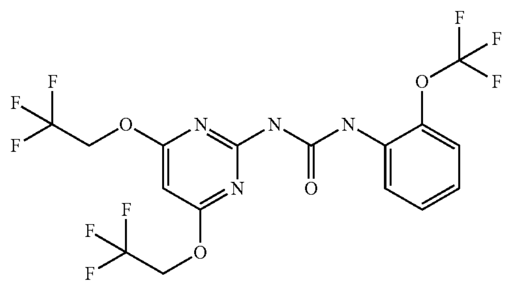 [SMILES: O=C(Nc1nc(OCC(F)(F)F)cc(OCC(F)(F)F)n1)Nc1ccccc1OC(F)(F)F] | 191-194 | tan solid | (495.2), (492.9) |
| 135 | 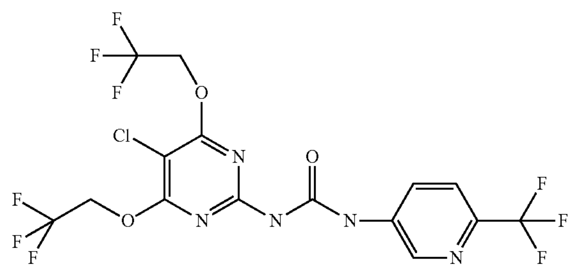 | 165-174 | tan solid | (514), (512) |
| 136 | 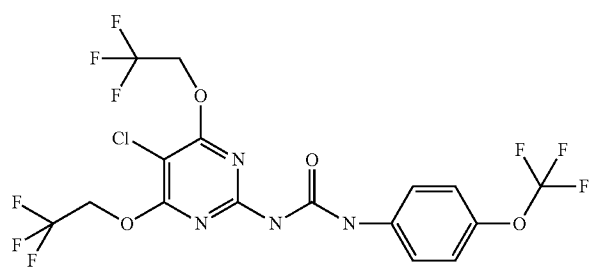 [SMILES: O=C(Nc1ccc(OC(F)(F)F)cc1)Nc1nc(OCC(F)(F)F)c(Cl)c(OCC(F)(F)F)n1] | 182-185 | yellow solid | (529), (527) |
| 137 | 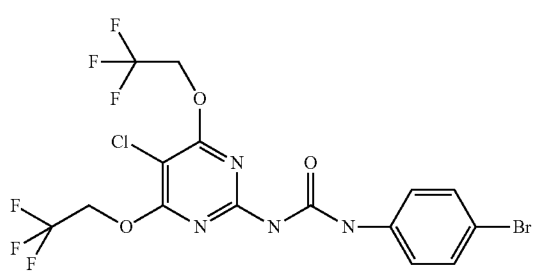 | 176-203 | yellow solid | (524), (522) |
| 138 | 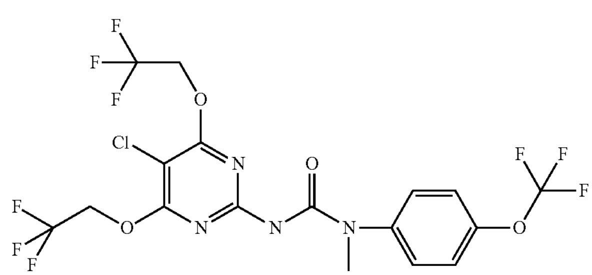 [SMILES: CN(C(=O)Nc1nc(OCC(F)(F)F)c(Cl)c(OCC(F)(F)F)n1)c1ccc(OC(F)(F)F)cc1] | N/A | amber oil | (543), (541) |

TABLE 1-continued

Insecticidal Compounds

| Compound Number | Molecular Structure | Melting Point (° C.) | Appearance | Mol Ion (M + H), (M − H) |
| --- | --- | --- | --- | --- |
| 139 | 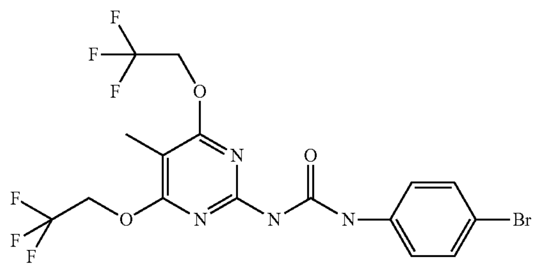 [SMILES: Cc1c(OCC(F)(F)F)nc(NC(=O)Nc2ccc(Br)cc2)nc1OCC(F)(F)F] | 190-210 | light tan solid | (504), (502) |
| 140 | 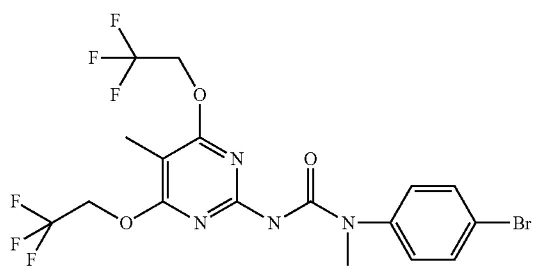 [SMILES: Cc1c(OCC(F)(F)F)nc(NC(=O)N(C)c2ccc(Br)cc2)nc1OCC(F)(F)F] | 120-150 | light tan solid | (518), (516) |
| 141 | 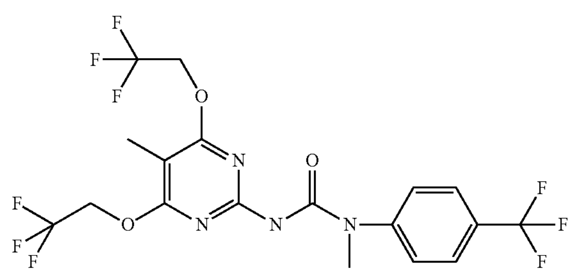 [SMILES: Cc1c(OCC(F)(F)F)nc(NC(=O)N(C)c2ccc(C(F)(F)F)cc2)nc1OCC(F)(F)F] | 134-140 | light tan solid | (507), (505) |
| 142 | 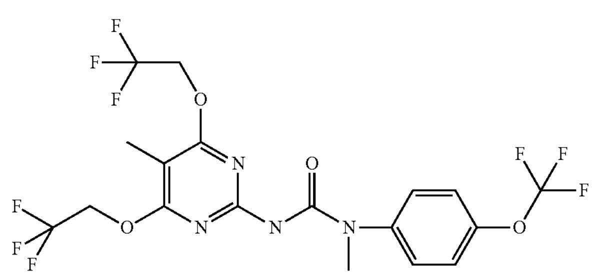 [SMILES: Cc1c(OCC(F)(F)F)nc(NC(=O)N(C)c2ccc(OC(F)(F)F)cc2)nc1OCC(F)(F)F] | 110-136 | tan solid | (523), (521) |
| 143 | 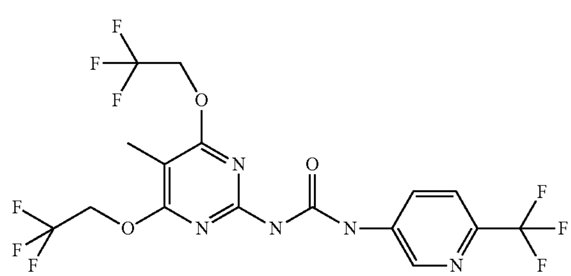 [SMILES: Cc1c(OCC(F)(F)F)nc(NC(=O)Nc2ccc(C(F)(F)F)nc2)nc1OCC(F)(F)F] | 124-169 | tan solid | (494), (492) |

TABLE 1-continued

| Insecticidal Compounds | | | | |
|---|---|---|---|---|
| Compound Number | Molecular Structure | Melting Point (° C.) | Appearance | Mol Ion (M + H), (M − H) |
| 144 | | 91-119 | light tan solid | (528), (526) |
| 145 | | 168-183 | light tan solid | (513), (511) |
| 146 | | 159-178 | light tan solid | (525), (523) |
| 147 | | 179-189 | tan solid | (493), (491) |
| 148 | | 88-98 | tan solid | (508), (506) |

TABLE 1-continued

Insecticidal Compounds

| Compound Number | Molecular Structure | Melting Point (° C.) | Appearance | Mol Ion (M + H), (M − H) |
|---|---|---|---|---|
| 149 | 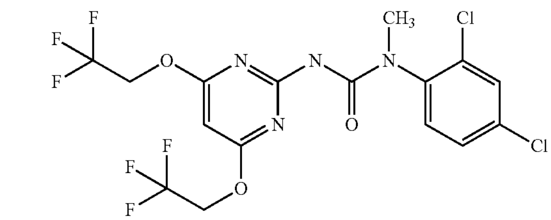 [SMILES: CN(C(=O)Nc1nc(OCC(F)(F)F)cc(OCC(F)(F)F)n1)c1ccc(Cl)cc1Cl] | 106-109 | light yellow solid | (493.2), (491.2) |
| 150 | 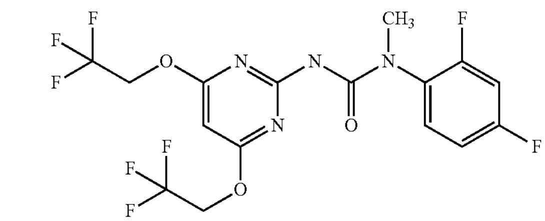 [SMILES: CN(C(=O)Nc1nc(OCC(F)(F)F)cc(OCC(F)(F)F)n1)c1ccc(F)cc1F] | 101-104 | tan solid | (461.3), (459.2) |
| 151 | 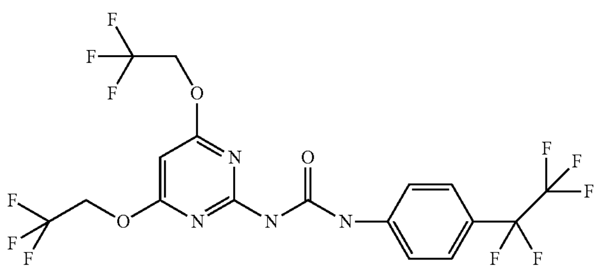 | 183-185 | White solid | (529), (527) |
| 152 | 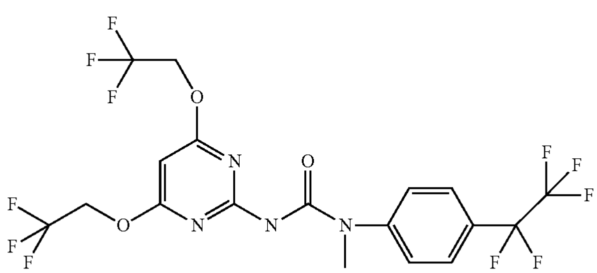 [SMILES: CN(C(=O)Nc1nc(OCC(F)(F)F)cc(OCC(F)(F)F)n1)c1ccc(C(F)(F)C(F)(F)F)cc1] | 72-74 | White solid | (527), (541) |
| 153 | 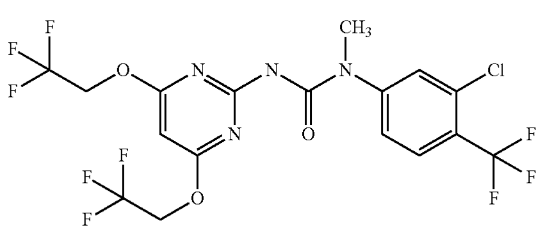 [SMILES: CN(C(=O)Nc1nc(OCC(F)(F)F)cc(OCC(F)(F)F)n1)c1ccc(C(F)(F)F)c(Cl)c1] | 62-65 | white solid | (526.0), (524.8) |
| 154 | 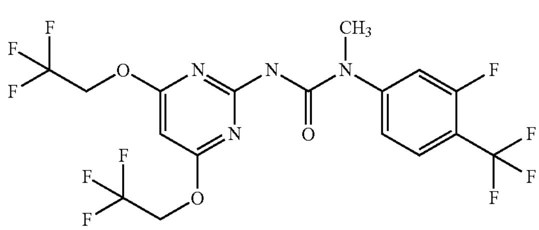 [SMILES: CN(C(=O)Nc1nc(OCC(F)(F)F)cc(OCC(F)(F)F)n1)c1ccc(C(F)(F)F)c(F)c1] | 84-86 | white solid | (510.0), (508.9) |

TABLE 1-continued

Insecticidal Compounds

| Compound Number | Molecular Structure | Melting Point (° C.) | Appearance | Mol Ion (M + H), (M − H) |
|---|---|---|---|---|
| 155 | 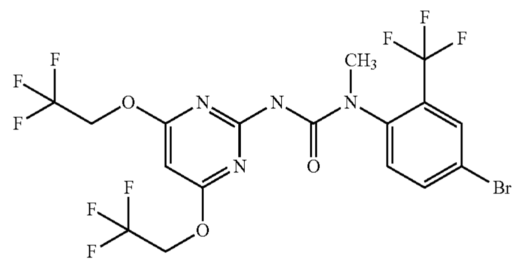 [SMILES: CN(C(=O)Nc1nc(OCC(F)(F)F)cc(OCC(F)(F)F)n1)c1ccc(Br)cc1C(F)(F)F] | 108-111 | off-white solid | (571.2), (569.2) |
| 156 | 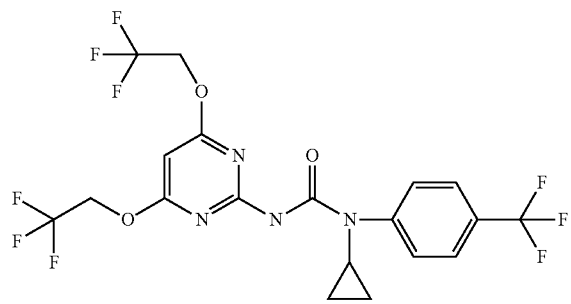 [SMILES: O=C(Nc1nc(OCC(F)(F)F)cc(OCC(F)(F)F)n1)N(c1ccc(C(F)(F)F)cc1)C1CC1] | 82-84 | white poweder | (519), (517) |
| 157 | 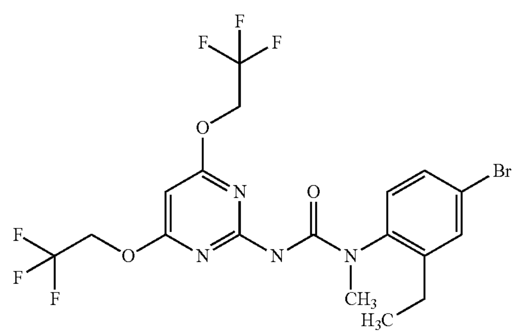 [SMILES: CCc1cc(Br)ccc1N(C)C(=O)Nc1nc(OCC(F)(F)F)cc(OCC(F)(F)F)n1] | 98-100 | off-white powder | (533.3), (531.1) |
| 158 | 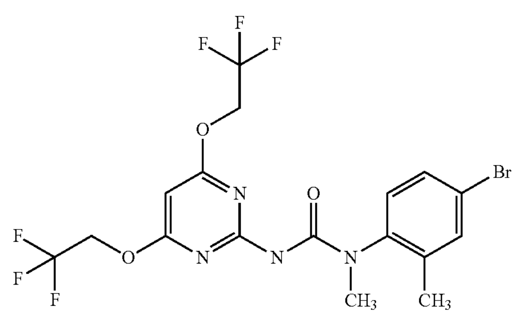 [SMILES: Cc1cc(Br)ccc1N(C)C(=O)Nc1nc(OCC(F)(F)F)cc(OCC(F)(F)F)n1] | 102-104 | off-white solid | (517.2), (515.2) |
| 159 | 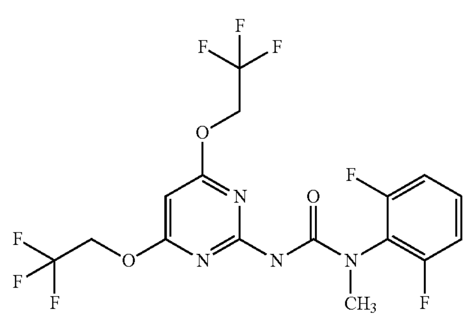 [SMILES: CN(C(=O)Nc1nc(OCC(F)(F)F)cc(OCC(F)(F)F)n1)c1c(F)cccc1F] | 112-113 | white solid | (461.5), (459.2) |

TABLE 1-continued

Insecticidal Compounds

| Compound Number | Molecular Structure | Melting Point (° C.) | Appearance | Mol Ion (M + H), (M − H) |
|---|---|---|---|---|
| 160 | 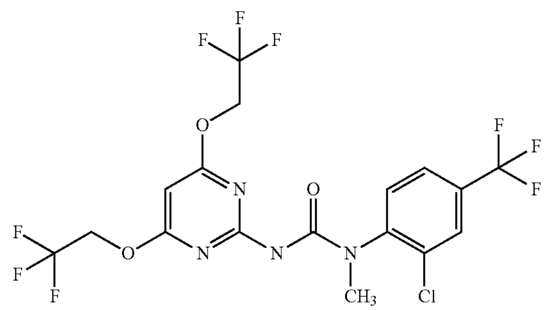 | | colorless glass | (527.3), (525.2) |
| 161 | 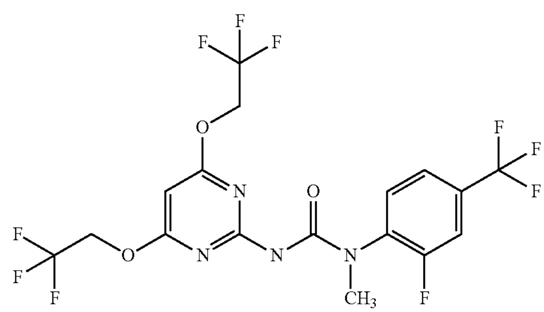 | | colorless oil | (511.3), (509.2) |
| 162 | 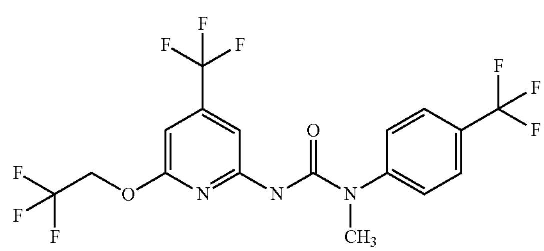 [SMILES: CN(C(=O)Nc1cc(C(F)(F)F)cc(OCC(F)(F)F)n1)c1ccc(C(F)(F)F)cc1] | 124-127 | white solid | (461), (459) |
| 163 | 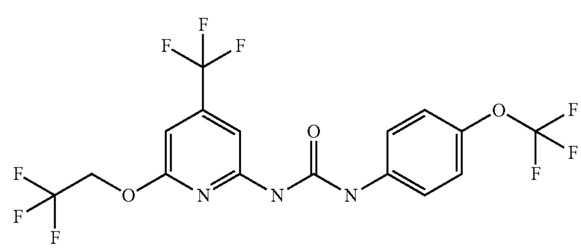 [SMILES: O=C(Nc1ccc(OC(F)(F)F)cc1)Nc1cc(C(F)(F)F)cc(OCC(F)(F)F)n1] | 168-194 | white solid | (463), (461) |
| 164 | 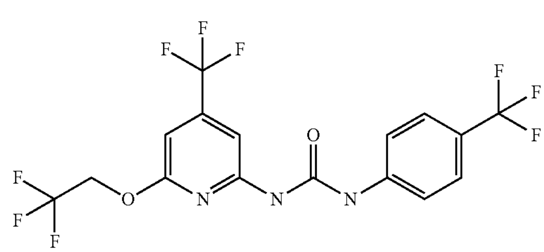 [SMILES: O=C(Nc1ccc(C(F)(F)F)cc1)Nc1cc(C(F)(F)F)cc(OCC(F)(F)F)n1] | 166-187 | pale yellow solid | (447), (445) |

TABLE 1-continued

Insecticidal Compounds

| Compound Number | Molecular Structure | Melting Point (° C.) | Appearance | Mol Ion (M + H), (M − H) |
|---|---|---|---|---|
| 165 | 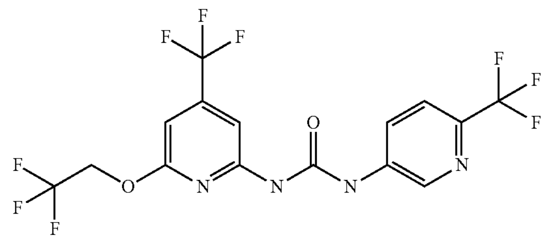 [SMILES: O=C(Nc1ccc(C(F)(F)F)nc1)Nc1cc(C(F)(F)F)cc(OCC(F)(F)F)n1] | 161-187 | pale yellow solid | (440), (438) |
| 166 | 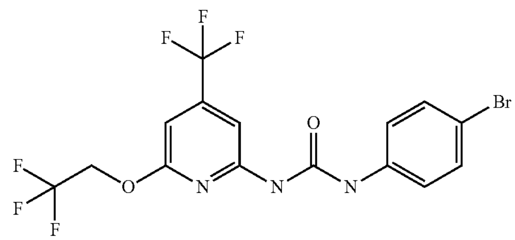 | 166-199 | pale yellow solid | (458), (456) |
| 167 | 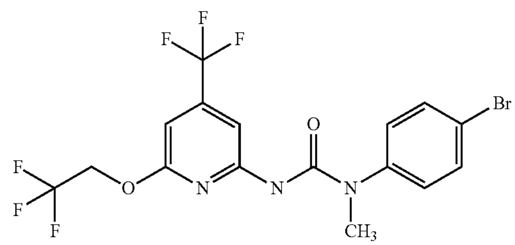 | 114-122 | white solid | (472), (470) |
| 168 | 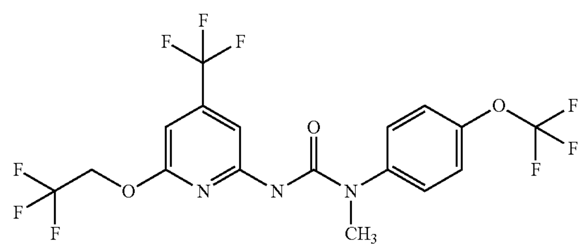 [SMILES: CN(C(=O)Nc1cc(C(F)(F)F)cc(OCC(F)(F)F)n1)c1ccc(OC(F)(F)F)cc1] | 120-128 | white solid | (477), (475) |
| 169 | 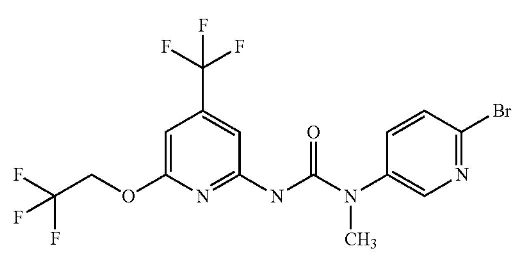 | 120-137 | white solid | (473), (471) |
| 170 | 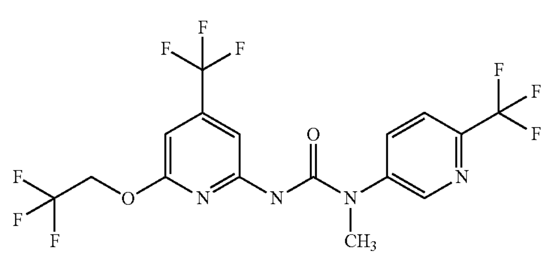 [SMILES: CN(C(=O)Nc1cc(C(F)(F)F)cc(OCC(F)(F)F)n1)c1ccc(C(F)(F)F)nc1] | 131-153 | white solid | (462), (460) |

TABLE 1-continued

Insecticidal Compounds

| Compound Number | Molecular Structure | Melting Point (°C.) | Appearance | Mol Ion (M + H), (M − H) |
|---|---|---|---|---|
| 171 | 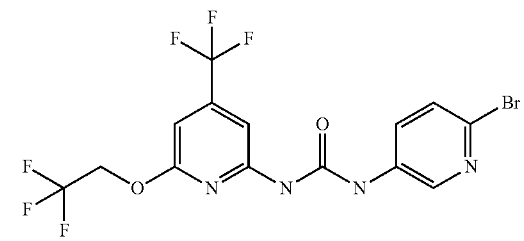 | 178-226 | tan solid | (459), (457) |
| 172 | 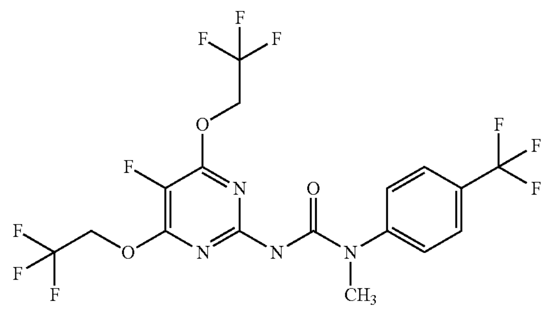 [SMILES: CN(C(=O)Nc1nc(OCC(F)(F)F)c(F)c(OCC(F)(F)F)n1)c1ccc(C(F)(F)F)cc1] | Not tested | yellow solid | (511), (509) |
| 173 | 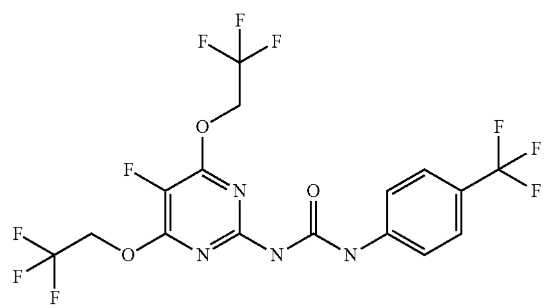 [SMILES: O=C(Nc1ccc(C(F)(F)F)cc1)Nc1nc(OCC(F)(F)F)c(F)c(OCC(F)(F)F)n1] | Not tested | white solid | (497), (495) |
| 174 | 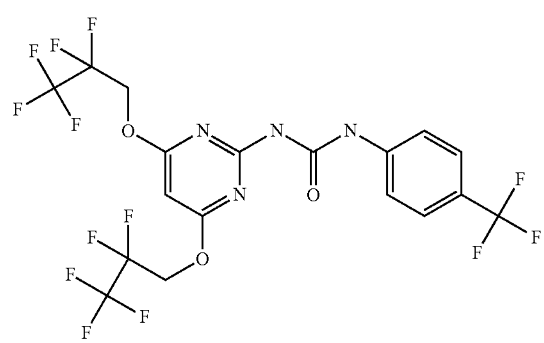 [SMILES: O=C(Nc1ccc(C(F)(F)F)cc1)Nc1nc(OCC(F)(F)C(F)(F)F)cc(OCC(F)(F)C(F)(F)F)n1] | 205-206 | off-white solid | (578.8, M − H) |

TABLE 1-continued
Insecticidal Compounds
| Compound Number | Molecular Structure | Melting Point (°C.) | Appearance | Mol Ion (M + H), (M − H) |
|---|---|---|---|---|
| 175 | 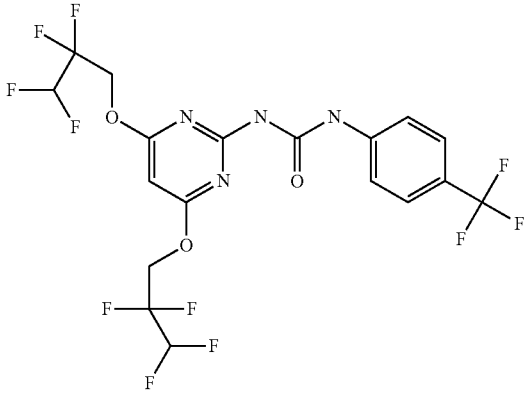 [SMILES: O=C(Nc1ccc(C(F)(F)F)cc1)Nc1nc(OCC(F)(F)C(F)F)cc(OCC(F)(F)C(F)F)n1] | 188-189 | off-white solid | (543.0, M − H) |
| 176 | 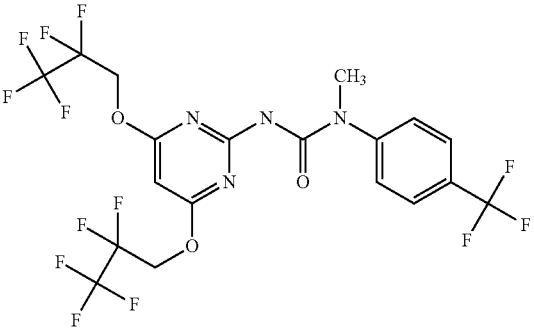 [SMILES: CN(C(=O)Nc1nc(OCC(F)(F)C(F)(F)F)cc(OCC(F)(F)C(F)(F)F)n1)c1ccc(C(F)(F)F)cc1] | 87-89 | white solid | (593.1, M − H) |
| 177 | 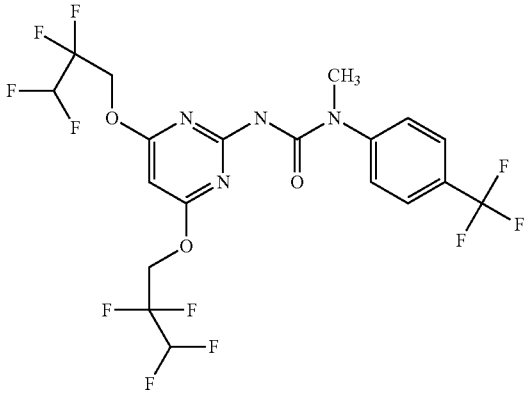 [SMILES: CN(C(=O)Nc1nc(OCC(F)(F)C(F)F)cc(OCC(F)(F)C(F)F)n1)c1ccc(C(F)(F)F)cc1] | 87-89 | white solid | (557.3, M − H) |
| 178 | 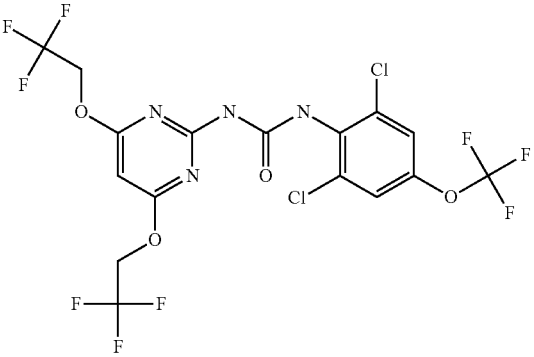 [SMILES: O=C(Nc1nc(OCC(F)(F)F)cc(OCC(F)(F)F)n1)Nc1c(Cl)cc(OC(F)(F)F)cc1Cl] | 133-134 | white solid | (564.9, M − H) |

TABLE 1-continued

Insecticidal Compounds

| Compound Number | Molecular Structure | Melting Point (° C.) | Appearance | Mol Ion (M + H), (M − H) |
|---|---|---|---|---|
| 179 | 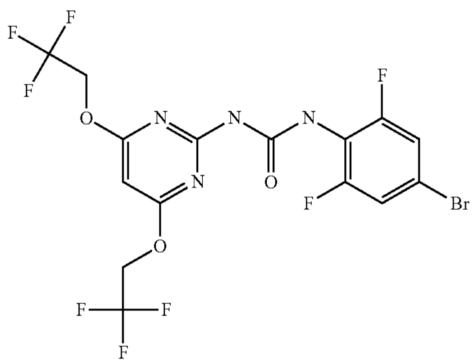 [SMILES: O=C(Nc1nc(OCC(F)(F)F)cc(OCC(F)(F)F)n1)Nc1c(F)cc(Br)cc1F] | 183-185 | white solid | (527.9, M − H) |
| 180 | 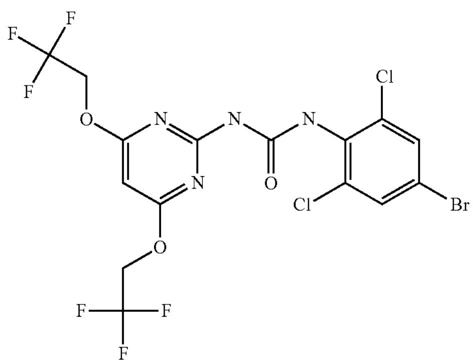 [SMILES: O=C(Nc1nc(OCC(F)(F)F)cc(OCC(F)(F)F)n1)Nc1c(Cl)cc(Br)cc1Cl] | 155-157 | grey-brown solid | (558.8, M − H) |
| 181 | 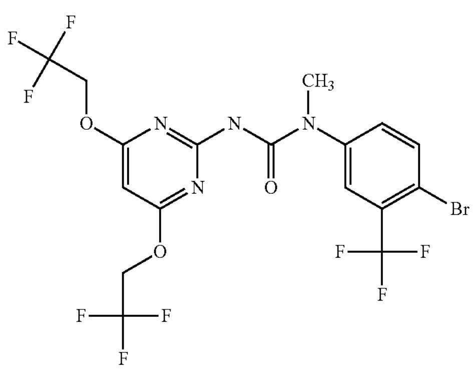 [SMILES: CN(C(=O)Nc1nc(OCC(F)(F)F)cc(OCC(F)(F)F)n1)c1ccc(Br)c(C(F)(F)F)c1] | 74-76 | off-white solid | (570.9, M − H) |
| 182 | 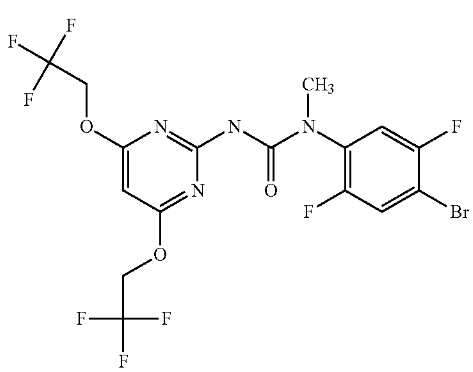 [SMILES: CN(C(=O)Nc1nc(OCC(F)(F)F)cc(OCC(F)(F)F)n1)c1cc(F)c(Br)cc1F] | 87-89 | off-white solid | (540.9, M − H) |

TABLE 1-continued

Insecticidal Compounds

| Compound Number | Molecular Structure | Melting Point (°C.) | Appearance | Mol Ion (M + H), (M − H) |
|---|---|---|---|---|
| 183 | [structure: 4,6-bis(2,2,2-trifluoroethoxy)-3-fluoropyridin-2-yl urea with N-methyl-N-(4-bromophenyl)] | 89-90 | tan solid | (520, 522), (518, 520) |
| 184 | [structure: 4,6-bis(2,2,2-trifluoroethoxy)-3-fluoropyridin-2-yl urea with N-methyl-N-(4-trifluoromethylphenyl)] | 111-112 | tan solid | (511), (508) |
| 185 | [structure: 4,6-bis(2,2,2-trifluoroethoxy)-3-fluoropyridin-2-yl urea with N-methyl-N-(4-trifluoromethoxyphenyl)] | 114-115 | tan solid | (527), (524) |

Example 16

Insecticidal Testing

The compounds identified in Table 1 were tested against beet armyworm and corn earworm as follows:
Insecticidal Test for Corn Earworm (*Helicoverpa zea*) and Beet Armyworm (*Spodoptera exigua*).

To prepare test solution, the test compound was formulated at 2000 ppm solution as 4 mg/2 mL of 9 acetone: 1 tap water. 50 μL of the 2000 ppm (equivalent to 50 μg/cm² dose on diet surface area) test solution was pipetted upon the surface of 1 mL of lepidopteran diet (Southland Multi-Species Lepidopteran Diet) contained in each of eight wells per insect species (one well=1 replication). A second-instar corn earworm and beet armyworm was placed upon the treated diet in each well once the solvent had air-dried. Trays containing the treated diet and larvae were covered and then held in a growth chamber at 25° C., 50-55% RH, and 16 hr light:8 hr dark for 5 days. Observation were conducted 5 days after treatment and infestation. The number of dead insects of 8 per species per treatment was then determined and the results are given in Table 2 as a percent control at a dose of 50 mg/cm².

TABLE 2

Insecticidal Activity

| Compound Number | MOLSTRUCTURE | HELIZE AVG % Mortality (50 μg/cm²) | LAPHEG AVG % Mortality (50 μg/cm²) |
|---|---|---|---|
| 1 | [structure: 4,6-bis(2,2,2-trifluoroethoxy)pyrimidin-2-yl urea with 4-trifluoromethylphenyl] | 100 | 100 |

TABLE 2-continued

Insecticidal Activity

| Compound Number | MOLSTRUCTURE | HELIZE AVG % Mortality (50 μg/cm²) | LAPHEG AVG % Mortality (50 μg/cm²) |
|---|---|---|---|
| 2 | | 100 | 100 |
| 3 | | 100 | 100 |
| 4 | | 100 | 0 |
| 5 | | 50 | 25 |

TABLE 2-continued

Insecticidal Activity

| Compound Number | MOLSTRUCTURE | HELIZE AVG % Mortality (50 μg/cm²) | LAPHEG AVG % Mortality (50 μg/cm²) |
|---|---|---|---|
| 6 | | 63 | 0 |
| 7 | | 100 | 100 |
| 8 | | 100 | 100 |
| 9 | | 88 | 100 |

TABLE 2-continued

| | Insecticidal Activity | | |
|---|---|---|---|
| Compound Number | MOLSTRUCTURE | HELIZE AVG % Mortality (50 μg/cm$^2$) | LAPHEG AVG % Mortality (50 μg/cm$^2$) |
| 10 | | 0 | 100 |
| 11 | | 100 | 100 |
| 12 | | 100 | 100 |

TABLE 2-continued

| | | Insecticidal Activity | |
|---|---|---|---|
| Compound Number | MOLSTRUCTURE | HELIZE AVG % Mortality (50 μg/cm$^2$) | LAPHEG AVG % Mortality (50 μg/cm$^2$) |
| 13 | | 100 | 100 |
| 14 | | 100 | 100 |
| 15 | | 50 | 75 |
| 16 | | 0 | 100 |
| 17 | | 0 | 100 |

TABLE 2-continued

| | | Insecticidal Activity | |
|---|---|---|---|
| Compound Number | MOLSTRUCTURE | HELIZE AVG % Mortality (50 μg/cm²) | LAPHEG AVG % Mortality (50 μg/cm²) |
| 18 | | 100 | 100 |
| 19 | | 100 | 100 |
| 20 | | 100 | 100 |
| 21 | | 100 | 100 |

TABLE 2-continued

| | | Insecticidal Activity | |
|---|---|---|---|
| Compound Number | MOLSTRUCTURE | HELIZE AVG % Mortality (50 μg/cm$^2$) | LAPHEG AVG % Mortality (50 μg/cm$^2$) |
| 22 | | 100 | 100 |
| 23 | | 100 | 100 |
| 24 | | 100 | 100 |
| 25 | | 100 | 0 |

TABLE 2-continued

| | Insecticidal Activity | | |
|---|---|---|---|
| Compound Number | MOLSTRUCTURE | HELIZE AVG % Mortality (50 μg/cm$^2$) | LAPHEG AVG % Mortality (50 μg/cm$^2$) |
| 26 | | 100 | 100 |
| 27 | | 100 | 100 |
| 28 | | 100 | 100 |
| 29 | | 100 | 100 |

TABLE 2-continued

| | Insecticidal Activity | | |
|---|---|---|---|
| Compound Number | MOLSTRUCTURE | HELIZE AVG % Mortality (50 μg/cm$^2$) | LAPHEG AVG % Mortality (50 μg/cm$^2$) |
| 30 | | 100 | 88 |
| 31 | | 100 | 100 |
| 32 | | 100 | 100 |
| 33 | | 100 | 100 |

TABLE 2-continued

| | | Insecticidal Activity | |
|---|---|---|---|
| Compound Number | MOLSTRUCTURE | HELIZE AVG % Mortality (50 µg/cm$^2$) | LAPHEG AVG % Mortality (50 µg/cm$^2$) |
| 34 | | 100 | 100 |
| 35 | | 100 | 100 |
| 36 | | 100 | 100 |

TABLE 2-continued

| | Insecticidal Activity | | |
|---|---|---|---|
| Compound Number | MOLSTRUCTURE | HELIZE AVG % Mortality (50 µg/cm$^2$) | LAPHEG AVG % Mortality (50 µg/cm$^2$) |
| 37 | | 100 | 100 |
| 38 | | 100 | 100 |
| 39 | | 100 | 100 |
| 40 | | 100 | 100 |

TABLE 2-continued

Insecticidal Activity

| Compound Number | MOLSTRUCTURE | HELIZE AVG % Mortality (50 μg/cm²) | LAPHEG AVG % Mortality (50 μg/cm²) |
|---|---|---|---|
| 41 | | 100 | 100 |
| 42 | | 100 | 100 |
| 43 | | 100 | 100 |
| 44 | | 100 | 100 |
| 45 | | 100 | 100 |

TABLE 2-continued

| | Insecticidal Activity | | |
|---|---|---|---|
| Compound Number | MOLSTRUCTURE | HELIZE AVG % Mortality (50 μg/cm²) | LAPHEG AVG % Mortality (50 μg/cm²) |
| 46 | | 100 | 100 |
| 47 | | 100 | 100 |
| 48 | | 100 | 100 |
| 49 | | 100 | 100 |
| 50 | | 100 | 100 |

TABLE 2-continued

Insecticidal Activity

| Compound Number | MOLSTRUCTURE | HELIZE AVG % Mortality (50 µg/cm²) | LAPHEG AVG % Mortality (50 µg/cm²) |
|---|---|---|---|
| 51 | | 0 | 100 |
| 52 | | 100 | 100 |
| 53 | | 100 | 100 |
| 54 | | 100 | 100 |

TABLE 2-continued

| | | Insecticidal Activity | |
|---|---|---|---|
| Compound Number | MOLSTRUCTURE | HELIZE AVG % Mortality (50 μg/cm²) | LAPHEG AVG % Mortality (50 μg/cm²) |
| 55 | | 100 | 0 |
| 56 | | 100 | 0 |
| 57 | | 100 | 0 |
| 58 | | 100 | 100 |
| 59 | | 100 | 0 |

TABLE 2-continued

Insecticidal Activity

| Compound Number | MOLSTRUCTURE | HELIZE AVG % Mortality (50 μg/cm²) | LAPHEG AVG % Mortality (50 μg/cm²) |
|---|---|---|---|
| 60 | | 100 | 100 |
| 61 | | 100 | 100 |
| 62 | | 100 | 100 |
| 63 | | 100 | 100 |

TABLE 2-continued

| | | Insecticidal Activity | |
|---|---|---|---|
| Compound Number | MOLSTRUCTURE | HELIZE AVG % Mortality (50 μg/cm$^2$) | LAPHEG AVG % Mortality (50 μg/cm$^2$) |
| 64 | | 100 | 100 |
| 65 | | 100 | 100 |
| 66 | | 100 | 100 |
| 67 | | 100 | 100 |

TABLE 2-continued

| | Insecticidal Activity | | |
|---|---|---|---|
| Compound Number | MOLSTRUCTURE | HELIZE AVG % Mortality (50 μg/cm²) | LAPHEG AVG % Mortality (50 μg/cm²) |
| 68 | | 100 | 100 |
| 69 | | 100 | 100 |
| 70 | | 100 | 100 |
| 71 | | 100 | 100 |

TABLE 2-continued

| | | Insecticidal Activity | |
|---|---|---|---|
| Compound Number | MOLSTRUCTURE | HELIZE AVG % Mortality (50 μg/cm²) | LAPHEG AVG % Mortality (50 μg/cm²) |
| 72 | | 100 | 0 |
| 73 | | n/a | n/a |
| 74 | | 100 | 100 |
| 75 | | n/a | n/a |

TABLE 2-continued

Insecticidal Activity

| Compound Number | MOLSTRUCTURE | HELIZE AVG % Mortality (50 μg/cm$^2$) | LAPHEG AVG % Mortality (50 μg/cm$^2$) |
| --- | --- | --- | --- |
| 76 | | 100 | 100 |
| 77 | | 100 | 100 |
| 78 | | 100 | 100 |
| 79 | | 100 | 100 |

TABLE 2-continued

| Insecticidal Activity | | | |
|---|---|---|---|
| Compound Number | MOLSTRUCTURE | HELIZE AVG % Mortality (50 µg/cm$^2$) | LAPHEG AVG % Mortality (50 µg/cm$^2$) |
| 80 | | 100 | 100 |
| 81 | | 100 | 100 |
| 82 | | 0 | 100 |
| 83 | | 100 | 100 |
| 84 | | 100 | 100 |

TABLE 2-continued

| | Insecticidal Activity | | |
|---|---|---|---|
| Compound Number | MOLSTRUCTURE | HELIZE AVG % Mortality (50 μg/cm$^2$) | LAPHEG AVG % Mortality (50 μg/cm$^2$) |
| 85 | | 100 | 100 |
| 86 | | 100 | 100 |
| 87 | | 100 | 100 |
| 88 | | 100 | 100 |

TABLE 2-continued

| | | Insecticidal Activity | |
|---|---|---|---|
| Compound Number | MOLSTRUCTURE | HELIZE AVG % Mortality (50 μg/cm$^2$) | LAPHEG AVG % Mortality (50 μg/cm$^2$) |
| 89 | | 100 | 100 |
| 90 | | 100 | 100 |
| 91 | | 100 | 100 |
| 92 | | 100 | 100 |

TABLE 2-continued
| | | Insecticidal Activity | |
|---|---|---|---|
| Compound Number | MOLSTRUCTURE | HELIZE AVG % Mortality (50 μg/cm$^2$) | LAPHEG AVG % Mortality (50 μg/cm$^2$) |
| 93 | 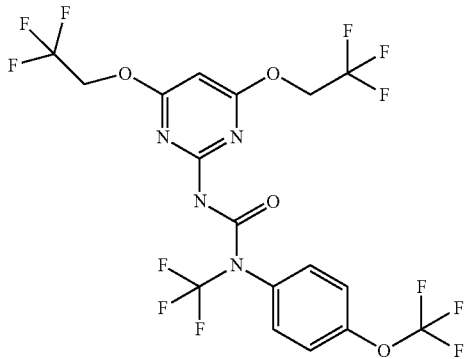 [SMILES: O=C(Nc1nc(OCC(F)(F)F)cc(OCC(F)(F)F)n1)N(c1ccc(OC(F)(F)F)cc1)C(F)(F)F] | 100 | 100 |
| 94 | 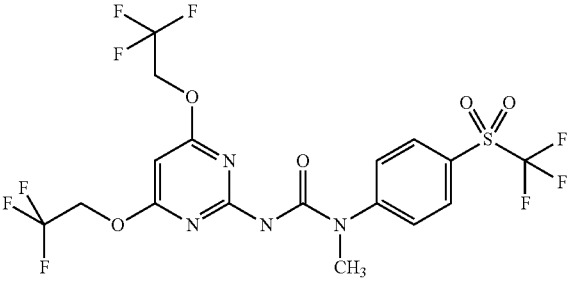 | 100 | 100 |
| 95 | 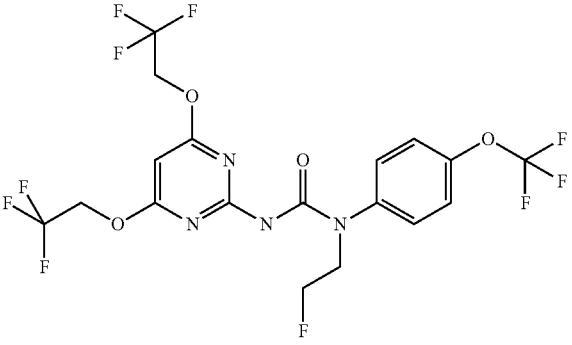 [SMILES: O=C(Nc1nc(OCC(F)(F)F)cc(OCC(F)(F)F)n1)N(CCF)c1ccc(OC(F)(F)F)cc1] | 100 | 100 |
| 96 | 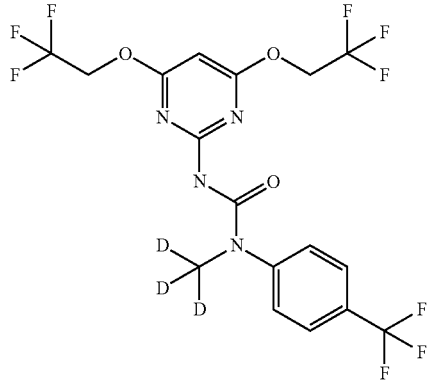 [SMILES: [2H]C([2H])([2H])N(C(=O)Nc1nc(OCC(F)(F)F)cc(OCC(F)(F)F)n1)c1ccc(C(F)(F)F)cc1] | 100 | 100 |

TABLE 2-continued

Insecticidal Activity

| Compound Number | MOLSTRUCTURE | HELIZE AVG % Mortality (50 μg/cm²) | LAPHEG AVG % Mortality (50 μg/cm²) |
| --- | --- | --- | --- |
| 97 | | 100 | 100 |
| 98 | | 100 | 100 |
| 99 | | 100 | 100 |
| 100 | | 100 | 100 |

TABLE 2-continued

| | | Insecticidal Activity | |
|---|---|---|---|
| Compound Number | MOLSTRUCTURE | HELIZE AVG % Mortality (50 μg/cm$^2$) | LAPHEG AVG % Mortality (50 μg/cm$^2$) |
| 101 | | 100 | 100 |
| 102 | | 100 | 0 |
| 103 | | 100 | 25 |
| 104 | | 100 | 0 |
| 105 | | 0 | 100 |

TABLE 2-continued

| | | Insecticidal Activity | |
|---|---|---|---|
| Compound Number | MOLSTRUCTURE | HELIZE AVG % Mortality (50 μg/cm²) | LAPHEG AVG % Mortality (50 μg/cm²) |
| 106 | | 100 | 100 |
| 107 | | 100 | 100 |
| 108 | | 100 | 100 |
| 109 | | 25 | 88 |
| 110 | | 0 | 100 |

TABLE 2-continued

Insecticidal Activity

| Compound Number | MOLSTRUCTURE | HELIZE AVG % Mortality (50 µg/cm$^2$) | LAPHEG AVG % Mortality (50 µg/cm$^2$) |
| --- | --- | --- | --- |
| 111 | | 88 | 100 |
| 112 | | 100 | 50 |
| 113 | | 0 | 100 |
| 114 | | 100 | 100 |
| 115 | | 75 | 38 |

TABLE 2-continued

| | | Insecticidal Activity | |
|---|---|---|---|
| Compound Number | MOLSTRUCTURE | HELIZE AVG % Mortality (50 μg/cm$^2$) | LAPHEG AVG % Mortality (50 μg/cm$^2$) |
| 116 | | 0 | 100 |
| 117 | | 0 | 100 |
| 118 | | 100 | 100 |
| 119 | | 88 | 100 |
| 120 | | 100 | 100 |

TABLE 2-continued

| | | Insecticidal Activity | |
|---|---|---|---|
| Compound Number | MOLSTRUCTURE | HELIZE AVG % Mortality (50 μg/cm²) | LAPHEG AVG % Mortality (50 μg/cm²) |
| 121 | | 100 | 100 |
| 122 | | 88 | 100 |
| 123 | | 100 | 100 |
| 124 | | 100 | 100 |

TABLE 2-continued

Insecticidal Activity

| Compound Number | MOLSTRUCTURE | HELIZE AVG % Mortality (50 μg/cm$^2$) | LAPHEG AVG % Mortality (50 μg/cm$^2$) |
|---|---|---|---|
| 125 | | 100 | 88 |
| 126 | | 100 | 100 |
| 127 | | 100 | 0 |
| 128 | | 100 | 88 |

TABLE 2-continued

| | | Insecticidal Activity | |
|---|---|---|---|
| Compound Number | MOLSTRUCTURE | HELIZE AVG % Mortality (50 μg/cm$^2$) | LAPHEG AVG % Mortality (50 μg/cm$^2$) |
| 129 | | 100 | 100 |
| 130 | | 100 | 100 |
| 131 | | 100 | 100 |
| 132 | | 100 | 100 |
| 133 | | 100 | 100 |

TABLE 2-continued

| | | Insecticidal Activity | |
|---|---|---|---|
| Compound Number | MOLSTRUCTURE | HELIZE AVG % Mortality (50 μg/cm$^2$) | LAPHEG AVG % Mortality (50 μg/cm$^2$) |
| 134 | | 100 | 100 |
| 135 | | 100 | 100 |
| 136 | | 100 | 100 |
| 137 | | 100 | 88 |
| 138 | | 100 | 100 |

TABLE 2-continued
| | | Insecticidal Activity | |
|---|---|---|---|
| Compound Number | MOLSTRUCTURE | HELIZE AVG % Mortality (50 μg/cm$^2$) | LAPHEG AVG % Mortality (50 μg/cm$^2$) |
| 139 | 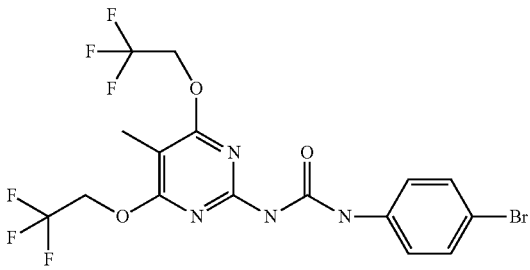 [SMILES: Cc1c(OCC(F)(F)F)nc(NC(=O)Nc2ccc(Br)cc2)nc1OCC(F)(F)F] | 88 | 88 |
| 140 | 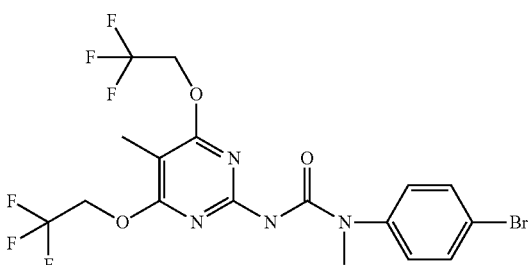 | 100 | 100 |
| 141 | 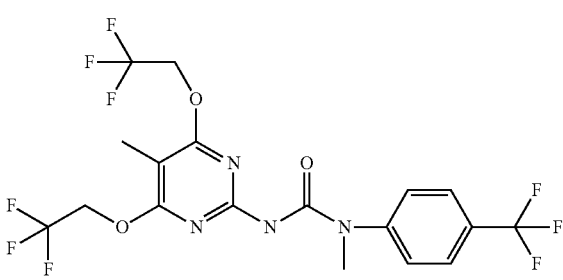 [SMILES: Cc1c(OCC(F)(F)F)nc(NC(=O)N(C)c2ccc(C(F)(F)F)cc2)nc1OCC(F)(F)F] | 100 | 100 |
| 142 | 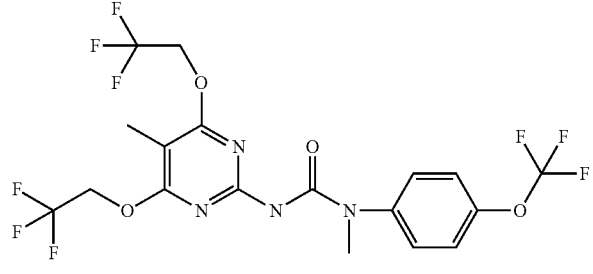 [SMILES: Cc1c(OCC(F)(F)F)nc(NC(=O)N(C)c2ccc(OC(F)(F)F)cc2)nc1OCC(F)(F)F] | 100 | 100 |
| 143 | 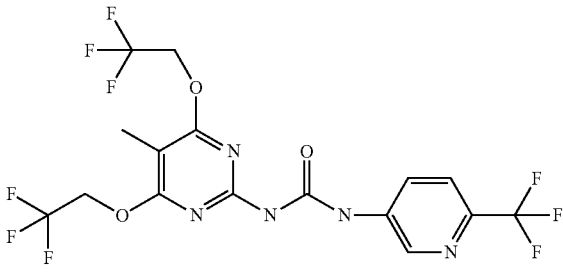 [SMILES: Cc1c(OCC(F)(F)F)nc(NC(=O)Nc2ccc(C(F)(F)F)nc2)nc1OCC(F)(F)F] | 100 | 100 |

TABLE 2-continued

| | | Insecticidal Activity | |
|---|---|---|---|
| Compound Number | MOLSTRUCTURE | HELIZE AVG % Mortality (50 μg/cm$^2$) | LAPHEG AVG % Mortality (50 μg/cm$^2$) |
| 144 | | 0 | 100 |
| 145 | | 0 | 100 |
| 146 | | 100 | 100 |
| 147 | | 100 | 88 |
| 148 | | 100 | 100 |

TABLE 2-continued

| | | Insecticidal Activity | |
|---|---|---|---|
| Compound Number | MOLSTRUCTURE | HELIZE AVG % Mortality (50 µg/cm$^2$) | LAPHEG AVG % Mortality (50 µg/cm$^2$) |
| 149 | | 100 | 100 |
| 150 | | 75 | 100 |
| 151 | | 100 | 100 |
| 152 | | 100 | 100 |
| 153 | | 100 | 100 |
| 154 | | 100 | 100 |

TABLE 2-continued

| | Insecticidal Activity | | |
|---|---|---|---|
| Compound Number | MOLSTRUCTURE | HELIZE AVG % Mortality (50 μg/cm²) | LAPHEG AVG % Mortality (50 μg/cm²) |
| 155 | | 100 | 50 |
| 156 | | 100 | 100 |
| 157 | | 100 | 100 |
| 158 | | 100 | 100 |

TABLE 2-continued

| | Insecticidal Activity | | |
|---|---|---|---|
| Compound Number | MOLSTRUCTURE | HELIZE AVG % Mortality (50 µg/cm$^2$) | LAPHEG AVG % Mortality (50 µg/cm$^2$) |
| 159 | | 0 | 100 |
| 160 | | 100 | 100 |
| 161 | | 100 | 100 |
| 162 | | 100 | 100 |
| 163 | | 100 | 100 |

TABLE 2-continued

Insecticidal Activity

| Compound Number | MOLSTRUCTURE | HELIZE AVG % Mortality (50 µg/cm²) | LAPHEG AVG % Mortality (50 µg/cm²) |
|---|---|---|---|
| 164 | | 100 | 88 |
| 165 | | 100 | 88 |
| 166 | | 100 | 100 |
| 167 | | 100 | 50 |
| 168 | | 100 | 100 |
| 169 | | 100 | 100 |

TABLE 2-continued

| | | Insecticidal Activity | |
|---|---|---|---|
| Compound Number | MOLSTRUCTURE | HELIZE AVG % Mortality (50 μg/cm$^2$) | LAPHEG AVG % Mortality (50 μg/cm$^2$) |
| 170 | | 100 | 75 |
| 171 | | 100 | 100 |
| 172 | | | |
| 173 | | | |
| 174 | | 100 | 0 |

TABLE 2-continued

Insecticidal Activity

| Compound Number | MOLSTRUCTURE | HELIZE AVG % Mortality (50 µg/cm²) | LAPHEG AVG % Mortality (50 µg/cm²) |
|---|---|---|---|
| 175 | | 100 | 100 |
| 176 | | 100 | 100 |
| 177 | | 100 | 100 |
| 178 | | 100 | 100 |

TABLE 2-continued

Insecticidal Activity

| Compound Number | MOLSTRUCTURE | HELIZE AVG % Mortality (50 μg/cm$^2$) | LAPHEG AVG % Mortality (50 μg/cm$^2$) |
|---|---|---|---|
| 179 | | 100 | 100 |
| 180 | | 100 | 100 |
| 181 | | 100 | 100 |
| 182 | | 100 | 100 |

TABLE 2-continued

Insecticidal Activity

| Compound Number | MOLSTRUCTURE | HELIZE AVG % Mortality (50 µg/cm²) | LAPHEG AVG % Mortality (50 µg/cm²) |
|---|---|---|---|
| 183 | | 50 | 100 |
| 184 | | 100 | 100 |
| 185 | | 100 | 100 |

Insecticide Utility

The compounds of the invention are useful for the control of invertebrates including insects. Therefore, the present invention also is directed to a method for inhibiting an insect which comprises applying an insect-inhibiting amount of a compound of formula (I) to a locus of the insect, to the area to be protected, or directly on the insect to be controlled. The compounds of the invention may also be used to control other invertebrate pests such as mites and nematodes.

The "locus" of insects or other pests is a term used herein to refer to the environment in which the insects or other pests live or where their eggs are present, including the air surrounding them, the food they eat, or objects which they contact. For example, insects which eat, damage or contact edible, commodity, ornamental, turf or pasture plants can be controlled by applying the active compounds to the seed of the plant before planting, to the seedling, or cutting which is planted, the leaves, stems, fruits, grain, and/or roots, or to the soil or other growth medium before or after the crop is planted. Protection of these plants against virus, fungus or bacterium diseases may also be achieved indirectly through controlling sap-feeding pests such as whitefly, plant hopper, aphid and spider mite. Such plants include those which are bred through conventional approaches and which are genetically modified using modern biotechnology to gain insect-resistant, herbicide-resistant, nutrition-enhancement, and/or any other beneficial traits.

It is contemplated that the compounds might also be useful to protect textiles, paper, stored grain, seeds and other foodstuffs, houses and other buildings which may be occupied by humans and/or companion, farm, ranch, zoo, or other animals, by applying an active compound to or near such objects. Domesticated animals, buildings or human beings might be protected with the compounds by controlling invertebrate and/or nematode pests that are parasitic or are capable of transmitting infectious diseases. Such pests include, for example, chiggers, ticks, lice, mosquitoes, flies, fleas and heartworms. Nonagronomic applications also include invertebrate pest control in forests, in yards, along road sides and railroad right of way.

The term "inhibiting an insect" refers to a decrease in the numbers of living insects, or a decrease in the number of viable insect eggs. The extent of reduction accomplished by a compound depends, of course, upon the application rate of the compound, the particular compound used, and the target insect species. At least an inactivating amount should be used. The term "insect-inactivating amount" is used to describe the amount, which is sufficient to cause a measurable reduction in the treated insect population. Generally an amount in the range from about 1 to about 1000 ppm by weight active compound is used. For example, insects or other pests which can be inhibited include, but are not limited to:

Lepidoptera—*Heliothis* spp., *Helicoverpa* spp., *Spodoptera* spp., *Mythimna unipuncta, Agrotis ipsilon, Earias* spp., *Euxoa auxiliaris, Trichoplusia ni, Anticarsia gemmatalis,*

*Rachiplusia nu, Plutella xylostella, Chilo* spp., *Scirpophaga incertulas, Sesamia inferens, Cnaphalocrocis medinalis, Ostrinia nubilalis, Cydia pomonella, Carposina niponensis, Adoxophyes orana, Archips argyrospilus, Pandemis heparana, Epinotia aporema, Eupoecilia ambiguella, Lobesia botrana, Polychrosis viteana, Pectinophora gossypiella, Pieris rapae, Phyllonorycter* spp., *Leucoptera malifoliella, Phyllocnisitis citrella*
Coleoptera—*Diabrotica* spp., *Leptinotarsa decemlineata, Oulema oryzae, Anthonomus grandis, Lissorhoptrus oryzophilus, Agriotes* spp., *Melanotus communis, Popillia japonica, Cyclocephala* spp., *Tribolium* spp.
Homoptera—*Aphis* spp., *Myzus persicae, Rhopalosiphum* spp., *Dysaphis plantaginea, Toxoptera* spp., *Macrosiphum euphorbiae, Aulacorthum solani, Sitobion avenae, Metopolophium dirhodum, Schizaphis graminum, Brachycolus noxius, Nephotettix* spp., *Nilaparvata lugens, Sogatella furcifera, Laodelphax striatellus, Bemisia tabaci, Trialeurodes vaporariorum, Aleurodes proletella, Aleurothrixus floccosus, Quadraspidiotus perniciosus, Unaspis yanonensis, Ceroplastes rubens, Aonidiella aurantii*
Hemiptera—*Lygus* spp., *Eurygaster maura, Nezara viridula, Piezodorus guildingi, Leptocorisa varicornis, Cimex lectularius, Cimex hemipterus*
Thysanoptera—*Frankliniella* spp., *Thrips* spp., *Scirtothrips dorsalis*
Isoptera—*Reticulitermes flavipes, Coptotermes formosanus, Reticulitermes virginicus, Heterotermes aureus, Reticulitermes hesperus, Coptotermes frenchii, Shedorhinotermes* spp., *Reticulitermes santonensis, Reticulitermes grassei, Reticulitermes banyulensis, Reticulitermes speratus, Reticulitermes hageni, Reticulitermes tibialis, Zootermopsis* spp., *Incisitermes* spp., *Marginitermes* spp., *Macrotermes* spp., *Microcerotermes* spp., *Microtermes* spp.
Diptera—*Liriomyza* spp., *Musca domestica, Aedes* spp., *Culex* spp., *Anopheles* spp., *Fannia* spp., *Stomoxys* spp.,
Hymenoptera—*Iridomyrmex humilis, Solenopsis* spp., *Monomorium pharaonis, Atta* spp., *Pogonomyrmex* spp., *Camponotus* spp., *Monomorium* spp., *Tapinoma sessile, Tetramorium* spp., *Xylocapa* spp., *Vespula* spp., *Polistes* spp.
Mallophaga (chewing lice)
Anoplura (sucking lice)—*Pthirus pubis, Pediculus* spp.
Orthoptera (grasshoppers, crickets)—*Melanoplus* spp., *Locusta migratoria, Schistocerca gregaria, Gryllotalpidae* (mole crickets).
Blattoidea (cockroaches)—*Blatta orientalis, Blattella germanica, Periplaneta americana, Supella longipalpa, Periplaneta australasiae, Periplaneta brunnea, Parcoblatta pennsylvanica, Periplaneta fuliginosa, Pycnoscelus surinamensis,*
Siphonaptera—*Ctenophalides* spp., *Pulex irritans*
Acari—*Tetranychus* spp., *Panonychus* spp., *Eotetranychus carpini, Phyllocoptruta oleivora, Aculus pelekassi, Brevipalpus phoenicis, Boophilus* spp., *Dermacentor variabilis, Rhipicephalus sanguineus, Amblyomma americanum, Ixodes* spp., *Notoedres cati, Sarcoptes scabiei, Dermatophagoides* spp.
Nematoda—*Dirofilaria immitis, Meloidogyne* spp., *Heterodera* spp., *Hoplolaimus columbus, Belonolaimus* spp., *Pratylenchus* spp., *Rotylenchus reniformis, Criconemella ornata, Ditylenchus* spp., *Aphelenchoides besseyi, Hirschmanniella* spp.
Compositions The compounds of this invention are applied in the form of compositions which are important embodiments of the invention, and which comprise a compound of this invention and a phytologically-acceptable inert carrier. Control of the pests is achieved by applying compounds of the invention in forms of sprays, topical treatment, gels, seed coatings, microcapsulations, systemic uptake, baits, eartags, boluses, foggers, fumigants aerosols, dusts and many others. The compositions are either concentrated solid or liquid formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids, usually known as wettable powders, or liquids usually known as emulsifiable concentrates or aqueous suspensions. Wettable powders, which may be compacted to form water dispersible granules, comprise an intimate mixture of the active compound, an inert carrier, and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional anionic and/or nonionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent and applying it to a granular carrier which has been preformed to the appropriate particle size, in the range of from about 0.5 to 3 mm. Such compositions may also be formulated by making a dough or paste of the carrier and compound and crushing and drying to obtain the desired granular particle size.

Dusts containing the compounds are prepared simply by intimately mixing the compound in powdered form with a suitable dusty agricultural carrier, such as kaolin clay, ground volcanic rock, and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and acaricides are generally applied in the form of a dispersion of the active ingredient in a liquid carrier. It is conventional to refer to application rates in terms of the concentration of active ingredient in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects and mites is not critical and can readily be determined by those skilled in the art in view of the examples above. In general, concentrations from 10 ppm to 5000 ppm by weight of compound are expected to provide good control. With many of the compounds, concentrations from 100 to 1500 ppm will suffice.

The locus to which a compound is applied can be any locus inhabited by an insect or mite, for example, vegetable crops, fruit and nut trees, grape vines, ornamental plants, domesticated animals, the interior or exterior surfaces of buildings, and the soil around buildings.

Because of the unique ability of insect eggs to resist toxicant action, repeated applications may be desirable to control newly emerged larvae, as is true of other known insecticides and acaricides.

Systemic movement of compounds of the invention in plants may be utilized to control pests on one portion of the plant by applying the compounds to a different portion of it. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include those expressing proteins toxic to invertebrate pests, such as *Bacillus thuringiensis* or other insecticidal proteins, those expressing herbicide resistance, such as "Roundup Ready®" seed, or those with "stacked" foreign genes expressing insecticidal proteins, herbicide resistance, nutrition-enhancement and/or any other beneficial traits.

An insecticidal bait composition consisting of compounds of the present invention and attractants and/or feeding stimulants may be used to increase efficacy of the insecticides against insect pest in a device such as trap, bait station, and the like. The bait composition is usually a solid, semi-solid (including gel) or liquid bait matrix including the stimulants and one or more non-microencapsulated or microencapsulated insecticides in an amount effective to act as kill agents.

The compounds of the present invention (Formula I) are often applied in conjunction with one or more other insecticides or fungicides or herbicides to obtain control of a wider variety of pests diseases and weeds. When used in conjunction with other insecticides or fungicides or herbicides, the presently claimed compounds can be formulated with the other insecticides or fungicides or herbicide, tank mixed with the other insecticides or fungicides or herbicides, or applied sequentially with the other insecticides or fungicides or herbicides.

Some of the insecticides that can be employed beneficially in combination with the compounds of the present invention include: antibiotic insecticides such as allosamidin and thuringiensin; macrocyclic lactone insecticides such as spinosad, spinetoram, and other spinosyns including the 21-butenyl spinosyns and their derivatives; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; biological insecticides such as *Bacillus popilliae, B. sphaericus, B. thuringiensis* subsp. *aizawai, B. thuringiensis* subsp. *kurstaki, B. thuringiensis* subsp. *tenebrionis, Beauveria bassiana, Cydia pomonella* granulosis virus, Douglas fir tussock moth NPV, gypsy moth NPV, *Helicoverpa zea* NPV, Indian meal moth granulosis virus, *Metarhizium anisopliae, Nosema locustae, Paecilomyces fumosoroseus, P. lilacinus, Photorhabdus luminescens, Spodoptera exigua* NPV, trypsin modulating oostatic factor, *Xenorhabdus nematophilus*, and *X. bovienii*, plant incorporated protectant insecticides such as Cry1Ab, Cry1Ac, Cry1F, Cry1A.105, Cry2Ab2, Cry3A, mir Cry3A, Cry3Bb1, Cry34, Cry35, and VIP3A; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluoron, buprofezin, chlorfluazuron, cyromazine, diflubenzuron, flucycloxuron, flufenoxuron, hexaflumuron, lufenuron, novaluron, noviflumuron, penfluoron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethylamine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoate-methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, methamidophos and propetamphos; phosphorodiamide insecticides such as dimefox, mazidox, mipafox and schradan; oxadiazine insecticides such as indoxacarb; phthalimide insecticides such as dialifos, phosmet and tetramethrin; pyrazole insecticides such as acetoprole, ethiprole, fipronil, pyrafluprole, pyriprole, tebufenpyrad, tolfenpyrad and vaniliprole; pyrethroid ester insecticides such as acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetronic acid insecticides such as spirodiclofen, spiromesifen and spirotetramat; thiourea insecticides such as diafenthiuron; urea insecticides such as flucofuron and sulcofuron; and unclassified insecticides such as AKD-3088, closantel, crotamiton, cyflumetofen, E2Y45, EXD, fenazaflor, fenazaquin, fenoxacrim, fenpyroximate, FKI-1033, flubendiamide, HGW86, hydramethylnon, IKI-2002, isoprothiolane, malonoben, metaflumizone, metoxadiazone, nifluridide, NNI-9850, NNI-0101, pymetrozine, pyridaben, pyridalyl, Qcide, rafoxanide, rynaxypyr, SYJ-159, triarathene and triazamate and any combinations thereof.

Some of the fungicides that can be employed beneficially in combination with the compounds of the present invention include: 2-(thiocyanatomethylthio)-benzothiazole, 2-phenylphenol, 8-hydroxyquinoline sulfate, Ampelomyces, quisqualis, azaconazole, azoxystrobin, *Bacillus subtilis*, benalaxyl, benomyl, benthiavalicarb-isopropyl, benzylaminobenzene-sulfonate (BABS) salt, bicarbonates, biphenyl, bismerthiazol, bitertanol, blasticidin-S, borax, Bordeaux mixture, boscalid, bromuconazole, bupirimate, calcium polysulfide, captafol, captan, carbendazim, carboxin, carpropamid, carvone, chloroneb, chlorothalonil, chlozolinate, *Coniothyrium* minitans, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fentin, fentin acetate, fentin hydroxide, ferbam, ferimzone, fluazinam, fludioxonil, flumorph, fluopicolide, fluoroimide, fluoxastrobin, fluquinconazole, flusilazole, flusulfamide, flutolanil, flutriafol, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, kasugamycin, kasugamycin hydrochloride hydrate, kresoxim-methyl, mancopper, mancozeb, maneb, mepanipyrim, mepronil, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrazophos, pyributicarb, pyrifenox, pyrimethanil, pyroquilon, quinoclamine, quinoxyfen, quintozene, Reynoutria sachalinensis extract, silthiofam, simeconazole, sodium 2-phenylphenoxide, sodium bicarbonate, sodium pentachlorophenoxide, spiroxamine, sulfur, SYP-Z071, tar oils, tebuconazole, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, vinclozolin, zineb, ziram, zoxamide, *Candida oleophila, Fusarium oxysporum, Gliocladium* spp., *Phlebiopsis gigantean, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme: ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, XRD-563, and zarilamid, and any combinations thereof.

Some of the herbicides that can be employed in conjunction with the compounds of the present invention include: amide herbicides such as allidochlor, beflubutamid, benzadox, benzipram, bromobutide, cafenstrole, CDEA, chlorthiamid, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flamprop and flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as benzfendizone, cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glyphosate and piperophos; phenoxy herbicides such as bromofenoxim, clomeprop, 2,4-DEB, 2,4-DEP, difenopenten, disul, erbon, etnipromid, fenteracol and trifopsime; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecopropand mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazolyl herbicides such as benzofenap, pyrazolynate, pyrasulfotole, pyrazoxyfen, pyroxasulfone and topramezone; pyrazolylphenyl herbicides such as fluazolate and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluoroxypyr, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as butafenacil, bromacil, flupropacil, isocil, lenacil and terbacil; 3-phenyluracils; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluoron, phenobenzuron, siduron, tetrafluoron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluoron and thidiazuron; and unclassified herbicides such as acrolein, allyl alcohol, azafenidin, benazolin, bentazone, benzobicyclon, buthidazole, calcium cyanamide, cambendichlor, chlorfenac, chlorfenprop, chlorflurazole, chlorflurenol, cinmethylin, clomazone, CPMF, cresol, ortho-dichlorobenzene, dimepiperate, endothal, fluoromidine, fluridone, fluorochloridone, flurtamone, fluthiacet, indanofan, methazole, methyl isothiocyanate, nipyraclofen, OCH, oxadiargyl, oxadiazon, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan and tritac.

We claim:
1. A compound of formula (I)

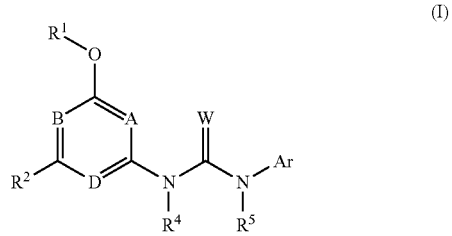

wherein
A, B and D represent N;
$R^1$ represents $C_1$-$C_4$ alkyl substituted with from one up to the maximum number of fluorine or chlorine atoms;
$R^2$ represents Cl, $CF_3$, O($C_1$-$C_3$ alkyl), NH($C_1$-$C_3$ alkyl) or N($C_1$-$C_3$ alkyl)$_2$ in which each of the $C_1$-$C_3$ alkyl groups is optionally substituted with from one up to the maximum number of fluorine atoms;
$R^4$ represents H, $C_1$-$C_3$ alkyl (optionally substituted with alkoxy, benzyloxy or —OC(O)$R^7$), or $CO_2R^6$;
$R^5$ represents H, $C_1$-$C_3$ alkyl (optionally substituted with $C_1$-$C_3$ alkoxy, F, CN or $CO_2R$), OH, $C_1$-$C_3$ alkoxy or $CO_2R^6$, or $R^4$ and $R^5$ taken together represent —$CH_2CH_2$— or —C(O)$CH_2$—;
$R^6$ represents H or $C_1$-$C_3$ alkyl;
$R^7$ represents $C_1$-$C_3$ alkyl;
W represents O or S;
Ar represents a phenyl group substituted with one to four substituents independently selected from F, Cl, Br, I, $NO_2$, CN, $SCF_3$, $SO_2CF_3$, $C_1$-$C_3$ alkyl substituted with from one up to the maximum number of chlorine or fluorine atoms, or $C_1$-$C_3$ alkoxy optionally substituted with from one up to the maximum number of chlorine or fluorine atoms; or represents

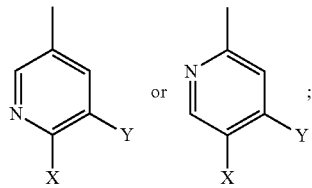

and
X and Y independently represent H, F, Cl, Br, I, $NO_2$, CN, $SCF_3$, $SO_2CF_3$, $C_1$-$C_3$ alkyl substituted with from one up to the maximum number of chlorine or fluorine atoms, or $C_1$-$C_3$ alkoxy optionally substituted with from one up to the maximum number of chlorine or fluorine atoms.

2. A compound according to claim 1 wherein Ar represents

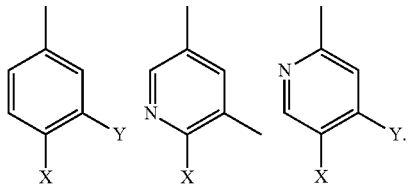

3. A compound according to claim 2 in which $R^1$ is $CH_2CF_3$.

4. A compound according to claim 2 in which $R^2$ is $OCH_2CF_3$.

5. A compound according to claim 2 in which W is O.

6. A compound according to claim 2 in which $R^4$ and $R^5$ are independently H or $CH_3$.

7. A compound according to claim 2 in which Ar represents

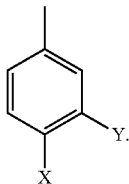

8. A compound according to claim 2 in which X is Br, Cl, $CF_3$ or $OCF_3$.

9. A composition for controlling insects which comprises a compound of claim 1 in combination with a phytologically-acceptable carrier.

10. A method of controlling insects which comprises applying to a locus where control is desired an insect-inactivating amount of a compound of claim 1.

\* \* \* \* \*